US005620676A

United States Patent [19]
Jacobson et al.

[11] Patent Number: 5,620,676
[45] Date of Patent: Apr. 15, 1997

[54] BIOLOGICALLY ACTIVE ATP ANALOGS

[75] Inventors: Kenneth A. Jacobson, Silver Spring, Md.; Bilha Fischer, Holon, Israel; Michel Maillard, Cambridge, Mass.

[73] Assignee: The United States of America as represented by the Department of Health and Human Services, Washington, D.C.

[21] Appl. No.: 414,438

[22] Filed: Mar. 31, 1995

Related U.S. Application Data

[63] Continuation-in-part of Ser. No. 207,870, Mar. 8, 1994, abandoned.

[51] Int. Cl.$^6$ ............................ A61K 51/00; A61M 36/14
[52] U.S. Cl. ...................... 424/1.73; 424/1.65; 514/263; 514/260; 536/28.54; 536/28.55
[58] Field of Search ................................ 424/1.73, 1.11, 424/1.65, 1.81, 1.85; 514/263, 260; 536/28.55, 28.54

[56] References Cited

U.S. PATENT DOCUMENTS

| | | | |
|---|---|---|---|
| 3,998,953 | 12/1976 | Konz et al. | 514/263 |
| 4,340,728 | 7/1982 | Endo et al. | 536/28.55 |
| 4,883,801 | 11/1989 | Nathanson | 514/263 |
| 5,051,426 | 9/1991 | Parnell | 514/263 |
| 5,082,845 | 1/1992 | Wolf et al. | 514/263 |
| 5,112,827 | 5/1992 | Saunders et al. | 514/263 |
| 5,169,849 | 12/1992 | Kiechel et al. | 514/263 |
| 5,219,858 | 6/1993 | Parnell | 514/263 |
| 5,288,701 | 2/1994 | Klein et al. | 514/263 |
| 5,314,890 | 5/1994 | Agostini et al. | 514/263 |
| 5,340,813 | 8/1994 | Klein et al. | 514/263 |
| 5,354,756 | 10/1994 | Underiner et al. | 514/263 |
| 5,366,977 | 11/1994 | Pollard et al. | 514/263 |
| 5,436,143 | 7/1995 | Human | 435/91.1 |
| 5,446,031 | 8/1995 | Sakata et al. | 536/28.54 |
| 5,470,579 | 11/1995 | Bonte et al. | 514/263 |
| 5,470,878 | 11/1995 | Michnick et al. | 514/558 |
| 5,473,070 | 12/1995 | Underiner et al. | 544/267 |
| 5,478,831 | 12/1995 | Furrer et al. | 514/263 |

FOREIGN PATENT DOCUMENTS

| | | |
|---|---|---|
| 0590919 | 6/1994 | European Pat. Off. . |
| 0628311 | 12/1994 | European Pat. Off. . |
| 9217186 | 10/1992 | WIPO . |
| 9411001 | 5/1994 | WIPO . |
| 9416704 | 8/1994 | WIPO . |

OTHER PUBLICATIONS

Kim et al. J. Med. Chem. (1994), vol. 37, pp. 3373–3382. "Structure–Activity Relationships of 1,3–dialkylxanthine Derivative at Rat A3 Adenosine Receptors".

Nemčková et al. Monatshefte für Chemie, vol. 126, pp. 799–804 (1995). "7–Substituted 8–Vinyl–1,3–dimethyl–3, 7–dihydro–1–H–purine–2,6–diones and their Broncholytic Activity".

Hesek and Rybar. Monatshefte für Chemie, vol. 125, pp. 1273–1278 (1994). "[f]–Fused Purine–2,6–diones:Synthesis of New [1,3,5]–and [1,3,6]–Thiadiaze–pino–[3,2–f]–purine Ring Systems".

Gungor et al. J. Med. Chem. (1994) vol. 37, pp. 4307–4316 "N6–Substituted Adenosine Receptor Agonist. Synthesis and Pharmocological Activity as Potent Antinociceptive Agents".

Kinouchi et al. Stroke (Dallas) (1990), vol 21. No. 9, pp. 1326–1332 "Phenytoin Affects Metabolism of Free Fatty Acids and Nucleotides in Rat Cerebral Ischemia".

Dox et al. The Harper Collins Illustrated Medical Dictionary (1993) p. 432.

Jacobson et al. Biochemistry (1995), vol. 34, pp. 9088–9094. "Stimulation by Alkylxanthines of Chloride Efflux in CFPAC–1 Cells Does Not Involve A1 Adenosine Receptors".

Jacobson (1990), Comprehensive Medicinal Chemistry, vol. 3, pp. 601–642, "Adenosine ($P_1$) and ATP ($P_2$) Receptors".

Satchell et al. (1975). J. Pharmacol. Exp. Ther., vol. 35, No. 3, pp. 540–548. "Inhibitory Effects of Adenine Nucleotide Analogs on the Isolated Guinea–Pig Taenia Coli".

St. Claire, III (1991). Anal. Chem., vol. 63, pp. 2657–2660. "Two Dimensional Ion Pairing Reverse Phase Chromatography of Nucleosides and Nucleotides on Polymeric and Silica Stationary Phase Supports".

Cusack et al. (1990), Annuals of New York Academy of Sciences, vol. 603, pp. 172–181, "Subtypes of $P_2$–purinoceptors".

Daly (1982), J. Medicinal Chemistry, vol. 25, No. 3, pp. 197–207, "Adenosine Receptors: Targets for Future Drugs".

Fedan et al. (1986), European Journal of Pharmacology, vol. 129, pp. 279–291, "Further comparison of contractions of the smooth muscle of the guinea pig isolated vas deferens induced by ATP and related analogs".

(List continued on next page.)

*Primary Examiner*—John Kight
*Assistant Examiner*—Dameron L. Jones
*Attorney, Agent, or Firm*—Leydig, Voit & Mayer, Ltd.

[57] ABSTRACT

The present invention provides certain novel adenosine triphosphate (ATP) analogs, pharmaceutical compositions, and methods of using such analogs in the treatment of septic shock and other disease conditions. Examples of the ATP analogs include the mono-, di- and triphosphates of adenosines with various selected substituents at the 2, 6, 8, and 9-positions, such as alkyl, alkylphenyl, phenylalkyl, S-alkyl, S-alkenyl, S-alkylcyano, S-phenyl, S-alkylphenyl, S-alkylamino, S-alkylthioalkyl, S-alkylthiocyanato, S-alkylaminophenyl, S-alkylnitrophenyl, hydroxy, bromo, fluoro, chloro, and aminoalkylamino. The present invention also provides pharmaceutical compositions of and methods of using certain xanthine and uracil derivatives for the above disease conditions. Examples of the xanthine derivatives include xanthines having alkyl or alkyltriphosphate substituents at the 1, 3, and 7-positions. Examples of the uracil derivatives include 5-fluoro- and 5-bromo uracil triphosphates. Also provided are assays for assessing the binding of the ATP analogs.

34 Claims, 16 Drawing Sheets

OTHER PUBLICATIONS

Jacobson et al. (1992). Journal of Medicinal Chemistry, vol. 35, No. 3, pp. 407–422, "Adenosine Receptors: Pharmacology, Structure Activity Relationships, and Therapeutical Potential".

Abbracchio et al (1993). Drug Development Research, vol. 28, pp. 207–213, "Purinoceptor Nomenclature: A Status Report".

Bo et al (1993). Triphosphate, the Key Structure of the ATP Molecule Responsible for Interaction With $P_{2x}$–Purinoceptors, Gen. Pharmac. vol. 24, No. 3. pp. 637–640.

Boyer et al (1989). J. Biological Chemistry, vol. 264, No. 2, pp. 884–890, "Kinetics of Activation of Phospholipase C. by $P_{24}$Purinergic Receptor Agonists and Guanine Nucleotides".

Bruns (1991). Nucleosides & Nucleotides, vol. 10, No. 5, pp. 931–943, "Role of Adenosine in Energy Supply/Demand Balance".

Bwinstock (1991), Nucleosides & Nucleotides, vol. 10, No. 5, pp. 917–930, "Distribution and Roles of Purinoceptor Subtypes".

Bwinstock et al (1987). J. Pharmac., vol. 90, pp. 383–391, "$P_2$–purinoceptors of two subtypes in the rabbit mesenteric artery: reactive blue 2 selectively inhibits responses mediated via the $P_{24}$–but not the $P_{2x}$–purinoceptor".

Cysack (1993). Drug Development Research, vol. 28, pp. 244–252, "$_2$receptor: Subclassification and Structure Activity Relationships".

Cusak et al (1991), Nucleosides and Nucleotides, vol. 10, No. 5, pp. 1019–1028, "Design, Syntheses, and Pharmacology of ATP Analogues Selective for Subtypes of $P_2$–purinoceptors".

BIOLOGICALLY ACTIVE ATP ANALOGS

CROSS-REFERENCE TO RELATED APPLICATION

This is a continuation-in-part application of U.S. patent application Ser. No. 08/207,870, filed Mar. 8, 1994 now abandoned.

TECHNICAL FIELD OF THE INVENTION

The present invention relates to certain biologically active ATP analogs, their synthesis, and their use in pharmaceutical compositions and methods for the treatment of septic shock and other disease conditions.

BACKGROUND OF THE INVENTION

Purines such as adenosine have been shown to play a wide array of roles in biological systems. For example, physiological roles played by adenosine include, inter alia, modulator of vasodilation and hypotension, muscle relaxant, central depressant, inhibitor of platelet aggregation, regulator of energy supply/demand, responder to oxygen availability, neurotransmitter, and neuromodulator. (Bruns, *Nucleosides & Nucleotides*, 10(5), 931–934 (1991)). Because of its potent actions on many organs and systems, adenosine and its receptors have been the subject of considerable drug-development research (Daly, *J. Med. Chem.*, 25, 197 (1982)). Potential therapeutic applications for agonists include, for instance, the prevention of reperfusion injury after cardiac ischemia or stroke, and treatment of hypertension and epilepsy (Jacobson, et al., *J. Med. Chem.*, 35, 407–422 (1992)). Adenosine itself has recently been approved for the treatment of paroxysmal supra ventricular tachycardia (Pantely, et al., *Circulation*, 82, 1854 (1990)).

The present invention relates to the neurotransmitter role of purines, in particular, to the purine nucleotide adenosine-5'-triphosphate (ATP), and certain analogs thereof. The neurotransmitter role of ATP is mediated by certain receptors, known collectively as $P_2$-purinergic receptors ("$P_2$ receptors"). $P_2$ receptors are more responsive to ATP and the diphosphate form of adenosine (ADP) than they are to the monophosphate form of adenosine (AMP) and adenosine itself. Other aspects of these receptors relevant to an appreciation of the present invention include the fact that they are not antagonized by methylxanthines, a compound that is structurally related to ATP. Nor do these receptors act via an adenylate cyclase system, as is the case of other neurotransmitters (see Burnstock, *Drug Develop. Res.*, 28, 195–206 (1993)).

$P_2$ receptors have been sub-classified into several major nucleotide receptor subtypes on the basis of relative potencies of ATP analogs and on selective antagonism (Burnstock et al., *Gen. Pharmacol.*, 16, 433–440 (1985a); Gordon, *Biochem. J.*, 233, 309–319 (1986)). For example, $P_{2X}$ receptors are activated by α,β-methylene-ATP and apparently consist of ligand-gated cation channels (Benham et al., *Nature*, 328, 275–278 (1987); Benham, *J. Physiol.*, 419, 689–701 (1989); and Bean, *Trends Pharmacol. Sci.*, 13, 87–90 (1992)). $P_{2Y}$-receptors are activated by 2-methylthio-ATP and are linked to second messengers via G-proteins. The principal second messenger system activated by $P_{2Y}$ receptors is the metabolism of phosphatidyl inositol (Harden et al., *Biochem. J.*, 252, 583–593 (1988); Boyer et al., *J. Biol. Chem.*, 264, 884–890 (1989); Pirroton et al., *J. Biol. Chem*, 262, 17461 (1987); Haggblad et al., *Neurosci. Lett.*, 74, 199–204 (1987)), leading to liberation of intracellular calcium stores, activation of protein kinase C, and increases in cytoplasmic calcium. A less clearly defined subtype of the $P_2$ receptor family, the $P_{2U}$ receptor (Dubyak, *Amer. J. Respir. Cell. Molec. Biol.*, 4, 295–300 (1991)), also promotes inositol lipid hydrolysis and is activated by ATP and UTP, but not by many analogs of ATP, UTP, and ADP. Other cell-specific $P_2$ receptors include $P_{2T}$ receptors, which regulate platelet cell function (Hoyle et al., in *Adenosine in the Nervous System* (T. W. Stone, ed., Academic Press, London, 1991), pp. 43–76; Gordon, supra; Hoyle, in *Autonomic Neuroeffector Mechanisms* (G. Burnstock and C. H. V. Hoyle, eds., Harwood Academic Publishers, 1992), pp. 367–407), and $P_{2Z}$ receptors, which regulate ion permeability in mast cells, fibroblasts and leukocytes (Hoyle et al., supra; Gordon, supra; Hoyle, supra; Tatham et al., *Eur. J. Pharmacol.*, 147, 13–21 (1988)).

The $P_{2X}$ and $P_{2Y}$ receptors are widely distributed subtypes, being found on smooth muscle cells of the cardiovascular, gastrointestinal and genitourinary systems, and cardiac muscle, and many diverse cell types, including: endothelial cells, hepatocytes, erythrocytes, pancreatocytes, pulmonary alveolar cells, autonomic ganglionic neurons, sensory neurons, and also within the central nervous system (see Hoyle et al., supra; Hoyle, supra).

The $P_{2X}$ receptor mainly mediates constriction of smooth muscle in visceral organs, such as urinary bladder, vas deferens, and blood vessels (Burnstock, *Nucleos. & Nucleot.*, 10, 917–930 (1991)). The endogenous ligand for this receptor is probably ATP, which was demonstrated in the work of Suet al. (*Science*, 173, 336–338 (1971)). Several ATP derivatives, such as the aforementioned α,β-methylene ATP, have been demonstrated to have greater selectivity and potency than ATP itself, all of which have a modified triphosphate chain (see Bo et al., *Gen. Pharmac.*, 24, 637–640 (1993)). The results of various earlier studies, commented upon by Bo et al., supra, indicate that modifications of the triphosphate chain improve the efficacy of certain agonists of the $P_{2X}$ receptor. The results of Bo et al. confirmed this observation and extended it by indicating that the polyphosphate chain was also responsible for the affinity of ATP for the $P_{2X}$ receptor.

The $P_{2Y}$ receptor appears to have opposite effects relative to the $P_{2X}$ receptor in that activation of the $P_{2Y}$ receptor with extracellular ATP induces relaxation of visceral and vascular smooth muscle. In particular, the response of $P_{2Y}$ activation has been studied in the taenia coli, the aorta, erythrocyte membranes, and other systems of study. Interactions of certain ligands with $P_{2Y}$ receptors often is correlated with phospholipase C activity, which is discussed further hereinbelow.

Pharmacological, biochemical, and structural characterization of $P_2$ receptors and their natural and synthetic ligands has been relatively limited, due to a multiplicity of biological effects and inconsistencies in the potency of "selective" agents (see Inoue et al.,*News in Physiol. Sci.*, 2, 56–58 (1992); Silinsky, The *Neurosciences*, 1, 155–165 (1989)), and the great difficulties in synthesis and purification of nucleoside triphosphates and their analogs. In view of the early results that indicates that only diphosphorylated and triphosphorylated species have activity at the $P_2$ receptors, the identification of truly selective agents for one of the $P_2$ receptors may not result in readily applicable pharmaceuticals because of the difficulty in keeping such molecules from rapidly being broken down in the ordinary course of ATP metabolism. Regarding the pursuit of candidate antagonist compounds, one research report states that "[i]n spite of a considerable effort to produce new ATP derivatives and, in particular, to produce antagonists to $P_2R$ [i.e., $P_2$ receptors], not one selective $P_2R$ subtype antagonist has so far been obtained" (Zimmet et al., *Nucleos. & Nucleot.*, 12(1), 1–20 (1993)). Accordingly, drug development that would capitalize on the $P_2$ receptor biology has been slow in realization.

In view of the background recited hereinabove, it is an object of the present invention to provide new $P_2$ receptor ligands. Such ligands preferably would have the advantages of being selective for a single subclass, being relatively easy to synthesize, having a charge suitable for crossing cell membranes readily, being resistant to cleavage consequent to ATP metabolism, and having activity that is greater than that of ATP itself. It is a further object of the present invention to provide pharmaceutical compositions that incorporate the newly disclosed receptor ligands. Yet a further object of the present invention is to provide methods of use of the disclosed receptor ligands in the in vivo treatment of various disease conditions that can be treated by manipulation of $P_2$ receptor function.

These and other objects and advantages of the present invention, as well as additional inventive features, will be apparent from the description of the invention provided herein.

BRIEF SUMMARY OF THE INVENTION

The present invention provides a compound of the formula

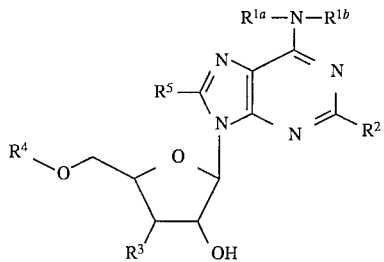

(I)

wherein $R^{1a}$ and $R_{1b}$ are individually hydrogen, $(C_1-C_7)$alkyl, $(C_1-C_7)$alkylphenyl, or phenyl$(C_1-C_7)$alkyl; $R^2$ is selected from the group consisting of S-$(C_1-C_{11})$alkyl, S-$(C_1-C_7)$alkenyl, S-$(C_1-C_7)$alkylcyano, S-$(C_3-C_7)$cycloalkyl, S-phenyl, S-$(C_1-C_3)$alkylphenyl, S-$(C_1-C_7)$alkylamino, S-$(C_1-C_7)$alkylthio$(C_1-C_7)$alkyl, S-$(C_1-C_7)$alkylthiocyanato, S-$(C_1-C_3)$alkylaminophenyl, S-$(C_1-C_3)$alkylnitrophenyl, and hydrogen; $R^3$ is selected from the group consisting of $(C_1-C_7)$alkyl, $(C_1-C_7)$alkylamino, $(C_5-C_{10})$aryl, $(C_5-C_{10})$arylamino, amino, amido, and hydroxyl; $R^4$ is monophosphate, diphosphate, or triphosphate; and $R^5$ is selected from the group consisting of bromo, fluoro, chloro, amino $(C_1-C_7)$alkylamino, and hydrogen;

provided that when $R^3$ is hydroxyl, then at least one of $R^{1a}$, $R^1$, R2, and $R^5$ is not hydrogen; and further provided that when $R^4$ is triphosphate, $R^3$ is hydroxyl and $R^5$ is hydrogen.

The present invention also provides a compound of the formula:

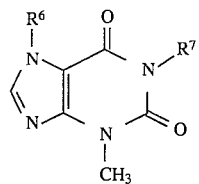

(II)

wherein $R^6$ and $R^7$ are different and are $(C_1-C_3)$alkyltriphosphate or $(C_1-C_3)$alkyl.

The present invention further provides a pharmaceutical composition comprising a pharmaceutically acceptable carrier and at least one compound having the formula (I), (II), or

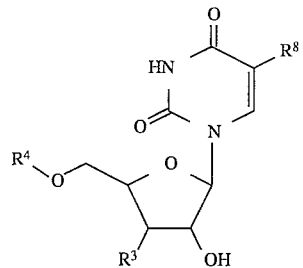

(III)

wherein $R^{1a}$, $R^{1b}$, $R^2$, $R^3$, $R^5$, $R^6$, and $R^7$ are defined as above; and $R^8$ is halogen or hydrogen. The present invention also provides methods for the selective activation $P_{2X}$ and $P_{2Y}$ receptors, and for the treatment of septic shock and brain seizures as well as for the enhancement of learning and memory capabilities, comprising contacting an effective quantity of one or a combination of the aforementioned compounds to the aforementioned receptors.

DESCRIPTION OF THE PREFERRED EMBODIMENTS

Figure 1:
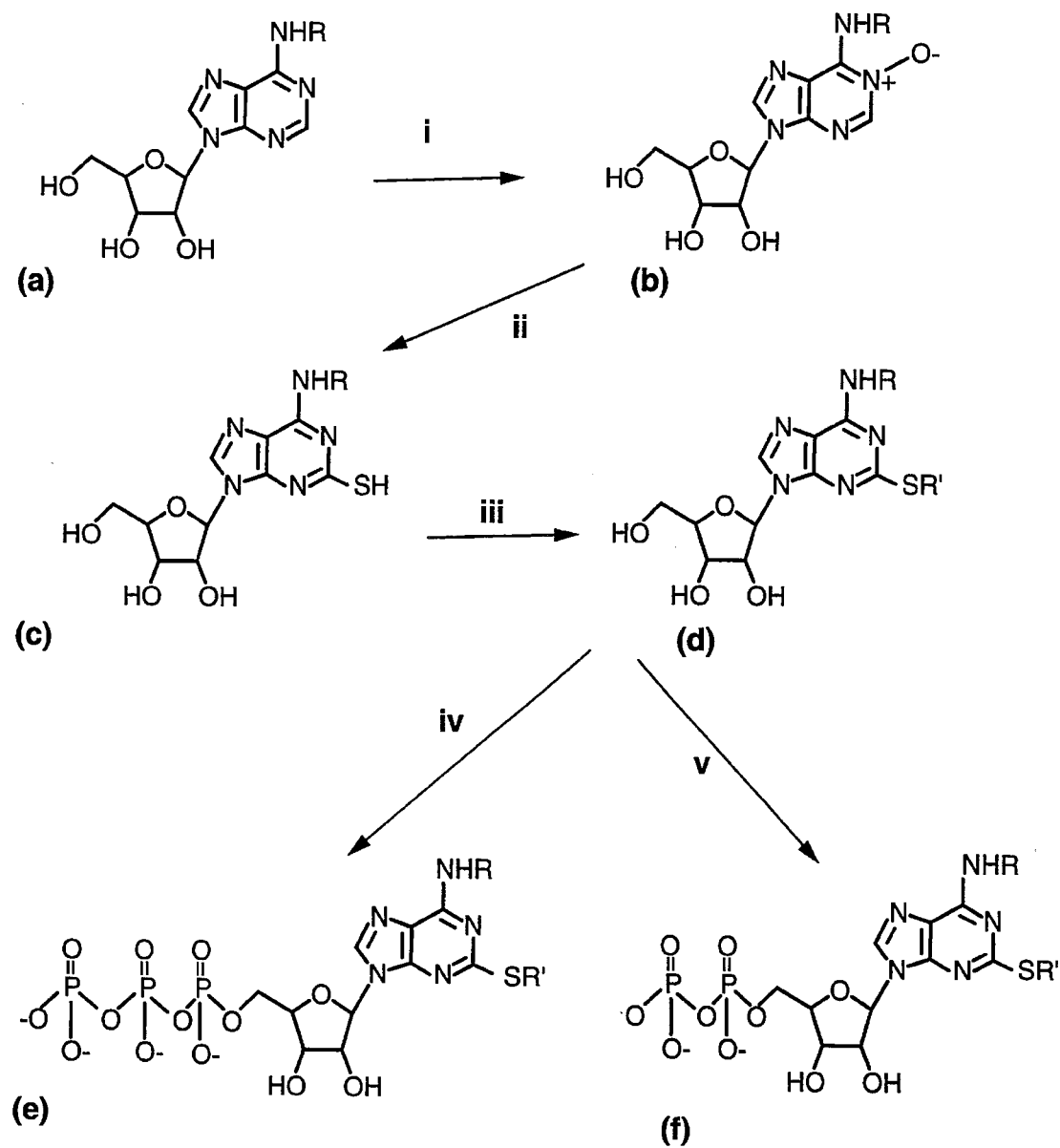
FIG. 1 is an outline of the procedure used to synthesize the 2-thioether- and $N^6$-methyl-ATP analogs of the present invention.

The present invention provides a series of new analogs of ATP that serve as selective agonists for $P_{2Y}$ and/or $P_{2X}$ receptors, which selectivity pertains to subclasses of the $P_{2Y}$ and $P_{2X}$ families. Additionally, the ATP analogs disclosed herein are metabolically stable. These nucleotides are derivatives of ATP that have been modified at one or a combination of the following sites: the purine ring ($C_2$-, $C_8$-, N1-, and $N^6$-substituents, and a uridine base instead of adenine), the ribose sugar group (2' and 3' positions), and the triphosphate group (lower phosphates, bridging oxygen substitution, and cyclization). The selectivity of these and related derivatives of ATP, as described hereinbelow, indicate to artisans of ordinary skill that the agonists of the $P_{2Y}$ and $P_{2X}$ receptors of the present invention have surprisingly enhanced potency and selectivity. Additionally, labeled derivatives (including those radioactively or fluorescently labeled) of the ATP analogs of the present invention are disclosed, and pharmaceutical compositions comprising either radiolabeled or nonradiolabeled ATP analogs, or combinations thereof, are disclosed as well. Finally, ATP analogs of the present invention may be used in treatments of, for example, septic shock and brain seizure, including anticonvulsive treatment, and of enhancement of learning and/or memory capabilities in individuals.

With reference to the ATP analogs having C2 substitutions, the progenitor 2-methylthio-ATP was previously known to have high affinity for $P_{2Y}$ receptors in binding and functional assays (see Boyer et al., supra; Cusack et al., *Nucleos. & Nucleot.*, 10, 1019–1028 (1991)). The progenitor compound was reported by Jacobson et al. *(Nucleos. & Nucleot.*, 10, 1029–1038 (1991)) to be susceptible to ecto-nucleotidases and therefore not acceptable as a putative pharmaceutical ingredient. Jacobson et al. also found that elongation of the side chain of 2-alkylthio ATP derivatives did resolve the metabolic stability problem. However, until the discovery of the present invention, no derivative was identified that had both the metabolic stability and the selectivity as demonstrated herein.

Overall, the present invention is directed to a compound of the formula

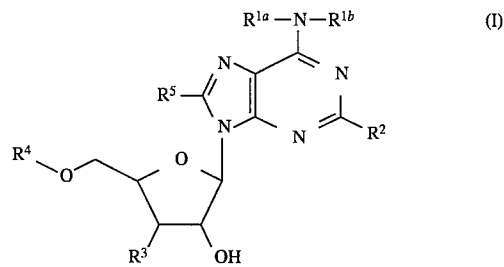

(I)

wherein $R^{1a}$ and $R^{1b}$ are the same or different and are hydrogen, ($C_1$–$C_7$)alkyl, ($C_1$–$C_7$)alkylphenyl, or ($C_5$–$C_{10}$)aryl ($C_1$–$C_7$)alkyl; $R^2$ is selected from the group consisting of S-($C_1$–$C_{11}$)alkyl, S-($C_1$–$C_7$)alkenyl, S-($C_1$–$C_7$)alkylcyano, S-($C_3$–$C_7$)cycloalkyl, S-phenyl, S-($C_1$–$C_3$) alkylphenyl, S-($C_1$–$C_7$)alkylamino, S-($C_1$–$C_7$)alkylthio ($C_1$–$C_7$)alkyl, S-($C_1$–$C_7$)alkylthiocyanato, S-($C_1$–$C_3$)alkylaminophenyl, S-($C_1$–$C_3$)alkylaminophenyl, S-($C_1$–$C_3$) alkylnitrophenyl, and hydrogen; $R^3$ is selected from the group consisting of ($C_1$–$C_7$)alkyl, ($C_1$–$C_7$)alkylamino, ($C_5$–$C_{10}$)aryl, ($C_5$–$C_{10}$)arylamino, amino, amido, and hydroxyl; $R^4$ is monophosphate, diphosphate, or triphosphate; and $R^5$ is selected from the group consisting of bromo, fluoro, chloro, amino($C_1$–$C_7$)alkylamino, or hydrogen;

provided that when R3 is hydroxyl, then at least one of $R^{1a}$, $R^{1b}$, R2, and $R^5$ is not hydrogen; and further provided that when R4 is triphosphate, $R^3$ is hydroxyl and $R^5$ is hydrogen. The alkyl and alkenyl groups are linear or branched.

Preferred compounds of the present invention include those that are described by formula (I), wherein $R^{1a}$ and $R^{1b}$ are the same or different and are hydrogen or methyl; $R^2$ is selected from the group consisting of S-($C_1$-$C_{11}$)alkyl, S-($C_1$-$C_7$)alkenyl, S-($C_1$-$C_7$)alkylcyano, S-($C_3$-$C_7$) cycloalkyl, S-phenyl, S-($C_1$-$C_3$)alkylphenyl, S-($C_1$-$C_3$) alkylaminophenyl, and S-($C_1$-$C_3$) alkylnitrophenyl; $R^3$ is hydroxyl; $R^4$ is monophosphate or diphosphate; and $R^5$ is hydrogen or amino($C_1$-$C_7$)alkyl amino.

Preferred compounds of the present invention further include those that are described by formula (I), wherein $R^{1a}$ is hydrogen; $R^{1b}$ is methyl; $R^3$ is hydroxyl; and $R^5$ is hydrogen. Examples of preferred compounds that are described by this structure include $N^6$-Me-2-(5-hexenyl)-thio-ADP and $N^6$-Me-2-(5-hexenyl)-thio-ATP.

Preferred compounds of the present invention also include those described by formula (I), wherein $R^{1a}$ and $R^{1b}$ are hydrogen; $R^3$ is hydroxyl; and $R^5$ is hydrogen. Examples of preferred compounds that are described by this structure include 2-thiopentyl-AMP, 2-thiohexyl-AMP, 2-thioheptyl-AMP, 2-thiooctyl-AMP, 2-thiodecyl-AMP, 2-thioundecyl-AMP, 2-(ethylthioethyl)-AMP, 2-(5-hexenyl)thio-ADP, 2-(2-(p-nitrophenyl)ethyl)thio-ADP, 2-(6-cyanohexyl)thio-ADP, 2-aminophenylethylthio-ADP, 2-(5-hexenyl)thio-ATP, 2-(2-(p-nitrophenyl)ethyl)thio-ADP, 2-(6-cyanohexyl)thio-ATP, and 2-aminophenylethylthio-ATP. A more preferred compound described by this structure is 2-thiohexyl-AMP.

Preferred compounds of the present invention additionally include those that are described by formula (I), wherein $R^{1a}$ is hydrogen; $R^{1b}$ is ($C_5$-$C_{10}$)aryl($C_1$-$C_7$)alkyl; $R^3$ is hydroxyl; $R^4$ is diphosphate or triphosphate; and $R^5$ is hydrogen. Examples of preferred compounds that are described by this structure include $N^6$-phenylethyl-ADP, $N^6$-phenylethyl-ATP, $N^6$-methyl-ADP, $N^6$-methyl-ATP, $N^6$-benzyl-ADP, $N^6$-benzyl-ATP, $N^6$-Phenylpropyl-ADP, $N^6$-phenylpropyl-ATP, $N^6$-Phenylbutyl-ADP, and $N^6$-phenylbutyl-ATP. More preferred compounds selected from the preferred compounds described immediately above include those wherein $R^{1b}$ is benzyl($C_1$-$C_3$)alkyl or phenyl($C_1$-$C_3$)alkyl, $R^2$ is hydrogen, and $R^4$ is triphosphate, or wherein $R^{1b}$ is hydrogen, $R^2$ is ($C_1$-$C_7$)alkylthio or ($C_1$-$C_3$)alkylpenylthio, and $R^4$ triphosphate, wherein either or both of the aliphatic and aromatic moieties are substituted at any position with polar or nonpolar groups. Most preferred compounds selected from those listed immediately hereinabove is $N^6$-phenylethyl-ATP.

The present invention is also directed to a compound of the formula:

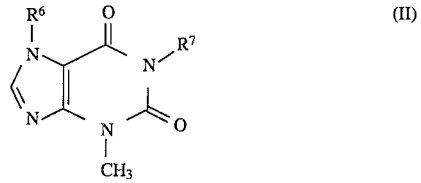

(II)

wherein $R^6$ and $R^7$ are different and are selected from the group consisting of ($C_1$-$C_3$)alkyltriphosphate and ($C_1$-$C_3$)alkyl, which moieties may be further substituted at any position with polar groups such as cyano, nitro, and the like, or nonpolar groups, such as alkyl or aryl groups.

Accordingly, formula (II) shown above represents certain xanthine phosphates modified at positions N3 and N7 with alkyl or alkyltriphosphate groups. Compounds of formula (II) are also referred to herein as ATP analogs.

Preferred compounds of the present invention include those that are described by formula (II), wherein $R^6$ is ethyltriphosphate and $R^7$ is methyl, or, more preferably, wherein $R^6$ is methyl and $R^7$ is ethyltriphosphate.

The present invention also provides a pharmaceutical composition comprising a pharmaceutically acceptable carrier and at least one compound of the present invention. Preferred pharmaceutical compositions include one or more of the preferred compounds of the present invention.

The present invention is further directed to a pharmaceutical composition comprising a pharmaceutically acceptable carrier and at least one compound selected from the group consisting of

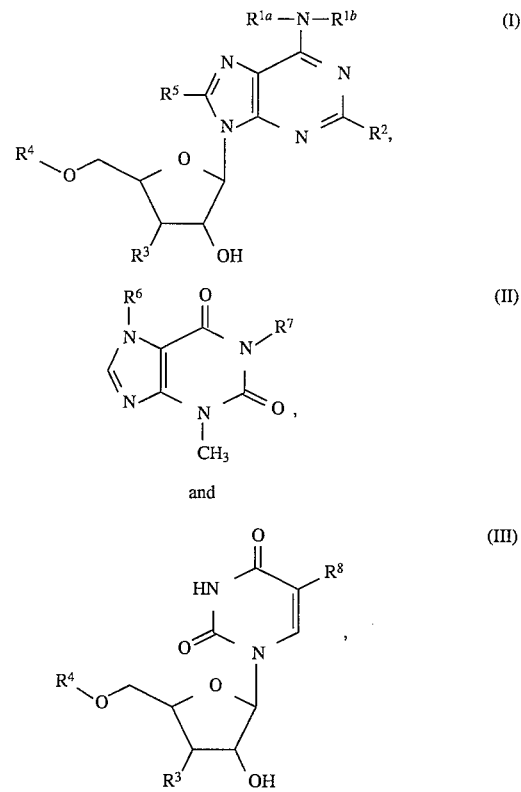

wherein $R^{1a}$ and $R_{1b}$ are the same or different and are hydrogen, ($C_1$-$C_7$)alkyl, ($C_1$-$C_7$)alkylphenyl, or phenyl ($C_1$-$C_7$)alkyl; $R^2$ is selected from the group consisting of S-($C_1$-$C_{11}$)alkyl, S-($C_1$-$C_7$)alkenyl, S-($C_1$-$C_7$)alkylcyano, S-($C_3$-$C_7$)cycloalkyl, S-phenyl, S-($C_1$-$C_3$)alkylphenyl, S-($C_1$-$C_7$)alkylamino, S-($C_1$-$C_7$)alkylthioalkyl, S-($C_1$-$C_7$) alkylthiocyanato, S-($C_1$-$C_3$)alkylaminophenyl, S-($C_1$-$C_3$) alkylnitrophenyl, and hydrogen; $R^3$ is selected from the group consisting of ($C_1$-$C_7$)alkyl, ($C_1$-$C_7$)alkyl amino, ($C_5$$C_{10}$)aryl, ($C_5$-$C_{10}$)arylamino, hydrogen, and hydroxyl; $R^4$ is monophosphate, diphosphate, or triphosphate; $R^5$ is selected from the group consisting of bromo, fluoro, chloro, amino($C_1$-$C_7$)alkyl amino, and hydrogen; $R^6$ and $R^7$ are different and selected from the group consisting of ($C_1$-$C_3$)alkyltriphosphate and ($C_1$-$C_3$)alkyl; and $R^8$ is selected from the group consisting of bromo, fluoro, chloro, and hydrogen. The alkyl and alkenyl groups are linear or branched. Compounds of the aforementioned formula used in the pharmaceutical composition of the present invention are defined herein as ATP analogs.

Preferred compositions of the present invention include compounds described by formula (I), wherein $R^{1a}$ and $R^{1b}$ are the same or different and are hydrogen or methyl; $R^2$ is selected from the group consisting of S-($C_1$-$C_{11}$)alkyl, S-($C_1$-$C_7$)alkenyl, S-($C_1$-$C_7$)alkylcyano, S($C_3$-$C_7$) cycloalkyl, S-phenyl, S-($C_1$-$C_3$)alkylphenyl, S-($C_1$-$C_3$) alkylaminophenyl, and S-($C_1$-$C_3$)alkylnitrophenyl; $R^3$ is hydroxyl; $R^4$ is monophosphate or diphosphate; and $R^5$ is hydrogen or amino($C_1$-$C_7$)alkyl amino.

Preferred compositions of the present invention further include compounds that are described by formula (I), wherein $R^{1a}$ is hydrogen; $R_{1b}$ is methyl; $R^3$ is hydroxyl; and $R^5$ is hydrogen. Examples of preferred compositions include those comprising $N^6$-Me-2-(5-hexenyl)thio-ADP and $N^6$-Me-2-(5-hexenyl)thio-ATP.

Preferred compositions of the present invention also include compounds that are described by formula (I), wherein $R^{1a}$ and $R^{1b}$ are hydrogen; $R^3$ is hydroxyl; and $R^5$ is hydrogen. Examples of preferred compositions include those comprising at least one of 2-thiopentyl-AMP, 2-thiohexyl-AMP, 2-thioheptyl-AMP, 2-thiooctyl-AMP, 2-thiodecyl-AMP, 2-thioundecyl-AMP, 2-(ethylthioethyl)-AMP, 2-(5-hexenyl)thio-ADP, 2-(2-(p-nitrophenyl)ethyl)thio-ADP, 2-(6-cyanohexyl)thio-ADP, 2-aminophenylethylthio-ADP, 2-(5-hexenyl)thio-ATP, 2-(2-(p-nitrophenyl)ethyl)thio-ATP, 2-(6-cyanohexyl)thio-ATP, and 2-aminophenylethylthio-ATP.

Preferred compositions of the present invention additionally include compounds that are described by formula (I), wherein $R^{1a}$ is hydrogen, $R^{1b}$ is phenylethyl; $R^3$ is hydroxyl; $R^4$ is diphosphate or triphosphate; and $R^5$ is hydrogen. Examples of preferred compositions include those comprising at least one of $N^6$-phenylethyl-ADP, $N^6$-phenylethyl-ATP, $N^6$-methyl-ADP, $N^6$-methyl-ATP, $N^6$-benzyl-ADP, $N^6$-benzyl-ATP, $N^6$-phenylpropyl-ADP, $N^6$-phenylpropyl-ATP, $N^6$-phenylbutyl-ADP, and $N^6$-phenylbutyl-ATP.

Preferred pharmaceutical compositions of the present invention also include those containing at least one compound described by formula (I), wherein $R^{1a}$, $R^{1b}$, and $R^5$, are each hydrogen; $R^2$ is hydroxyl; $R^3$ is selected from the group consisting of hydrogen, $(C_1-C_7)$alkyl, $(C_1-C_7)$alkylamino, $(C_5-C_{10})$aryl, and $(C_5-C_{10})$arylamino; and $R^4$ is triphosphate. More preferred pharmaceutical compositions of the present invention include those containing at least one of the preferred compounds described immediately above wherein $R^3$ is hydrogen, amino, acetylamino, p-hydroxyphenylpropionylamino, or benzylamino. Most preferred pharmaceutical compositions of the present invention include those containing the aforesaid preferred compound wherein $R^3$ is benzylamino.

Preferred pharmaceutical compositions of the present invention also include those containing at least one compound described by formula (I), wherein $R^3$ is selected from the group consisting of hydrogen, $(C_1-C_7)$alkyl, $(C_1-C_7)$alkyl-amino, $(C_5-C_{10})$aryl, and $(C_5-C_{10})$arylamino; $R^4$ is triphosphate; and $R^{1a}$, $R^{1b}$, $R^2$, and $R^5$ are each hydrogen. More preferred pharmaceutical compositions of the present invention include those containing at least one of: 3'-deoxy-ATP, 3'-amino-3'deoxy-ATP, 3'-acetylamino-3'-deoxy-ATP, 3'-(p-hydroxyphenylpropionylamino)-3'deoxy-ATP, and 3'-benzylamino-3'-deoxy-ATP. A yet more preferred pharmaceutical composition of the present invention is that including at least 3'-benzylamino-3'-deoxy-ATP.

Preferred pharmaceutical compositions of the present invention further include those containing at least one compound described by formula (II), wherein $R^6$ and $R^7$ are different and are methyl or ethyltriphosphate. A more preferred pharmaceutical composition of the present invention includes at least a compound of formula (II), wherein $R^6$ is methyl and f is ethyltriphosphate.

Preferred pharmaceutical compositions of the present invention also include those containing at least one compound described by formula (III), wherein $R^3$ is hydroxyl; $R^4$ is triphosphate; and $R^8$ is bromo, fluoro, or chloro. More preferred pharmaceutical compositions of the present invention include those containing at least one of 5-F-UTP or 5-Br-UTP.

The compounds of the present invention are synthesized using procedures well known in the art. Accordingly, substitution of structures I, II, and III may be at one or more sites. With reference to the C2-and $N^6$-substituted compounds described hereinabove (which include formula (I)) the synthesis procedures used are outlined in FIGS. 1 and 2, which are discussed in overview presently and by exemplification below. The methods discussed with reference to the C2-and $N^6$-substituted compounds are applicable generally to the synthesis of any of the other compounds disclosed herein, which may include other additional substitutions. Any method of synthesis known in the art may be used to effect the various steps shown in FIGS. 1–2, as well as those described regarding the other purine, ribose, and triphosphate substitutions described herein in the context of the present invention. The starting compound for synthesis of the C2-substituted compounds is preferably 2-thioadenosine, which can be synthesized according to Zimmet et al. (*Nucleos. & Nucleot.*, 12, 1–20 (1993)), as presented diagrammatically in FIG. 1 as steps i and ii. In essence, alkylation reactions (FIG. 1, step iii) are accomplished at the C2 position of 2-thioadenosine using a suitable alkyl-donating compound, such as an alkyl bromide or the like, in the presence of a suitable solution, such as a dilute NaOH/ MeOH solution at 20°–50° C. or triethylamine in dimethylformamide (DMF). A triphosphorylation reaction is next accomplished using a suitable method, such as that of Kovacs et al. (*Tetrahedron Lett.*, 29, 4525–4528 (1988))or Moffat (*Can. J. Chem.*, 42, 599 (1964)), as diagrammatically presented in FIG. 1 (step iv). Using these procedures, compounds of the present invention were obtained in 14–45% yield for all of the substituted ATP analogs disclosed herein, and variable amounts of the corresponding AMP derivatives were obtained as well (34%–69% yield). The resultant nucleotides are then purified using suitable means, such as on ion exchange resin columns (e.g., DEAE A-25 Sephadex)using a suitable buffered salt gradient, such as a 0 to 0.4M or a 0 to 0.6M $NH_4HCO_3$ buffer gradient. In some cases, further purification on HPLC or other suitable means is required.

A diphosphate derivative, such as 2-(5-hexenyl)thio-ADP, is synthesized by the same method described above, except that tributylammonium phosphate salt (used in the phosphorylation reaction of Kovacs et al. (supra) and Moffat (Supra)) is used for condensation with the phosphorodichloridate intermediate instead of the corresponding pyrophosphate salt. This reaction (step v of FIG. 1) gave rise not only to 2-(5-hexenyl)thio-ADP (~30% yield), but also to the corresponding monophosphate (~40% yield) and triphosphate (~5% yield) derivatives.

The synthesis of an aryl amino derivative is achieved as follows, using 2-(2-p-aminophenethyl)thio-ATP as an example. 2-(2-p-Aminophenethyl)thio-ATP was obtained quantitatively upon $PtO_2$-catalyzed hydrogenolysis of the corresponding nitro compound, 2-(2-p-nitrophenylethyl)thio-ATP, at room temperature overnight.

Figure 2:
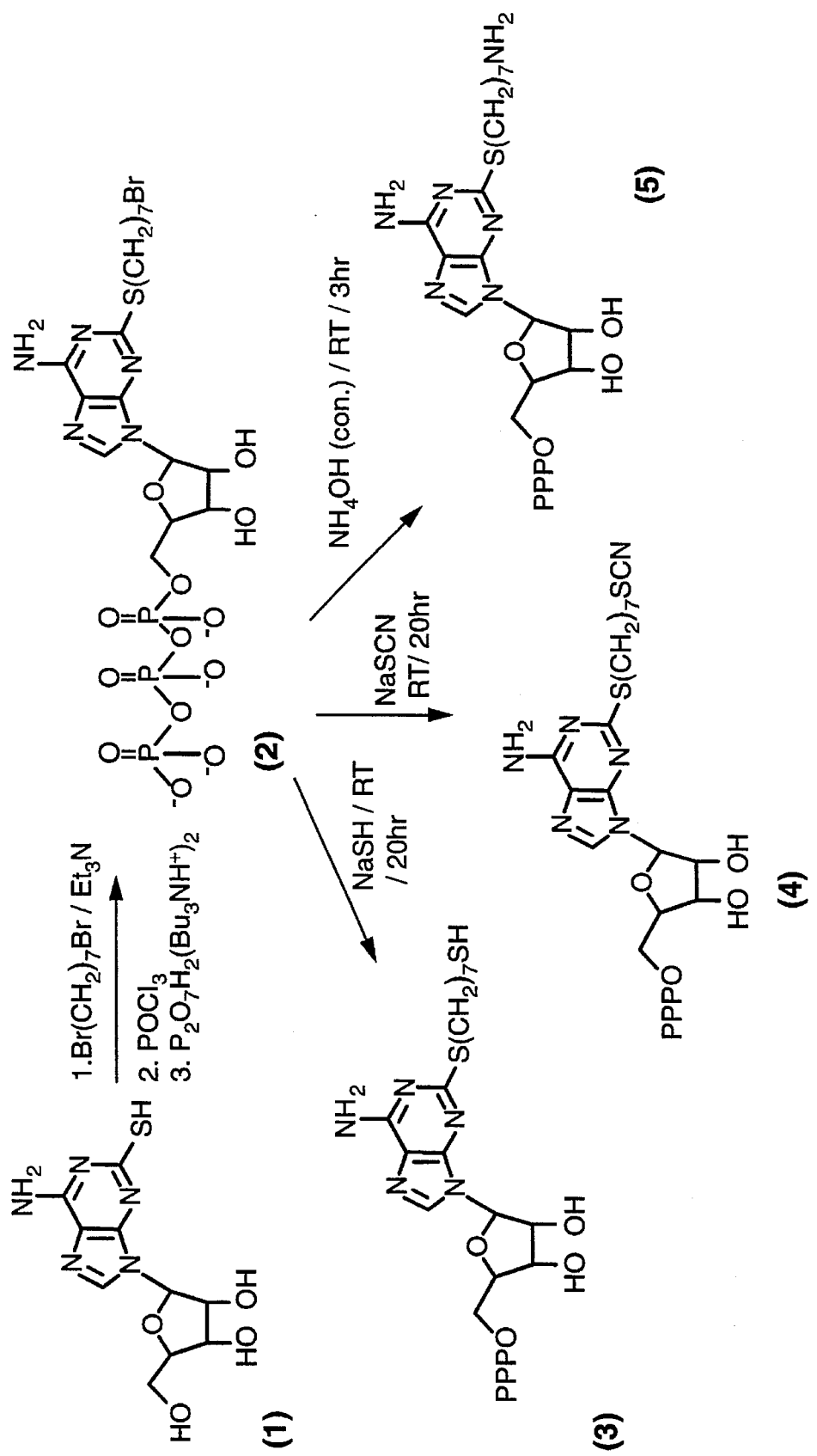
FIG. 2 is an outline of the procedure used to synthesize the terminally functionalized 2-thioalkyl ATP analogs of the present invention.

As shown in FIG. 2 in the first reaction recited therein, an aliphatic amine congener, 2-(7-aminoheptyl)-thio-ATP (compound (5)), was obtained in three steps from 2-thioadenosine, which was alkylated by 1,7-dibromoheptane in a dilute NaOH solution. The product, 2-(7-bromoheptyl-thio) adenosine (not shown), was triphosphorylated to provide an alkylating intermediate (compound (2)). This bromoalkyl triphosphate derivative was subsequently exposed to concentrated ammonia for 3 h at room temperature, yielding the desired amino product (compound (5)). Substitution of the bromide in compound (2) with hydrosulfide ion (by addition of an excess of NaSH at room temperature for 20 h) gave rise to the thio derivative, 2-(7-thioheptyl)thio-ATP (compound (3)). Treatment of compound (2) with aqueous sodium thiocyanate provided 2-[(7-thiocyanatoheptyl)thio]-ATP (compound (4)).

Synthesis of $N^6$-methyl-ATP analogs is diagrammatically displayed in FIG. 1 and was achieved as follows: $N^6$-methyladenosine, compound (A) in FIG. 1 where R is methyl, was N-oxidized by m-chloroperbenzoic acid in acetic acid, using methods well-known in the art. Introduction of a 2-thiol group was achieved in a two-step procedure: the base sensitive pyrimidine ring was opened via oxidation to the corresponding oxime by a short reflux in NaOH solution (step i), followed by reaction with $CS_2$, ring closure and N-oxide reduction, done under high temperature and pressure conditions (step ii), as described by Kikugawa et al. (*Chem. Pharm. Bull.*, 25, 1959–1969 (1977)). $N^6$-Methyl-2-thioadenosine, compound (C) where R is methyl, can be alkylated using appropriate alkyl-donating compounds, such as 1-hexenyl-6-bromide, and using suitable buffers, such as DMF in the presence of $Et_3N$ at room temperature. Accordingly, compound (D) where R is methyl and R' is 5-hexenyl, was synthesized, which was then phosphorylated (step iv) to give rise to both the homologous triphosphate (compound (E)), and monophosphate (compound not shown) products in 30% and 34% yield, respectively.

The synthesis and biochemical characterization of representative examples of all the classes of ATP analogs of the present invention, both those first disclosed herein and those first used in a pharmaceutical composition and method of treatment, are provided hereinbelow in Example 2.

It is appreciated that any of the ATP analogs, including all adenosine-, uracil- and xanthine-derivatives, can be labelled in a suitable manner, using any suitable label such as fluorescent dyes or radioactive isotopes. Methods for labelling are well known in the art. Accordingly, ATP analogs prepared with a radioactive label such as the isotopes $^3H$ $^{14}C$ $^{32}P$ $^{33}P$ and $^{125}I$, using methods well known in the art, is contemplated to be within the scope of the present invention. For example, any of the phosphorylation reactions can incorporate $^{32}P$ or $^{33}P$, resulting in substituting one or more of the phosphate groups in the phosphorylated species. Alternatively, any analog having a benzene ring, such as those including a 2-5-$(CH_2)_2$-p-aminophenyl group, can iodinate such a species with $^{125}I$ using standard methods. Similarly, fluorescein or rhodamine can be attached covalently to the inventive compounds using conventional methods. Such labeled species have utility for diagnostic procedures involving the activity of the $P_{2X}$ and $P_{2Y}$ receptors and conditions or diseases involved with such receptors.

The compounds of the present invention, such as 2-alkylthio-ATP analogs, are not only highly potent at $P_{2Y}$ receptors, but have also been shown to resist degradation by nucleotidases (Zimmet et al, supra). Accordingly, this property greatly enhances the utility of suitable compounds such as 2-(6-cyanohexylthio)-ATP as selective pharmacological tools. Because these compounds are of nanomolar potency at turkey erythrocyte $P_{2Y}$-receptors, they can be used as molecular probes for ATP receptors. Such probes, potentially including radioligands, fluorescent probes, immobilized ligands for affinity chromatography, affinity labels, and covalently reactive ligands could be obtained using a functionalized congener approach, as has been demonstrated for other classes of purine receptors (Jacobson et al. (1991), supra). Suitable compounds, such as 8-(6-aminohexylamino)-ATP, which contain an amino group linked via a chain at the 8-position, may serve as the basis for functionalized congeners selective for $P_{2Y}$ receptors such as occur in the rabbit aorta. Other suitable compounds, such as 3'-amino-3'-deoxy-ATP, which contain an amino group on the ribose, may serve as the basis for functionalized congeners active at $P_{2X}$ receptors in the guinea pig bladder and at $P_{2Y}$ receptors in the rabbit aorta. The compounds of the present invention have been demonstrated to have particular activities at different $P_2$ receptors, even to the extent of specificity to sub-type receptors within the $P_{2X}$ and $P_{2Y}$ classes. It is intended that such specificity provides a requisite characteristic needed for the utility of the disclosed compounds as pharmacological agents.

The present invention also provides a pharmaceutical composition comprising a pharmaceutically acceptable carrier and an amount of the active ingredient sufficient to reverse or prevent the bad effects of septic shock or brain seizures, for example. The carrier may be any of those conventionally used and is limited only by chemico-physical considerations, such as solubility and lack of reactivity with the compound, and by the route of administration. It will be appreciated by one of ordinary skill in the art that, in addition to the more specifically described pharmaceutical compositions, the compounds of the present invention may be formulated as inclusion complexes, such as cyclodextrin inclusion complexes, or liposomes.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

The choice of excipient will be determined in part by the particular compound of the present invention chosen, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Injectable formulations are among those formulations that are preferred in accordance with the present inventive methods. The requirements for effective pharmaceutical carriers for injectable compositions are well known to those of ordinary skill in the art (see *Pharmaceutics and Pharmacy Practice*, J. B. Lippincott Company, Philadelphia, Pa., Banker and Chalmers, eds., pages 238–250, (1982), and *ASHP Handbook on Injectable Drugs*, Toissel, 4th ed., pages 622–630 (1986)). It is preferred that such injectable compositions be administered intravenously.

Topical formulations, including those that are useful for transdermal drug release, are well-known to those of skill in the art and are suitable in the context of the present invention for application to skin.

Formulations suitable for oral administration can consist of (a)liquid solutions, such as an effective amount of the compound dissolved in diluents, such as water, saline, or orange juice; (b)capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the present invention, alone or in combination with other suitable components, can be made into aerosol formulations to be administered via inhalation. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Formulations suitable for parenteral administration include aqueous and non-aqueous, isotonic sterile injection solutions. Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds useful in the present inventive compositions may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Another aspect of the present invention involves a method for the selective activation of $P_{2X}$ or $P_{2Y}$ receptors, or subclasses thereof, comprising contacting the receptor with an effective quantity of at least one of the aforesaid compounds or compositions of the instant invention, including, the 2-alkylthio derivatives of adenyl nucleotides, 8-(6-aminohexylamino)ATP, 2',3'-isopropylidene ATP, $N^6$-methylATP, 2'-deoxyATP, and 3'-benzylamino-3'-deoxy-ATP. As exemplified hereinbelow, $P_{2X}$ and $P_{2Y}$ receptor families each comprise differentially reactive components. For example, the $P_{2Y}$ receptors of the taenia coli are activated by $N^6$-methylATP at an equal level as if activated by ATP itself. However, the $P_{2Y}$ receptors of the aorta are significantly less activated by the $N^6$-methyl derivative and the mesenteric artery is not activated at concentrations of the $N^6$-methyl derivative as high as $10^{-5}$M. Accordingly, the receptors of these various tissues are believed to be different, either qualitatively or quantitatively or both (see data presented in table in Example 11). Similarly, 3'-deoxy-ATP differentially activates the $P_{2X}$ receptors of the saphenous artery (no effect), the vas deferens (equivalent to the effect of ATP), and the urinary bladder (less potent or equal to potency of ATP). Accordingly, agonists have been identified herein that activate one variety of $P_{2X}$ receptors, those of the vas deferens, for example, but have no effect or little effect on another variety of $P_{2X}$ receptor, those of the saphenous artery, and have no effect on $P_{2Y}$ receptors generally. The converse series of relationships, wherein a suitable agonist is able to effect one sub-class of $P_{2Y}$ receptor but have little or no effect on other sub-classes of $P_{2Y}$ receptors can also have little or no effect on $P_{2X}$ receptors (e.g., $N^6$-methyl- ATP). The contacting may be effected using any suitable means, including the use of pharmaceutical compositions in various formulations, as disclosed hereinabove and generally known in the art.

The present invention is also particularly directed to a method for the treatment of septic shock and brain seizures. This method comprises administering to an individual or animal an effective quantity of the present inventive pharmaceutical composition. The mode and amount of administration of the pharmaceutical composition is suitable to the particular disease or disorder to be treated, which aspects can be determined by artisans of ordinary skill. The mode used for the treatment of septic shock is not necessarily the same as for the treatment of brain seizures, and both localized and systemic forms of treatment may be used.

The present invention is further particularly directed to a method for the treatment of diabetes, which method comprises administering to an individual or animal an effective quantity of the pharmaceutical composition disclosed hereinabove. The present inventive compounds which are potent and/or selective for the $P_{2Y}$-receptors are particularly preferred for use in the treatment of diabetes. See Loubatieres-Mariani et al., *Drug Dev. Res.*, 31, 292 (1994).

One skilled in the art will appreciate that suitable methods of utilizing a compound and administering it to a mammal for the treatment of disease states, which would be useful in the method of the present invention, are available. Although more than one route can be used to administer a particular compound, a particular route can provide a more immediate and more effective reaction than another route. Accordingly, the described methods are merely exemplary and are in no way limiting.

The dose administered to an animal, particularly human and other mammals, in accordance with the present invention should be sufficient to effect the desired response. Such responses include reversal or prevention of the bad effects of septic shock or brain seizures, particularly inasmuch that the ATP analogs of the present invention are believed to have anticonvulsive activity. The compounds of the present invention are also useful for the enhancement of memory and learning capabilities when applied to an individual over a reasonable time frame. One skilled in the art will recognize that dosage will depend upon a variety of factors, including the age, species, condition or disease state, and body weight of the animal, as well as the source and extent of the disease condition in the animal. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the individual.

The present invention further provides a means to evaluate material, e.g., to determine whether such material includes particular $P_2$ receptors, by determining particularly whether any binding is made between such material, or more specifically, a sample thereof, and a suitable compound of the present invention. Such means includes a biochemical test or assay comprising providing one of the aforesaid inventive compounds that has been labeled with a suitable marker, such as a radioactive label or a fluorescent label as discussed hereinabove, contacting the sample with the radiolabeled compound under conditions suitable to effect binding between the labeled compound and a component of the sample, and, using methods known in the art, measuring the quantity of label associated with the sample, or the proportion of label that is bound versus free, thereby determining the degree to which such binding has occurred. Suitable samples include clinical samples, such as blood or tissue, which samples can be evaluated in situ or after being removed from the donor. Animals, including humans, can be suitably tested using this procedure.

The following examples further illustrate the preferred embodiments of the present invention and, of course, should not be construed as in any way limiting the scope of the invention.

EXAMPLE 1

This example sets forth the methods and materials used to prepare and characterize biochemically the compounds of the present invention.

Commercially-derived chemicals and materials: The following compounds were purchased from the Sigma Chemical Co. of St. Louis, Mo.: ATP, α,β-methyl-ATP, β,γ-methyl-ATP, AppNHp, ATPγS, ADPβS, 8-(6-aminohexylamino)-ATP, adenosine N1-oxide 5'-triphosphate, N1,$N^6$-etheno-ATP, 2'-deoxy-ATP, 3'-deoxy-ATP, 2',3'-dideoxy-ATP, 3'-amino-3'-deoxy-ATP. ADP and AMP were obtained from Boehringer-Mannheim (Indianapolis, Ind.). ATP-α-S ($S_p$-isomer) was obtained from Amersham International (Amersham, UK). 3-(4-Hydroxyphenyl) propionic acid N-succinimide ester was purchased from Pierce (Rockford, Ill.).

Analytical TLC plates and silica gel (230–400 mesh) were purchased from VWR (Bridgeport, N.J.). Silica gel 100 $C_{18}$-reverse phase was obtained from Fluka (Ronkonoma, N.Y.).

General non-aqueous alkylation procedure: A solution of 2-thioadenosine or $N^6$-Me-2-thioadenosine (0.3 mmol), and dry $Et_3N$ (1.5 equivalents) in dry dimethylformamide (2 ml) was stirred at room temperature for 0.5 h. Alkyl bromide (5 equivalents) was added and stirring continued for an additional 2.5 h. The reaction solution was cooled in an ice bath, and a small amount of water (ca. 1 ml) was added. The white precipitate was filtered, dried and chromatographed on a silica gel column ($CHCl_3$: MeOH 5:1). Final purification was accomplished by precipitating the product from $CHCl_3$: MeOH (5:1)solution upon treatment with ether.

Procedure for triphosphorylation:

The procedure for nucleoside 5'-triphosphate synthesis was adapted from Kovacs et al. (supra) and Moffat (supra). All triphosphorylation reactions were carried out in a three neck flask flame dried under $N_2$. Nucleosides and Proton Sponge® (Aldrich Chemical Co., Milwaukee, Wis.) were dried overnight in a vacuum oven. Anhydrous solvents were used (trimethyl phosphate, dimethylformamide). Phosphorous oxychloride was distilled and kept under $N_2$. For the triphosphorylation reactions, tri-n-butylammonium pyrophosphate (TBAPP) solution and triethylammonium bicarbonate (TEAB) buffer were prepared as follows:

TBAPP Solution: Sodium pyrophosphate decahydrate (6.69 g, 0.015 mol) in water (100 ml) was stirred at room temperature for 10 min until a clear solution was attained.

The latter was passed through a column of activated Dowex 50WX-8 200 mesh, H⁺form (40 ml wet resin, 720 meq.).

The column was washed with deionized water until neutral. The column eluate was collected in a flask (250 ml) containing tributylamine (7.14 ml, 0.03 mol) and EtOH (75 ml) stirring at 0° C. The solution became cloudy during elution and became clear when all of the free amine was consumed. Lyophilization yielded a viscous oil. The latter was dissolved in EtOH and evaporated under high vacuum (bath temperature 35°–40° C). The process was repeated three times using dry dimethylformamide (30 ml) as the solvent, resulting in a thick oil that was dissolved in dry dimethylformamide (30 ml) and stored cold over activated molecular sieves.

TEAB Buffer: A 1M solution was prepared by adding dry ice to a 1M triethylamine solution in a flask covered tightly by a balloon for ca. 2 h until the pH reached 7.5.

A typical procedure was as follows: A solution of $N^6$-Me-2-(5-hexenyl) adenosine (0.03 g, 0.076 mmol) and Proton Sponge® (0.024 g, 1.5 eq.) in trimethylphosphate (1 ml) was stirred for 10 min at 0° C. Phosphorous oxychloride was added dropwise (14 μl, 0.152 mmol) and the clear solution was stirred for two hours at 0° C. A mixture of $Bu_3N$ (75 μl) and 0.5M $(Bu_3NH^+)_2 P_2O_7H_2$ in dimethylformamide (1 ml) was added at once. After two min 0.2M TEAB solution (7.5 ml) was added and the clear solution was stirred at room temperature for 45 min. The latter was lyophilized overnight. TLC on a silica gel plate, using propanol:$H_2O$:28% $NH_4OH$ (11:2:7) as the eluent, indicated the disappearance of starting material and the formation of a polar product ($R_f$=0.3). The spot was typically intensely purple under UV light and dark brown in an $I_2$ chamber.

The semi-solid obtained after lyophilization was chromatographed at room temperature on a Sephadex DEAE-A25 column, which was swelled in 1M $NaHCO_3$ in the cold for 3 days (7×1.5 cm). The resin was washed with deionized water (75 ml), using a peristaltic pump, and loaded with the crude reaction residue dissolved in a minimal volume of water. The separation was monitored by UV detection (ISCO, UA-5) at 280 nm. A buffer gradient of 250 ml water to 250 ml 0.5M $NH_4HCO_3$ or 0–400 or 600 mM TEAB buffer in 1000 or 600 ml was applied and 5 ml fractions were collected. The relevant fractions were pooled and lyophilized twice to yield a white solid (when $NH_4HCO_3$ buffer was used) or "clear glass" product (when TEAB buffer was used).

Purification of nucleotides: Purification of nucleotides was achieved on DEAE-A25 Sephadex columns as described above. Following the ion-exchange chromatography and subsequent lyophilization, the product was taken up in a small volume of water. An analytical quantity of this solution was examined by HPLC to determine retention time and degree of separation from contaminants. When needed, final purification was done on a Hewlett Packard 1090 HPLC system using a semipreparative SynChropak RP-P-100 5 μ column (250×10 mm, SynChrom, Inc., Lafayette, Ind.) or an Alltech nucleoside 7μ column (Alltech Associates, Deerfield, Ill.), equipped with an Alltech Adsorbosphere HSC18 50 precolumn (20 mm). A linear gradient of 5–22% 0.1M triethylammonium acetate buffer (TEAA, pH=7-8) in acetonitrile, with a flow rate of 1 ml/min or 3 ml/min for the analytical and semipreparative columns, respectively, was effected for a total of 20 min per run. The purity of the nucleotides described below was evaluated on an analytical column in two different solvent systems as well. One solvent system (I) was 0.1 M TEAA:$CH_3CN$ 80:20 to 40:60 in 20 min. The other (II) was 60 mM ammonium phosphate and 5 mM tetrabutylammonium phosphate (TBAP) in 90% water / 10% methanol (A) and 5 mM TBAP in methanol (B). Peaks were detected by UV absorption at 254 or 260 nm using a Hewlett-Packard diode array detector. A concentration gradient from 25% B to 75% B in 8 min was applied. ATP derivatives were generally >91% pure.

Characterization of compounds of the present invention: All the compounds tested for biological activity were characterized by high performance liquid chromatography (HPLC), nuclear magnetic resonance (NMR), as well as high resolution fast atom bombardment (FAB) spectra, using methods well-known in the art. For assessment of the nucleotides via proton ($^1H$) NMR, a Varian GEMINI-300 FT-NMR spectrometer was used. Nucleotides were characterized also by $^{31}P$ NMR in $D_2O$ using $H_3PO_4$ as an external reference on a Varian-ASM 100 300-MHz spectrometer. Samples (pD ranged from 5 to 7) were treated with CHELEX-100 (Bio-Rad, Richmond Calif.) prior to spectral measurement. Synthetic intermediates and all final products were characterized on a Finnigan MAT mass spectrometer by chemical ionization mass spectrometry ($NH_3$) and high resolution mass spectrometry. Nucleotides were desorbed from a glycerol matrix under FAB (fast atom bombardment) conditions using 6 KV Xe atoms on a JEOL SX102 spectrometer.

EXAMPLE 2

This example sets forth further details of the synthesis of various compounds of the present invention, including intermediate species used in the synthesis of herein disclosed ATP analogs, and biochemical characterization thereof.

$N^6$-Methyladenosine $N^1$-oxide: A solution of $N^6$-methyladenosine (2 g, 6.7 mmol) and m-chloroperbenzoic acid (2.3 g, 13.4 mmol) in acetic acid (20 ml) was stirred at room temperature for two days. Water (20 ml) was added to the reaction mixture, and a resulting thick precipitate was removed by filtration and discarded. The filtrate was co-evaporated repeatedly with water under high vacuum, and the foamy residue was chromatographed on a silica gel column ($CHCl_3$: MeOH 2:1). The product was obtained as a white solid (mp 145° C., crystallization from EtOH) in 45% yield (0.9 g). $^1H$ NMR (DMSO)d: 8.62 (s, H-2), 8.55 (s, H-8), 5.88 (d, J=5.4 Hz, 1H, H-1), 4.51 ('t', J=5.1 Hz, 1H, H-2'), 4.15 ('t', J=4.5 Hz, 1H, H-3'), 3.94 (ABq, 1H, H-4'), 3.61 (ABdq, J=12, 4 Hz, 2H, H-5'), 3.46 (s, 3H, Me) ppm. MS (CI) m/e: 298 (MH⁺).

Anal. calc. for $C_{11}H_{15}N_5O_5$: C, 40.12; H, 4.59; N, 21.29. Found: C, 40.44; H, 5.34; N, 20.29.

$N^6$-Methyl-2-thioadenosine: Compound (B) of FIG. 1, where R is methyl, was converted to 5-amino-1-b-D-ribofuranosylimidazole-4-(N-methyl)carboxidoxime, by the adaptation of the method of Kikugawa et al. (supra) and was obtained in a quantitative yield as a yellowish oil. $^1H$ NMR ($CD_3OD$)d: 8.54 (s, 1H, H-2), 7.46 (s, 1H, OH), 5.56 (d, J=6.2 Hz, 1H, H-1'), 4.47 (t, J=5.9, 1H, H-2'), 4.23 (dd, J=5.6, 3.5 Hz, 1H, H-3'), 4.02 (dd, J=6.0, 3.0 Hz, 1H, H-4'), 3.75 (ABdq, J=12.0, 3.0 Hz, 2H, H-5'), 2.90 (s, 3H, Me) ppm. 5-Amino-1-b-D-ribofuranosylimidazole-4-(N-methyl) carboxidoxime is thermally unstable and was used immediately or kept at -80° C.

A heterogeneous solution of 5-amino-1-b-D-ribofuranosylimidazole-4-(N-methyl)carboxidoxime (0.7 g, 2.5 mmol) in MeOH-$H_2O$ -$CS_2$ (19–7–5.5 ml, respectively) was heated in a sealed tube at 120° C. for 5 h. After cooling, the solution was evaporated to dryness and the brownish residue was chromatographed on a silica gel column (CHCl$_3$: MeOH 2:1 and then MeOH). Final purification was achieved by dissolution of the product in CHCl$_3$:MeOH (2:1) and then treatment with ether. The product, N$^6$-methyl-2-thioadenosine, was obtained as a light yellowish solid (0.4 g, 51% yield, mp>230° C., triturated from ether). $^1$H NMR (CD$_3$OD)d: 8.14 (s, 1H, H-8), 5.85 (d, J=5.6 Hz, 1H, H-1'), 4.61 ('t', J=5.3 Hz, 1H, H-2'), 4.28 (dd, J=5.2, 3.6 Hz, 1H, H-3'), 4.12 ('t', 1H H-4')3.81 (ABdq, J=12.0, 2.5 Hz, 2H, H-5'), 3.31 (s, 3H, Me) ppm. MS (CI) m/e: 314 (MH$^+$). High resolution FAB (positive ions, glycerol matrix) calcd. for C$_{11}$H$_{16}$N$_5$O$_4$S (MH+): 314.0923. Found: 314.0936.

2-(5-Hexenylthio)adenosine hemihydrate: 2-Thioadenosine (0.2 g, 0.67 mmol) was dissolved in 0.25M NaOH (8 ml, 2 mmol). 6-Bromo-1-hexene (0.45 ml, 3.3 mmol) was added, and the solution was stirred at room temperature for 3 h. The reaction mixture was concentrated under reduced pressure (bath temp. 33° C.) and extracted with ether (2×2 ml). The aqueous phase was neutralized with 18% HCl and extracted with ethyl acetate (3×4 ml). The homogeneous product was obtained after drying and solvent removal as a yellowish solid (0.14 g, 55% yield, mp 94° C., trituration with ether). $^1$H NMR (CD$_3$OD)d: 8.16 (s, 1H, H-8), 5.91 (d, J=5.8 Hz, 1H, H-1'), 5.8 (dm, 1H, olefinic), 4.93 (ddd, J=11, 9.7, 1 Hz, 2H, olefinic), 4.72 ('t', 1H, J=5 Hz H-2'), 4.31 (m, 1H, H-3'), 4.11 (m, 1H, H-4'), 3.83 (m, 2H, H-5'), 3.16 (m, 2H, CH$_2$S), 2.10 (m, 2H, CH$_2$), 1.74 (m, 2H, CH$_2$), 1.56 (m, 2H, CH$_2$) ppm. Anal. calc. for C$_{16}$H$_{23}$N$_5$O$_4$S.0.5H$_2$O: C, 49.22; H, 6.20; N, 17.93. Found: C, 49.46; H, 5.99; N, 17.36.

N$^6$-Methyl-2-(5-hexenylthio)adenosine: Prepared according to the same procedure for 2-(5-hexenylthio)adenosine hemihydrate, the yield was 23% (mp >230° C.) after column purification (CHCl$_3$: MeOH, 9:1) and trituration with ether. $^1$H NMR (CD$_3$OD)d: characteristic N$^6$-Me resonance at 3.1 ppm (br. s). HRMS: calcd. for C$_{17}$H$_{24}$N$_5$O$_4$S; 395. 1611 found; 395. 1627.

2-(6-Cyanohexylthio)adenosine hemihydrate: This compound was prepared according to the general nonaqueous procedure recited in Example 1. A yield of 72% yield (97 mg) was realized. The product was obtained as a yellowish solid (mp 162° C., crystallized from EtOH/H$_2$). $^1$H NMR (CD$_3$OD)d: 8.17 (s, 1H, H-8), 5.92 (d, J=5.9 Hz, 1H, H-1'), 4.72 (t, J=5.6 Hz, 1H, H-2'), 4.31 (dd, J=4.8, 3.5 Hz, 1H, H-3'), 4.11 (ABq, 1H, H-4'), 3.79 (ABdq, J=11.4, 2.9 Hz, 2H, H-5'), 2.44 (t, J=6.9 Hz, 4H, CH$_2$CH$_2$), 1.76 ('t', 2H, CH$_2$), 1.65 ('t', 2H, CH$_2$), 1.51 (m, 4H, CH$_2$CH$_2$) ppm. MS (CI) m/e: 409 (MH$^+$). Anal. calc. for C$_{17}$H$_{24}$N$_6$O$_4$S.0.5H$_2$: C, 48.91; H, 6.04; N, 20.13. Found: C, 48.94; H, 5.86; N, 19.99.

2-[(2-p-Nitrophenethyl)thio]adenosine: This compound was prepared according to the general nonaqueous procedure recited in Example 1. A yield of 73% (0.23 g) was realized. The product was obtained as a yellowish solid (mp 186° C., crystallized from EtOH/H$_2$O). $^1$H NMR (CD$_3$OD)d: 8.21 (s, 1H, H-8), 8.16 (d, J=8.6 Hz, 2H, Ar), 7.57 (d, J=8.6 Hz, 2H, Ar), 5.98 (d, J=5.9 Hz, 1H, H-1'), 4.68 ('t', J=5.5 Hz, 1H, H-2'), 4.30 (dd, J=5.1, 3.4 Hz, 1H, H-3'), 4.12 (ABq, 1H, H-4'), 3.79 (ABdq, J=12.3, 2.9 Hz, 2H, H-5'), 3.43 (m, 2H, CH$_2$Ar), 3.18 (t, 2H, CH$_2$S) ppm. HRMS: calcd. for C$_{18}$H$_{20}$N$_6$O$_6$; 448. 1148, found; 448.1165.

N$^6$-Me-2-(5-hexenylthio)adenosine monophosphate monoammonium salt: This compound was prepared using the triphosphorylation procedure recited in Example 1. A 34% yield (13 mg) was obtained. $^1$H NMR (D$_2$) d: 8.52 (s, 1H, H-8), 6.16 (d, J=5.4 Hz, 1H, H-1'), 5.80 (m, 1H, vinylic), 3.79 (s, 3H, Me), 2.13 (m, 2H, CH$_2$), 1.79 (m, 2H, CH$_2$), 1.56 (m, 2H, CH$_2$). High resolution FAB: calcd. for C$_{17}$H$_{25}$N$_5$SO$_7$P: 474.121. Found: 474.1238 (M$^{-2}$+2H$^+$). Retention time: 8.6 min (98% purity) using solvent system II.

N$^6$-Me-2-(5-hexenylthio)adenosine 5'-triphosphate: This compound was synthesized using the triphosphorylation procedure recited in Example 1. A 30% yield of the tetraammonium salt was obtained, which eluted after the monophosphate. $^1$H NMR (D$_2$O) d: 8.34 (s, 1H, H-8), 6.11 (d, J=5.7 Hz, 1H, H-1'), 5.91 (m, 1H, vinylic), 5.05 (dd, J=7.5, 1.6 Hz, vinylic), 4.98 (dd, J=10.4, 1.6 Hz, 1H, vinylic)(H-2' is hidden by the water peak), 4.60 (t, J=4.3 Hz, 1H, H-3'), 4.38 (br. s, 1H, H-4'), 4.24 (m, 2H, H-5'), 3.23 (m, 2H, CH$_2$S), 3.11 (s, 3H, Me), 2.12 (q, J=7 Hz, 2H, CH$_2$), 1.78 (quintet, J=7 Hz, 2H, C$_2$), 1.56 (quintet, J=7 Hz, 2H, CH$_2$). $^{31}$P NMR d: −6.0 (br. s), −10.9 (d), −21.6 (br. s) ppm. High resolution FAB: calcd. for C$_{17}$H$_{27}$N$_5$SO$_{13}$P$_3$: 634.0539, found: 634.0554 (M$^{-4}$+3H$^+$). Retention time: 8.5 min (>98% purity) using solvent system I, 8.8 min (>98% purity) using solvent system II.

2 -(5 -Hexenylthio) adenosine 5'-diphosphate trisammonium salt: The reaction was carried out on 0.158 mmol of 2-(5-hexenylthio) adenosine hemihydrate following a procedure that is the same as that for triphosphorylation (as recited in Example 1) wherein 0.13 M (Bu$_3$NH$^+$)$_2$PO$_4$H in DMF (6.9 ml, 6 equivalents) was used instead of tris(tributylammonium)-pyrophosphate solution. TLC taken after work-up (silica gel plate; solvent system-propanol: 28% NH$_4$OH:H$_2$O 11:8:2) indicated the formation of three products (R$_f$=0.33, 0.5, 0.7) in addition to a small amount of starting material. Separation on Sephadex DEAE-A25 column applying 0–0.5M NH$_4$HCO$_3$ gradient (500 ml of each). Final separation was achieved on a semipreparative column applying a linear gradient of 0.1M TEAA (pH 8.3): CH$_3$CN 80:20 to 40:60 in 20 min (3 ml/min). Mono-, di- and triphosphate products were obtained in 38% (29.7 mg), 30% (28 mg) and 5% (5.4 mg) yields, respectively. $^1$H NMR of 2-(5-hexenylthio)-adenosine 5'-diphosphate trisammonium salt (D$_2$) d: 8.40 (s, 1H, H-8), 6.13 (d, J =5.4 Hz, 1H, H-1'), 4.62 (t, J =4.7 Hz, 1H, H-3'), 4.37 (m, 1H, H-4'), 4.21 (m, 2H, H-5') ppm. High res. FAB: calcd for C$_{16}$H$_{24}$O$_{10}$N$_5$P$_2$S: 540.0719. Found: 540.0728. Retention time: 8.2 min (86% purity) using solvent system I, 7.4 min (86% purity) using solvent system II.

NMR of 2-(5-hexenylthio)adenosine 5'-monophosphate diammonium salt: $^1$H NMR (D$_2$) d: 8.34 (s, 1H, H-8), 6.13 (d, J =5.4 Hz, 1H, H-1), 5.91 (dm, 1H, olefinic), 5.01 (dd, 3=11, 9.7 Hz, olefinic), 4.50 (t, J=4.5 Hz, 1H, H-3$^1$), 4.37 (br. s, 1H, H-4$^1$), 4.13 (m, 2H, H-5$^1$), 3.21 (m, 2H, CH$_2$S), 2.13 (q, J=7 Hz, 2H, CH$_2$), 1.77 (m, 2H, CH$_2$), 1.55 (m, 2H, CH$_2$) ppm. High Res. FAB: calcd. for C$_6$H$_{23}$O$_7$N$_5$PS: 460.1056. Found: 460.1052. Retention time: 9.17 min (>98% purity) using solvent system I, 7.43 min (>98% purity) using solvent system II.

NMR of 2-(5-hexenylthio)adenosine 5'-triphosphate tetraammonium salt: $^1$H NMR (D$_2$) d: 8.41 (S, 1H, H-8), 6.13 (d, J=5.7 Hz, 1H, H-1'), 4.64 (m, 1H, H-3'), 4.37 (m, 1H, H-4'), 4.24 (din, 2H, H-5'). High Res. FAB: calcd. for C$_{16}$H$_{25}$O$_{13}$N$_5$P$_3$S: 620.0382. Found: 620.0428. Retention time: 7.7 min (91% purity) using solvent system I, 7.4 min (>98% purity) using solvent system II. 2-(5-Hexenylthio) adenosine 5'-triphosphate was also synthesized by the triphosphorylation procedure recited in Example 1.

2[2-(p-Nitrophen)ethylthio]adenosine 5'-triphosphate tetraammonium salt: This compound was obtained using the triphosphorylation procedure recited in Example 1, beginning with 0.1 mmol nucleoside. Purification by ion exchange as above was achieved using a gradient of water and 0.6M $NH_4HCO_3$ (230 ml of each). The triphosphate product was obtained in 37% yield (27.6 mg). $^1$H NMR ($D_2$) d: 8.33 (s, 1H, H-8), 7.97 (d, J=8 Hz, 2H, Ar), 7.45 (d, J=8 Hz, 2H, Ar), 6.02 (d, J=5.9 Hz, 1H, H-1') (H-2' is hidden by the water peak), 4.60 (t, J=4.2 Hz, 1H, H-3'), 4.39 (br.m, 1H, H-4'), 4.24 (br.dm, 2H, H-5'), 3.50 (br.m, 2H, $CH_2$), 3.17 (br.dm, 2H, $CH_2$). $^{31}$P NMR ($D_2O$, $_9$D=6) D: −7.07 (br.s), −11.07 (d), −22.68 (br.s) ppm. High res. FAB: calcd. for $C_{18}H_{23}N_6O_{15}P_3S$: 687. 0082, found: 687.0070 ($MH_3^-$). Retention time: 8.0 min (84% purity) using solvent system I, 7.3 min (98% purity) using solvent system II.

The monophosphate analog, i.e., 2- [2-(p-nitrophen)ethylthio]adenosine 5'-monophosphate, was obtained in 35% yield (19.2 mg). $^1$H NMR ($D_2$) d: 8.42 (s, 1H, H-8), 7.99 (d, J=8.0 Hz, 2H, Ar), 7.49 (d, J=8.0 Hz, 2H, Ar), 6.03 (d, J=5.9 Hz, 1H, H-1'), 4.50 (m, 1H, H-3'), 4.35 (m, 1H, H-4'), 4.00 (t, J=4 Hz, 2H, H-5'), 3.57 (m, 2H, $CH_2$)3.22 (m, 2H, $CH_2$). High res. FAB: calcd. for $C_{18}H_{20}N_6O_9PS$: 527.0750, found: 527.0738. Retention time: 9.6 min (95% purity) using solvent system I, 7.3 min (95% purity) using solvent system II.

2-[2-(p-Aminophen)ethylthio]adenosine 5'-triphosphate tetraammonium salt: 2-[2-(p-Nitrophen)ethylthio]adenosine 5'-triphosphate (5 mg, 6.7 μmol) dissolved in 0.5 ml $H_2O$ was hydrogenated overnight at room temperature (60 psi) over $PtO_2$ catalyst. After removal of the catalyst by centrifugation, the product was purified by HPLC (retention time 6.5 min on a semipreparative column, using a linear gradient of TEAA:$CH_3CN$ 80:20 to 40:60 in 20 min) and obtained in a quantitative yield. $^1$H NMR ($D_2$) d: 8.34 (s, 1H, H-8), 7.14 (d, J=8.3 Hz, 2H, Ar), 6.77 (d, J=8.3 Hz, 2H, Ar), 6.05 (d, J=5.7 Hz, 1H, H-1') (H-2' is hidden by the water peak), 4.54 (t, J=4.2 Hz, 1H, H-3'), 4.39 (br.m, 1H, H-4'), 4.24 (br.dm, 2H, H-5'), 3.40 (br.m, 2H, $CH_2$), 2.96 (br.m, 2H, $CH_2$). High res. FAB: calcd. for $C_{18}H_{24}N_6O_{13}P_3S$: 657.0335, found: 657.0323 ($MH_3^-$).

2-(6-Cyanohexylthio)adenosine-5'-triphosphate tetraammonium salt: The reaction was carried out on 0.11 mmol of 2-(6-cyanohexylthio)adenosine hemihydrate by the triphosphorylation procedure recited in Example 1. A gradient of 0 to 0.5M aqueous $NH_4HCO_3$ (generated from 230 ml of each) was applied during chromatography to obtain the product in 14% yield (10.7 mg). $^1$H NMR ($D_2O$) d: 8.48 (br.s, 1H, H-8), 6.14 (d, J=5.8 Hz, 1H, H-1')(H-2' is hidden by the water peak), 4.58 (t, J=4.3 Hz, 1H, H-3'), 4.39 (s, 1H, H-4'), 4.25 (br.s, 2H, H-5'), 3.22 (ABddd, 2H, $CH_2S$), 2.47 (t, J=7 Hz, 2H, $CH_2$), 1.77 (t, J=7 Hz, 2H ,$CH_2$)1.66 (t, J=7 Hz, 2H, $CH_2$), 1.48 (m, 2H, $CH_2$) ppm. $^{31}$P NMR ($D_2O$, pD=5) d: −5.6 (d), −11.0 (d), −21.5 (t) ppm. High res. FAB: calcd. for $C_{17}H_{26}N_6O_{13}P_3S$: 647.0491. Found: 647.00493 ($M^{-4}+3H^+$). Retention time: 6.0 min (91% purity) using solvent system I, 6.2 min (98% purity) using solvent system II.

The monophosphate analog, 2-(6-cyanohexyl)thio-ATP, was obtained in 69% yield (39.6 mg). $^1$H NMR ($D_2O$) d: 8.46 (s, 1H, H-8), 6.12 (d, J=6 Hz, 1H, H-1'), 4.51 (m, 1H, H-3'), 4.35 (m, 1H, H-4'), 3.99 (m, 2H, H-5'), 3.22 (ddd, J=12.4, 5.9 Hz, 2H, $CH_2S$), 2.47 (t, J=7 Hz, 2H, $CH_2$), 1.76 (m, 2H, $CH_2$), 1.66 (m, 2H, $CH_2$), 1.48 (m, 4H, $CH_2CH_2$). $^{31}$P NMR ($D_2O$, pD=5) d: −7.4 ppm. High res. FAB: calcd. for $C_{17}H_{24}N_6O_7PS$: 487.1165, found: 487.1148 ($M^{-2}+H^+$). Retention time: 4.9 min (85% purity) using solvent system I, 6.1 min (87% purity) using solvent system II.

2-(7-Bromoheptylthio)adenosine: 2-Thioadenosine (0.2 g, 0.67 mmol) was dissolved in 0.25M NaOH (8 ml, 2 mmol). 1,7-Dibromoheptane (0.31 ml, 1.8 mmol) in EtOH (5 ml) was added, and the solution was stirred vigorously at room temperature for 3 h. The solution was concentrated in the rotary evaporator, and the remaining aqueous solution was extracted with ether (2×5 ml). The aqueous phase was neutralized with 1M HCl. MeOH was added as a cosolvent followed by evaporation (2×). The yellowish residue was chromatographed on a silica column using $CHCl_3$:MeOH, 5:1 as the eluent. The oily product was triturated with $CHCl_3$/ether leaving a white solid (0.104 g, 33% yield, mp 137° C.). $^1$H NMR ($CD_3OD$) d: 8.16 (s, 1H, H-8), 5.92 (d, J=5.7 Hz, 1H, H-1'), 4.72 (t, 1H, J=5.6 Hz, H-2'), 4.31 (dd, J=5.1,1.5 Hz, 1H, H-3'), 4.11 (dd, 1H, J=6.3,3.2 Hz, H-4'), 3.79 (ABdq, J=12.4,3, 2H, H-5'), 3.43 (t, J=7 Hz, 2H, $CH_2Br$), 3.15 (m, 2H, $CH_2S$), 1.74 (m, 4H, $(CH_2)_2$), 1.46 (m, 6H, $(CH_2)_3$) ppm. FAB (positive ions, glycerol matrix): 476, 478 (M+1). Anal. calcd. for $C_{17}H_{26}N_5O_4SBr$: C, 42.86; H, 5.50; N, 14.70. Found: C, 42.97; H, 5.52; N, 14.64.

2-(7-Bromoheptyl)thioadenosine-5'-triphosphate tetraammonium salt: The reaction was carried out on 0.11 mmol of 2-(7-Bromoheptyl) thioadenosine following the typical procedure. A TLC taken after concentrating the crude reaction mixture by lyophilization indicated the formation of product (silica gel, propanol:28% $NH_4OH$:$H_2O$, 11: 8:2, $R_f$=0.45) in almost quantitative yield. A gradient of 0 to 0.75M aqueous $NH_4HCO_3$ (generated from 500 ml of each) was applied during chromatography to obtain the product in 68% yield (53.2 mg). $^1$H NMR ($D_2O$) d: 8.37 (br.s, 1H, H-8), 6.11 (d, J=5.7 Hz, 1H, H-1'), 4.75 (br 't', 1H, H-2'), 4.56 (br 't', 1H, H-3'), 4.37(br.s, 1H, H-4'), 4.22 (br.s, 2H, H-5'), 3.44 (t, J=7 Hz, 2H, $CH_2Br$), 3.18 (m, 2H, $CH_2S$), 1.75 (m, 4H, $(CH_2)_2$), 1.36 (m, 6H, $(CH_2)_3$) ppm. High Res. FAB: calcd. for $C_{17}H_{28}N_5O_{13}BrP_3S$: 713.9801, 715.9782. Found: 713.9787, 715.9807($MH_3^-$). Retention time: 13.2 min (>98% purity) using solvent system I, 9.3 min using solvent system II.

2-(7-Aminoheptylthio)-adenosine-5'-triphosphate tetrakis-triethylammonium salt: 2-(7-Bromoheptylthio)-ATP (compound (2) in FIG. 2; 8.1 mg, 10 μmol) was dissolved in 28% $NH_4OH$ (0.5 ml) and stirred at room temperature for 3 h. The crude mixture was separated on a semipreparative HPLC column (retention time: 7.9 min using a linear gradient of TEAA: $CH_3CN$, 95:5 to 40:60 in 20 min). The product was obtained in 52% yield (5.6 after repeated lyophilizations. $^1$H NMR ($D_2O$) d: 8.35 (s, 1H, H-8), 6.11 (d, J=5.4 Hz, 1H, H-1') (H-2' is hidden by the water peak), 4.58 (br.s, J=5.4 Hz, 1H, H-3'), 4.40 (br.s, 1H, H-4'), 4.24 (br.s, 2H, H-5'), 3.21 (q, 26H, $CH_2S$+$Et_3N$), 2.94 (t, J=7 Hz, 2H, $CH_2NH_2$), 1.75 (t, J=7 Hz, 2H, $CH_2$), 1.62 (m, 2H, $CH_2$), 1.28 (t, J=7 Hz, 42H, $(CH_2)_3$+$Et_3N$) ppm. High Res. FAB: calcd. for $C_{17}H_{30}N_6P_3S$: 651.0804. Found: 651.0778 ($MH_3^-$). Retention time: 7.9 min (94% purity) using 0.1M TEAA:$CH_3CN$ 95:5-40:60 in 20 min, 5.1 min (87% purity) using solvent system II.

2-(7-Thioheptylthio)-adenosine-5'-triphosphate tetrakis-triethylammonium salt: 2-(7-Bromoheptylthio)-ATP (compound (2) in FIG. 2; 2 mg, 2.5 μmol ) was dissolved in a concentrated solution of NaSH (12 mg, in 0.3 ml $H_2$) and stirred at room temperature for 20 h. The crude mixture was separated on a semipreparative HPLC column, retention time: 13.0 min using a linear gradient of TEAA (pH 8.4):$CH_3CN$, 80:20 to 40:60 in 20 min. The product was obtained in 60% yield (1.7 mg) after repeated lyophilizations. $^1$H NMR ($D_2O$) d: 8.35 (s, 1H, H-8), 6.11 (d, J=5.4 Hz, 1H, H-1'), 4.61 (t, J=5.4 Hz, 1H, H-3'), 4.37 (br.t, 1H, H-4'), 4.24 (br.ABq, 2H, H-5'), 3.20 (br.s, 28H, $CH_2S$+$Et_3$), 2.62 (t, J=7 Hz, 2H, $CH_2SH$), 1.64 and 1.55 (each: m, 2H, $CH_2$), 1.28 (br.s, 42H, $(CH_2)_3$+$Et_3$) ppm. High Res. FAB: calcd. for $C_{17}H_{29}N_5)_{13}P_3S_2$: 668.0416. Found: 668.0421 (MH$_3^-$).

2-(7-Thiocyanatoheptylthio)-adenosine-5'-triphosphate tris-triethylammonium salt: 2-(7-Bromoheptylthio)-ATP (compound (2) in FIG. 2; 2 mg, 2.5 μmol) was dissolved in a concentrated solution of KSCN (20 mg, ~100 eq. in 0.3 ml H$_2$O). The solution was stirred at room temperature for 20 h. The crude reaction mixture was separated on a semi-preparative HPLC column. The product was obtained in 48% yield (1.2 mg) after three sequential lyophilizations. $^1$H NMR (D$_2$O) d: 8.40 (s, 1H, H-8), 6.13 (d, J=5.3 Hz, 1H, H-1'), 4.62 (br 't', 1H, H-3'), 4.39 (br.s, 1H, H-4'), 4.24 (m, 2H, H-5'), 3.20 (q, J=7 Hz, 18H, Et$_3$), 3.02 (m, 2H, CH$_2$S), 1.77(m, 5H, CH$_2$), 1.43 (m, 7H, CH$_2$), 1.28 (t, J=7 Hz, 27H, Et$_3$) ppm. High Res. FAB: calcd. for $C_{18}H_{28}N_6O_{13}P_3S_2$: 693.0369. Found: 693.0358. Retention time: 7.7min (>98% purity) using solvent system I.

3',5'-Cyclic-β,γ-methylene adenosine 5'-triphosphate: 3',5'-cyclic-AMP free acid (0.067 g, 0.2 mmol) was suspended in MeOH (15 ml) and water (7ml). Tributylamine was added (0.048 ml, 0.2 mmol) and the clear solution was stirred for 1.5 h at room temperature. The solvent was removed and the residue was dried under high vacuum. The latter was dissolved in dry DMF (5 ml) together with carbonyldiimidazole (0.173 g, 5 eq.)under N$_2$ atmosphere. The clear solution was stirred at room temperature for 43 h. Dry methanol (51 μl, 1, 8 eq.) was added and after 1 h a solution of methylene diphosphate tributylammonium salt in DMF (2 eq. in 3 ml) was added dropwise; a white precipitate was formed. The solution was stirred at room temperature for 24 h and then concentrated under vacuum. The solid residue was dissolved in a minimal amount of water and loaded on a DEAE-A25 Sephadex column (15×1.5 cm) applying a gradient of 0.05M to 0.5M NH$_4$HCO$_3$ (275 ml of each). The relevant fractions were pooled and lyophilized. Final purification by HPLC applying TEAA: acetonitrile gradient 95:5 to 78:22 in 20 min. Retention time of product : 8.6 min. 1H NMR (D$_2$O) d: 8.24 (s, 1H, H-8), 8.21 (s, 1H, H-2), 6.17(s, 1H, H-1'), 4.55 (d, J=2.0 Hz, 1H, H-2'), 4.47(m, 1H, H-3'), 4.31 (m, 3H, H-4'+H-5'), 2.01 (t, J=19.3 Hz, 2H, PCH$_2$P). FAB: 485 (M$^{-4}$+3H$^+$).

N$^6$-Methyl-adenosine 5'-triphosphate trisammonium salt: N$^6$-Me-adenosine hydrate (Research Biochemicals Int., Natick, Mass.) was dried in vacuo at 90° C. for 20 h. The reaction to form the triphosphate was carried out as described in Example 1 beginning with 0.3 mmol of the nucleoside. TLC using propanol:H$_2$:NH$_4$OH (11:2:7) indicated the formation of the 5'-triphosphate (R$_f$0.13) as the sole product. The product was isolated using a Sephadex DEAE A-25 column, eluting with a gradient of 0–0.65 M TEAB (500 ml of each). Further purification was achieved using HPLC applying a linear gradient of 0–30% acetonitrile in 0.05M NH$_4$HCO$_2$ in 15 min (retention time 6.6 min). $^{31}$P NMR (D$_2$O) d: −9.0 (br.s), −10.8 (s), −22.1 (br.s) ppm. FAB: 520 (M$^{-4}$+3H$^+$).

8-Bromoadenosine 5'-triphosphate trisammonium salt: The reaction to form the triphosphate from 8-bromoadenosine was carried out as described in Example 1 on a 0.14 mmol (nucleoside) scale. 8-Bromo ATP trisammonium salt was obtained in 66% yield (60.7 mg) after chromatography using 0–0.65M NH$_4$HCO$_3$ gradient (total volume was 600 ml). Retention time was 11.8 min using a linear gradient of TEAA: acetonitrile 95:5 to 78:22 in 20 min. $^1$H NMR (D$_2$O) d: 8.26 (s, 1H, H-2), 6.15 (d, 1H, J=6.2 Hz, H-1'), 5.25 (t, 1H, J=6.2 Hz, H-2'), 4.66 (m, 1H, H-3'), 4.3 (m, 3H, H-4', H-5') ppm. $^{31}$P NMR d: −10.55 (m), −13.68 (d, J=20 Hz), −25.1 ('t') ppm. High res. FAB for $C_{10}H_{14}O_{13}N_5$ (81 Br)P$_3$ and $C_{10}H_{14}O_{13}N_5$ (79 Br)P$_3$: calcd. 583.8984, 585.8966; found 583.8998, 585.8993 (M$^{-4}$+3H$^+$).

5-Fluorouridine 5'-triphosphate tris triethylammonium salt: To a solution of 5-fluorouridine (dried in a vacuum oven at 50° C. for 10 h, 0.05 g, 0.19 mmol) in trimethylphosphate (1.9 ml) was added Proton Sponge® (0.06 g, 0,275 mmol). After stirring for 15 min at 0° C., phosphorous oxychloride (distilled, 44 μl, 0.46 mmol) was added dropwise, and the mixture was stirred at 0° C. for two hours. A mixture of Bu$_3$N (0.188 ml) and (Bu$_3$NH$^+$)$_2$ P$_2$O$_7$H$_2^{-2}$ in dimethylformamide (0.5M, 2.5 ml, 1.25 mmol) was added at once, and after two min the reaction was quenched with TEAB solution (0.2M, 18.8 ml). The solution was stirred at room temperature for 45 min and then lyophilized to yield a semi-solid. TLC (on silica gel, propanol: H$_2$O: 28% NH$_4$OH 11: 2 : 7) indicated the formation of the triphosphate (R$_f$=0.12). The residue was applied to a Sephadex DEAE-A25 column, which was eluted using a linear gradient of 0–0.6M NH$_4$HCO$_3$ (300 ml of each), to obtain the mono- and triphosphate products. 5-Fluorouridine 5'-monophosphate monoammonium salt was obtained in 49% yield (34.5 mg). It was further purified by HPLC using a linear gradient of TEAA: acetonitrile 95:5 to 78:22 in 20 min. Retention time was 3.8 min. $^1$H NMR (D$_2$O) d: 8.15 (d, J=6.3 Hz, 1H, H-6), 5.95 (dd, J=4.4, 1.4 Hz, 1H, H-1'), 4.33 (quintet, 2H, H-2'+H-3'), 4.26 (m, 1H, H-4'), 4.08 (ABq split into q, 2H, H-5'). $^{31}$P NMR d: −9.49 (s). High res. FAB: calcd. for: $C_9H_{10}N_2O_9PF$: 341.0186, found: 341.0197. (M$^{-2}$+H$^+$). 5-Fluorouridine 5'-triphosphate trisammonium salt was obtained in 36% yield (39 mg). $^1$H NMR (D$_2$O) d: 8.12 (d, J=6.4 Hz, 1H, H-6), 5.97(dd, J=5, 1.5 Hz, H-1'), 4.45 ('t', J=5 Hz, 1H, H-2'), 4.38 ('t', J=5 Hz, 1H, H-3'), 4.26 (m, 3H, H-4'+H-5') ppm. $^{31}$P NMR (D$_2$O) d: −9.78 (m), −13.87(d, J=20 Hz), −24.92 (t, J=20 Hz). High Res. FAB: calcd. for $C_9H_{14}FN_2O_{15}P_3$: 501.9591, found: 501.9531 (M$^{-4}$+3H$^+$). Retention time was 4.5 min using a linear gradient of TEAA: acetonitrile from 95:5 to 78:22 in 20 min.

3'-Acetylamino-3'-deoxyadenosine 5'-triphosphate: 3'-Amino-3'-deoxyadenosine 5'-triphosphate (15 mg, 26 mmol) and potassium carbonate (21 mg, 0.13 mmol) were dissolved in 2 ml of water. Sodium sulfosuccinimidyl acetate (36 mg, 0.13 mmol; Pierce Chemical, Rockford, Ill.) in 0.2 ml of dimethylsulfoxide (DMSO) was added at 0° C., and the reaction was allowed to proceed at room temperature for twenty-four hours. The product was purified by repeated injections on HPLC using a Synchropak RP-100 column (1×25 cm) applying a linear gradient of acetonitrile 5–22% TEAA (0.85 %/min, flow rate 3 ml/min, t=8.5 min). The appropriate fractions were collected and lyophilized to dryness. The product was obtained as a triethylammonium salt (8.5 mg, 39 %). UV: l$_{max}$=259 nm. High resolution MS for $C_{12}H_{18}N_6O_{13}P_3$: calcd. 547. 0145, found 547.0170 (MH$_3^-$).

3'-[3-(p-Hydroxyphenyl)propionylamino]-3'-deoxyadenosine 5'-triphosphate: 3'-Amino-3'-deoxyadenosine 5'-triphosphate (6 mg, 11 mmol) and potassium carbonate (7.2 mg, 55 mmol.) were dissolved in 0.8 ml of water. 3-(4-Hydroxyphenyl) propionic acid N-hydroxysuccinimide ester (27 mg, 0.1 mmol) in 0.4 ml of DMSO was added at room temperature, and the mixture was stirred for 24 hours at room temperature. The product was purified by the procedure described for 3'-acetylamino-3'-deoxyadenosine 5'-triphosphate (above); t=14 min (4.3 mg obtained, 41% yield). UV: l$_{max}$=259 nm. High resolution MS for $C_{19}H_{24}N_6O_{14}P_3$: calcd. 653.0563, found 653.0596 (MH$_3^-$).

3'-N-Benzylamino-3'-deoxyadenosine 5'-triphosphate: 3'-Amino-3'-deoxyadenosine 5'-triphosphate (15 mg, 26 mmol) and potassium carbonate (20 mg) are dissolved in 2 ml of water. Excess benzaldehyde (0.5 ml) was added, and the mixture was stirred vigorously at room temperature.

After 4 hours, excess benzaldehyde was extracted with chloroform. The aqueous solution was cooled to 0° C., and 25 mg of sodium cyanoborohydride were added portion wise over 0.5 h, and the mixture was stirred for an additional two hours at 0° C. Reaction with benzaldehyde and reduction with NaBH$_3$CN were repeated twice to ensure higher yields of 3'-N-benzylamino-3'-deoxyadenosine 5'-triphosphate. The product was purified by the procedure described for compound 3'-acetylamino-3'-deoxyadenosine 5'-triphosphate (above), where t=13 min. The yield was 25 % of 3'-N-benzylamino-3'-deoxyadenosine 5'-triphosphate (triethylamine salt), based on unrecovered starting material (30% reisolated). The $^1$H NMR spectrum was consistent with the proposed structures. UV: $l_{max}$=259 nm. High resolution MS for $C_{17}H_{22}N_6O_{12}P_3$: calcd. 595.0551, found 595.0509 (MH$_3^-$).

3'-N-Benzylamino-3'-deoxyadenosine 5'-monophosphate: 3'-N-Benzylamino-3'-deoxyadenosine 5'-monophosphate was obtained by treating 3'-N-benzylamino-3'-deoxyadenosine 5'-triphosphate in a pH=4.5 formic acid solution at 100° C. for 4 h. FAB ([Pos]/nitrobenzyl alcohol matrix): m/z 438MH$_2^+$, 302MH$_2^+$-adenine, 136 adenineH$_2^+$. This fragmentation pattern was definitive proof that alkylation had occurred on the sugar moiety.

Figure 17A:
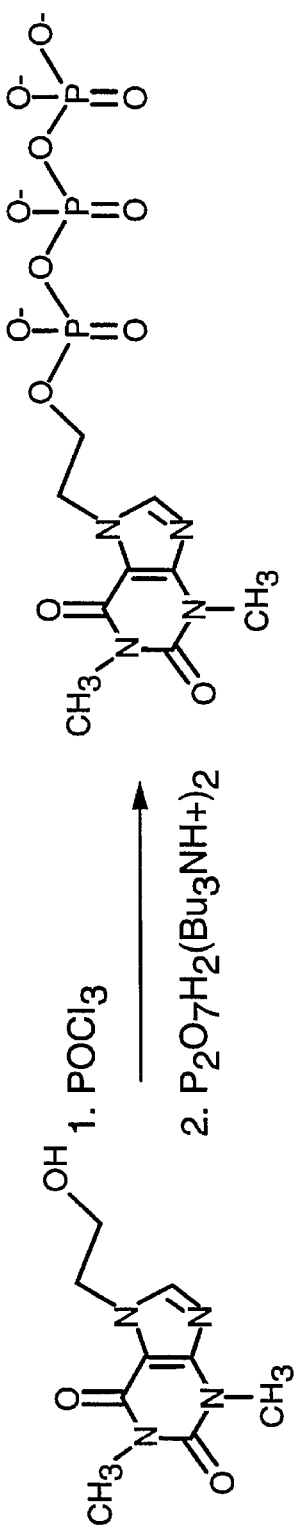
FIG. 17 is an outline of the procedure used to synthesize the xanthine phosphate ATP analogs of the present invention.

2',3'-Isopropylidene adenosine 5'-triphosphate tetraammonium salt: The reaction to prepare the 5'-triphosphate from 2',3'isopropylideneadenosine (Aldrich Chemical Co., St. Louis Mo.) was carried out as described in Example 1, on a 0.3 mmol (nucleoside) scale. The product was isolated by chromatography on a Sephadex DEAE-A25 column using a gradient of 0–0.5M NH$_4$HCO$_3$. Both mono and triphosphate derivatives were isolated. 2',3'-Isopropylidene AMP ammonium salt was obtained in 16% yield (22 mg) as well. Retention time was 10.2 min applying a linear gradient of TEAA: acetonitrile 95:5 to 60:40 in 20 min. $^1$H NMR (D$_2$O) d: 8.50 (s, 1H, H-8), 8.25 (s, 1H, H-2), 6.28 (d, J=3.4 Hz, 1H, H-1'), 5.41 (dd, J=6.1, 3.4 Hz, 1H, H-2'), 5.19 (dd, J=6.1, 2 Hz, 1H, H-3'), 4.64 (br.s, 1H, H-4'), 3.97 (dd, J=7.5, 3.9 Hz, 2H, H-5'), 1.67(s, 3H, Me), 1.45 (s, 3H, Me). FAB: 387 (M$^{-2}$+H$^+$). 2',3'-Isopropylidene ATP tetraammonium salt was obtained in 30% yield (55 mg). $^1$H NMR (D$_2$O) d: 8.48 (s, $^1$H, H-8), 8.24 (s, 1H, H-2), 6.29 (d, J=3.4 Hz, 1H, H-1'), 5.40 (dd, J=6,3.4 Hz, 1H, H-2'), 5.26 (dd, J=6,1.5 Hz, 1H, H-3'), (H-4' was hidden by the water peak), 4.20 (m, 2H, H-5'), 1.69, 1.44 (s, 3H, Me) ppm. $^{31}$P NMR d: −5.4 (br.s), −6.2 (br.s), −20.6 (br.s) ppm. High res. FAB for $C_{13}H_{19}N_5O_{13}P_3$: calcd. 546.0192, found: 546.0162 (M$^{-4}$+ 3H$^+$). Retention time was 3.4 min applying a linear gradient of TEAA:acetonitrile 80:20 to 40:60 in 20 min.

β-Hydroxyethyltheophylline triphosphate tetraammonium salt: The reaction to prepare the triphosphate species from β-hydroxyethyltheophylline (Aldrich Chemical Co., St. Louis, Mo.) was carried out as described in Example 1, and illustrated in FIG. 17A. The product was concentrated by lyophilization and separated on a Sephadex chromatography column using a 0 to 0.6M NH$_4$HCO$_3$ gradient. The yield was 90 mg (i.e., 84.5% of the starting material).

$^1$H NMR indicated the presence of the desired product. FAB indicated the expected mass of 463; FAB analysis also revealed minor yields of higher mass, i.e., 533 and 641. The $K_{0.5}$ of this compound, as determined by the procedures disclosed below in Example 3, was 26.9 μM.

Figure 17B:
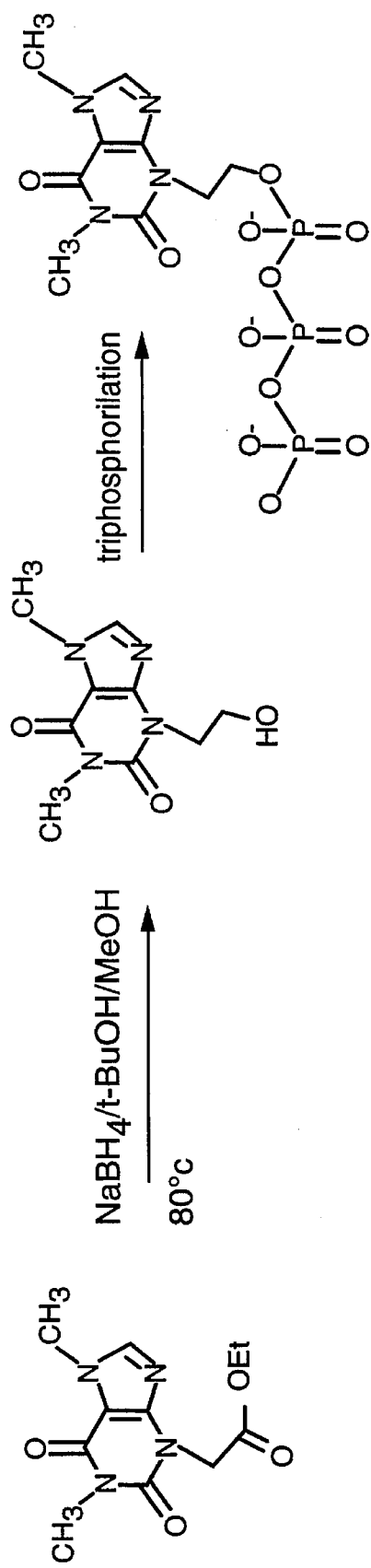

1-7-Dimethyl-3-(2-hydroxyethyl)xanthine triphosphate: The reaction for preparation of this compound is illustrated in FIG. 17B. The starting material for preparation the xanthine derivative triphosphate is 1,7-dimethyl-3-ethoxcarbonylethylxanthine (MW 266), which was prepared according to the procedure of Daly et al. (*Pharmacol.*, 42 309 (1991)). The starting material (25 mg; 0.094 mmol) of was dissolved in a solution of NaBH$_4$ in t-butanol/methanol, and allowed to react therein at 80° C. for 1.5 h, resulting in 1,7-dimethyl-3-(2-hydroxyethyl) xanthine as the main product. The solvent was evaporated under a stream of nitrogen. The residue was dissolved in a minimal amount of methanol and separated on a thin column. The product was obtained as a white solid; mass of 12 mg, 58% yield. Mass spectrometry showed a main peak at 285(M$^+$H$^+$) and a smaller peak at 242 (=H$_2$O).

The 1,7-dimethyl-3-(2-hydroxyethyl)xanthine was triphosphorylated according to the method disclosed in Example 1. FAB spectrum indicated the presence of the product 1,7-dimethyl-3-(2-hydroxyethyl)xanthine triphosphate, having a molecular weight of 463 (M$^{-1}$+H$^+$). HPLC chromatogram and $^1$H NMR indicated that impurities were present. The xanthine derivative triphosphate species was purified on HPLC using standard methods. The $K_{0.5}$ of this compound, as determined by the procedures disclosed below in Example 3, was 100 μM.

EXAMPLE 3

This example sets forth the methods used to test the compounds of the present invention for biological activity.

Phospholipase C activity: Stimulation of inositol phosphate formation by compounds of the present invention was measured in turkey erythrocyte membranes as described by Harden et al., supra and Boyer et al., supra. The $K_{0.5}$ values were averaged from 3–8 independently determined dose-response curves for each compound. Briefly, one ml of washed turkey erythrocytes was incubated in inositol-free medium (DMEM; Gibco) with 0.5–1 mCi of 2-[$^3$H]myo-inositol (20 Ci/mmol; American Radiolabeled Chemicals Inc., St. Louis, Mo.)for 18–24 h in a humidified atmosphere of 95% air 5% CO$_2$ at 37° C. Erythrocyte ghosts were prepared by rapid lysis in hypotonic buffer (5 mM sodium phosphate, pH 7.4, 5 mM MgCl$_2$, 1 mM EGTA) as described by Boyer et al., supra. Phospholipase C activity was measured in 25 μl of [$^3$H]inositol-labeled ghosts (≈175 μg of protein, 200–500,000 cpm/assay) in a medium containing 424 μM CaCl$_2$, 0.91 mM MgSO$_4$, 2 mM EGTA, 115 mM KCl, 5 mM KH$_2$PO$_4$, and 10 mM Hepes, pH 7.0. Assay (100 μl or 200 μl final volume) contained 1 μM GTPγS and the indicated concentrations of nucleotide analogs. Ghosts were incubated at 30° C. for 5 min, and total [$^3$H]inositol phosphates were quantitated after purification by anion exchange chromatography according to Harden et al. (supra) and Boyer et al. (supra).

Muscular relaxation/contraction: Relaxant responses mediated via P$_{2Y}$ receptors were examined in guinea pig taenia coli, rabbit aorta, and rabbit mesenteric artery, as described by Hoyle et al. (*Br. J. Pharmacol.*, 107, 367–374 (1992a)), Burnstock et al., (*Br. J. Pharmacol.*, 90, 383–391 (1987a)), and Rubino et al., (*Eur. J. Pharmacol.*, 212, 237–240 (1992)). Contractile responses mediated via P$_{2X}$ receptors were examined in the guinea pig urinary bladder and vas deferens, and rabbit saphenous artery, also using standard methods (see Hoyle et al., supra., 1992; Hoyle et al., *Br. J. Pharmacol.*, 99, 617–621 (1990); and Burnstock et al., *Br. J. Pharmacol.*, 90, 111–120 (1987b)).

EXAMPLE 4

This example illustrates the concentration-dependent stimulation of phospholipase C activity by 2-thioether analogs of ATP of the present invention.

Phospholipase C activity, in response to the presence of certain 2-thioether-ATP analogs, was assessed using the method recited in Example 3. The results of this set of assays are presented in the graph of FIG. 3, with reference to the following compounds: ATP (■); 2-methylthio-ATP (◇); (○); 2-hexylthio-ATP (Δ); 2-hexenylthio-(◇); 2-phenylethylthio-ATP (□); 2-cyclohexylthio-ATP (▽); 2-cyanohexylthio-ATP (●); and 2-(4-nitrophenylethyl)thio-ATP (▲). The average cpm of [$^3$H] inositol phosphates produced in the presence of 1 micromolar GTPγS alone was 400 cpm (0%). The maximal (100%) level of [$^3$H]inositol phosphates produced in the presence of GTPγS and adenine nucleotide analogs was at least 5000 cpm with all membranes tested. The data from different experiments were normalized by presenting each assay result as a percentage of maximum (100%) stimulation (y-axis), as a function of the negative log of (putative) agonist concentration (x-axis).

With the exception of the 7-aminoheptyl and 7-thioheptyl derivatives, recited above, respectively, the potency of the 2-alkylthio-substituted ATP analogs (namely, 2-hexylthio-ATP, 2-(5-hexenyl) thio-ATP, 2-phenylethylthio-ATP, 2-(2–4-nitrophenylethyl) thio-ATP, 2-(2–4aminophenylethyl)thio-ATP, 2-cyclohexylthio-ATP, 2-(6-cyanohexyl) thio-ATP, and 2-[(7-thiocyanatoheptyl)-thio]-ATP) to stimulate inositol lipid hydrolysis in turkey erythrocyte membranes was shown to be at least two orders of magnitude more potent ($K_{0.5}$ values=5–30 nM) than ATP (see the Table for comparative values). Most of these compounds were more potent than 2-chloro-ATP ($K_{0.5=72}$ nM). The thioether derivatives were also equiefficacious to ATP in the turkey erythrocyte membranes.

Figure 3:
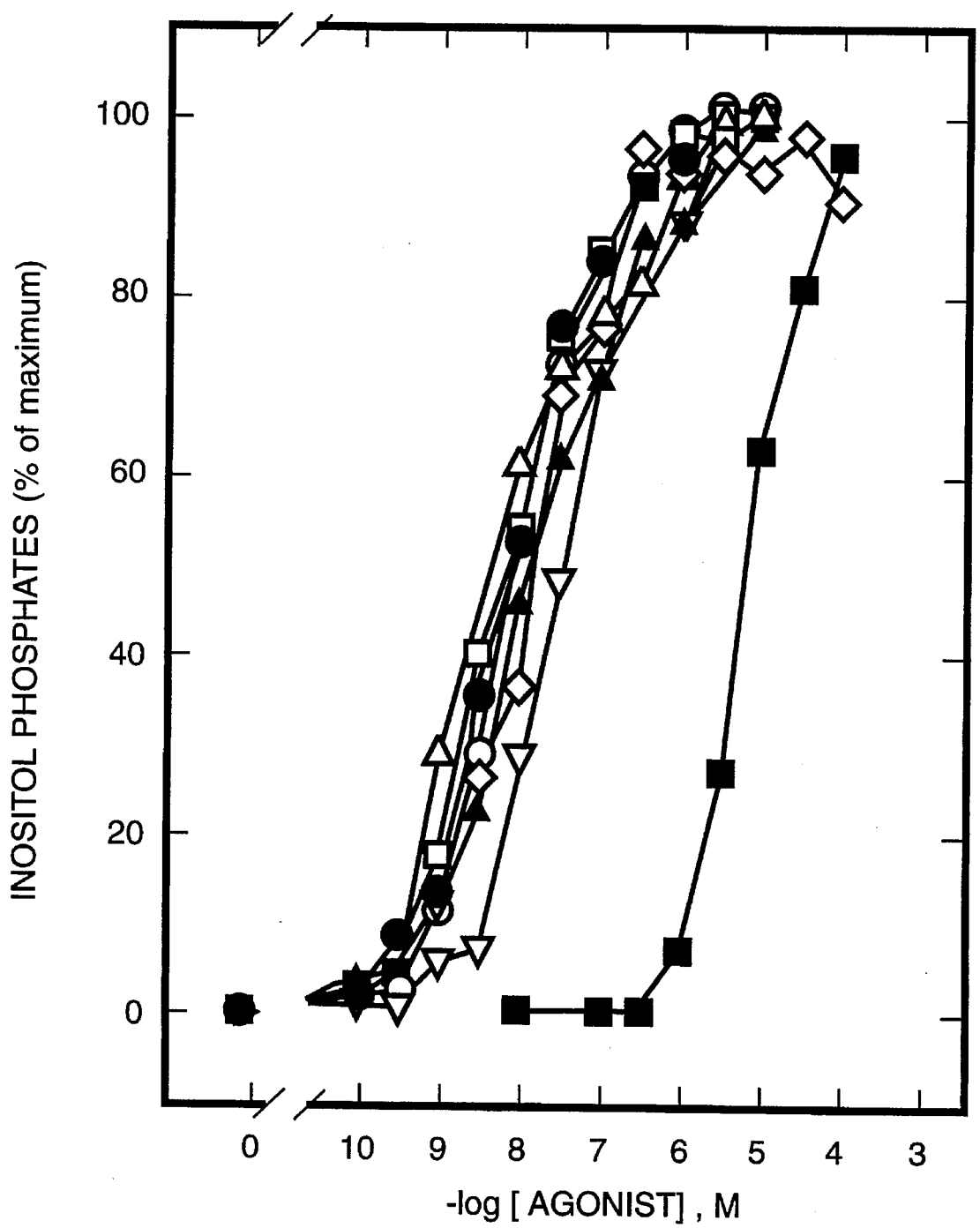
FIG. 3 is a graph that presents data directed at concentration-dependent stimulation of phospholipase C activity by 2-thioether-ATP analogs, wherein the abscissa is labeled "-log [Agonist], M" and the ordinate is labeled "Inositol Phosphates (% of Maximum)".

Because stimulation of turkey erythrocyte membranes to hydrolyze inositol lipids is mediated by $P_{2Y}$ receptors, the results displayed in FIG. 3 and elucidated above indicate that the 2-alkylthio-substituted ATP analogs of the present invention are agonists for the $P_{2Y}$ receptor.

EXAMPLE 5

This example illustrates the phospholipase C activity stimulated by 2-thioether analogs of ATP and ADP.

Phospholipase C activity in response to the presence of certain 2-thioether analogs of ATP and ADP was assessed using the method recited in Example 3. The results of this set of assays are presented in the graph of FIG. 4, with reference to the following compounds: ADP (■); ATP (□); 2-methylthio-ADP (●); 2-methylthio-ATP (○); 2-hexenylthio-ADP (▲); and 2-hexenylthio-ATP (Δ). [$^3$H]inositol phosphate accumulation in the presence of GTPγS alone was 200–400 cpm (0%). Maximal levels of [$^3$H]inositol phosphates accumulated in response to ADP and ATP analogs in the presence of GTPγS (100%) were identical within the same membrane preparation, with values ranging from 5000 to 9000 cpm. The data from different experiments were normalized by presenting each assay result as a percentage of maximum (100%) stimulation (y-axis), as a function of the negative log of (putative) agonist concentration (x-axis).

Figure 4:
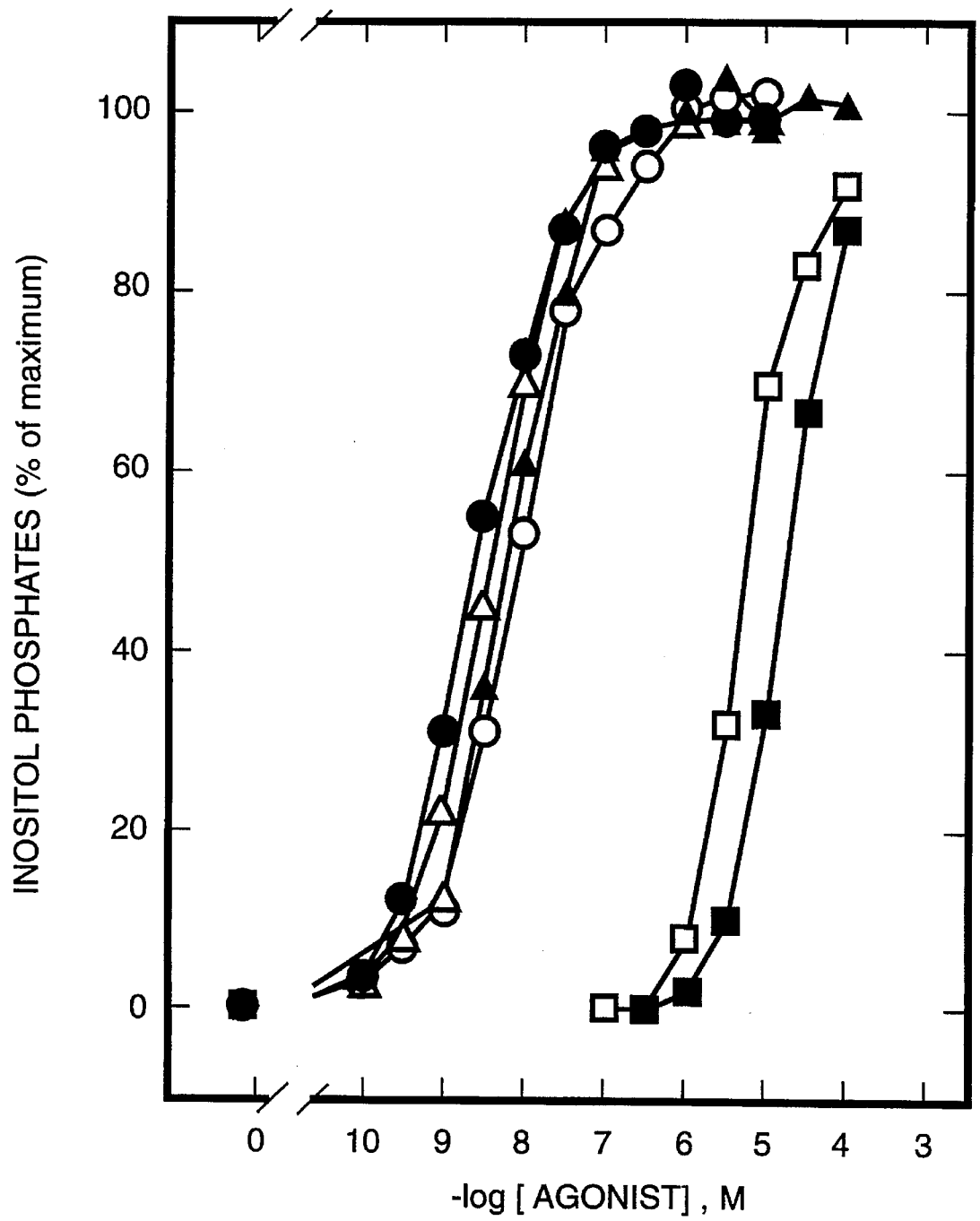
FIG. 4 is a graph that presents data directed at concentration-dependent stimulation of phospholipase C activity by thioether analogs of ATP and ADP, wherein the abscissa is labeled "-log [Agonist], M" and the ordinate is labeled "Inositol Phosphates (% of Maximum)".

The data presented in FIG. 4 show that the erythrocyte receptor was activated equally well by ATP and ADP, which stimulated 50% activity ($K_{0.5}$) at $10^{-5}$ and $10^{-5.5}$M concentrations. The 2-thioether analogs stimulated the erythrocyte receptors substantially better, without consequence of whether the analog was di- or triphosphorylated. For example, 2-methylthio-ATP and 2-methyl-ADP stimulated 50% activity ($K_{0.5}$) at 8 nM and 6 nM, respectively. Longer chain analogs demonstrated similar equipotency, e.g., 2-(5-hexenylthio)-ATP had a $K_{0.5}$ of 10 nM and the corresponding ADP analog had a $K_{0.5}$ of 4 nM.

Therefore, triphosphates are not necessarily more potent activators of the erythrocyte $P_{2Y}$ receptor than their corresponding ADP analogs.

EXAMPLE 6

This example illustrates the phospholipase C activity stimulated by 2-thioether analogs of AMP and ATP.

Phospholipase C activity was assessed using the method recited in Example 3. The results of this set of assays are presented in the graph of FIG. 5, with reference to the following compounds: AMP (□); ATP (■); 2-cyanohexylthio-AMP (○); 2-cyanohexylthio-ATP (●); 2-(4-nitrophenylethyl)thio-AMP (Δ); 2-(4-nitrophenylethyl)-thio-ATP (▲). [$^3$H]inositol phosphate accumulation in the presence of 1 μM GTPγS alone was 200 cpm (0%). Maximal levels (100%) of [$^3$H]inositol phosphate accumulation in the presence of GTPγS and a maximal concentration of agonist, e.g., 1 μM 2-cyanohexylthio-ATP, was 6000 cpm. The data from different experiments were normalized by presenting each data point as a percentage of maximal (100%) stimulation (y-axis), as a function of the negative log of (putative) agonist concentration (x-axis).

These data show that the monophosphate 2-thioether analogs, such as 2-(6-cyanohexylthio)-AMP, exhibited $K_{0.5}$ values of 37 μM, for example, and therefore must be considered full agonists. Even so, such AMP derivatives are considerably less potent than the corresponding ATP analogs, such as 2-(6-cyanohexyl) thio-ATP, which has a $K_{0.5}$ of about 10 nM, i.e., about three orders of magnitude more potent. The 2-hexenylthio monophosphate derivative, however, was only 33-fold less potent at stimulating turkey erythrocyte $P_{2Y}$ receptors than the corresponding triphosphate.

Figure 5:
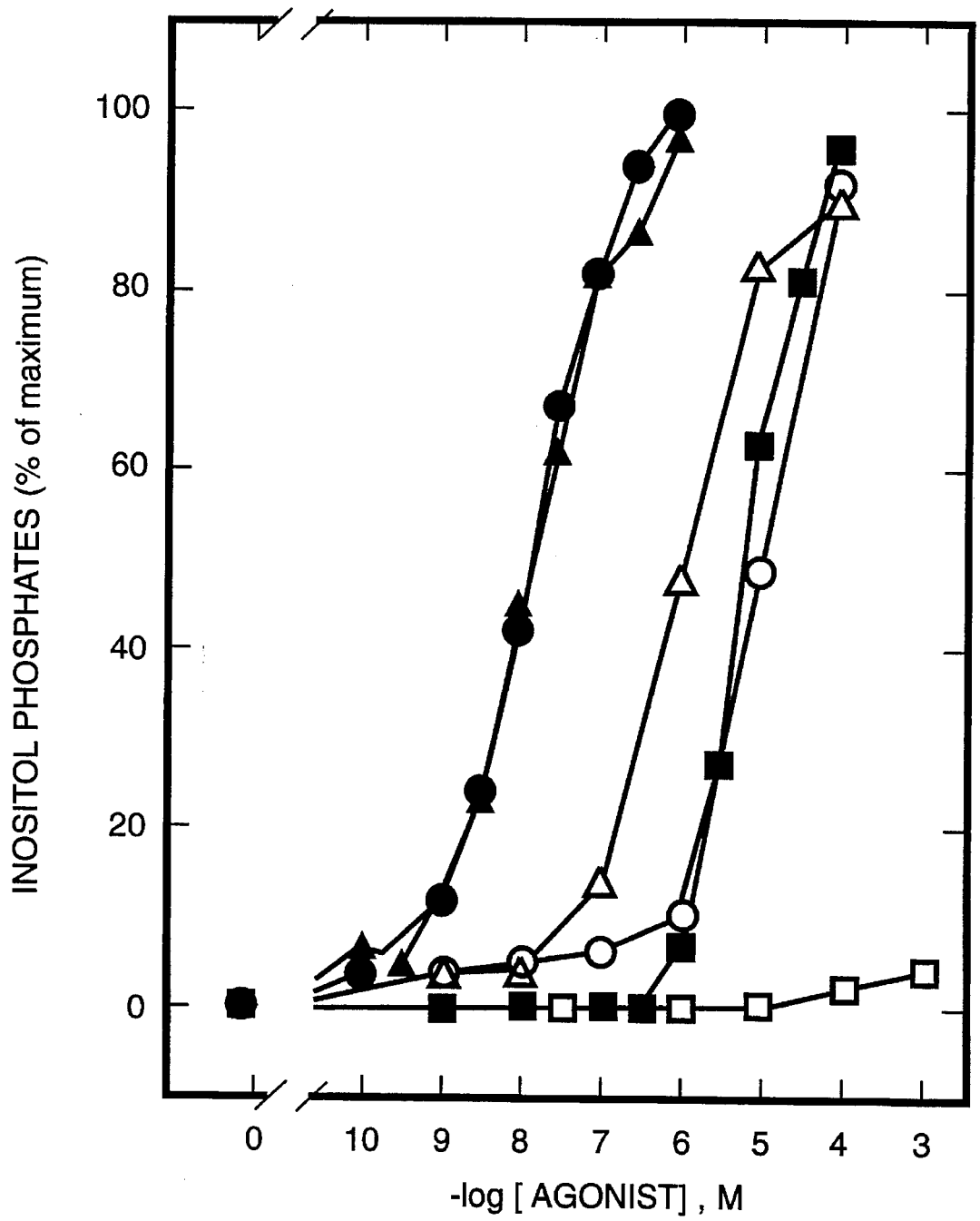
FIG. 5 is a graph that presents data directed at concentration-dependent stimulation of phospholipase C activity by 2-thioether analogs of AMP and ATP, wherein the abscissa is labeled "-log [Agonist], M" and the ordinate is labeled "Inositol Phosphates (% of Maximum)".

Accordingly, although somewhat less potent, it is clear from the data presented in FIG. 5 that the monophosphate 2-thioether analogs of ATP can behave as full-fledged agonists of the $P_{2Y}$ receptor.

EXAMPLE 7

This example illustrates the phospholipase C activity stimulated by $N_6$-and 2-thioether-analogs of ATP.

Phospholipase C activity was assessed using the method recited in Example 3. The results of this set of assays are presented in FIG. 6, with reference to the following compounds: ATP (○); $N^6$-methyl-ATP (●); 2-hexenylthio-ATP (Δ); $N^6$-methyl-2-hexenylthio-ATP (▲); and $N^6$-methyl -2 -hexenylthio-AMP (□). [$^3$H]-inositol phosphate accumulation in the presence of 1 μM GTPγS was 250 cpm (0%). Maximal levels (100%) of [$^3$H]-inositol phosphate accumulation in the presence of GTPγS and a maximal concentration of $N^6$-methyl-2-hexenylthio-ATP was 9150 cpm. Data from different experiments were normalized as percentages of maximal (100%) stimulation levels (y-axis), as a function of the negative log of (putative) agonist concentration (x-axis).

These data show the $N^6$-substitution, either of ATP itself or of a more potent 2-thioether, such as $N_6$-methyl-2-(5-hexenyl) thio-ATP, did not markedly affect the apparent potency at the $P_{2Y}$ receptor. Upon $N^6$-methylation, the potencies of ATP (compare 5'-ATP and $N^6$-methyl-ATP) and 2-hexenylthio-ATP (compare 2-(5-hexenyl)thio-ATP and $N^6$-methyl-2-(5-hexenyl)thio-ATP) were diminished by only 7-fold and 2.6-fold, respectively.

EXAMPLE 8

This example illustrates the concentration-response relationships for ATP and its analogs by means of the assessment of the relaxation of the carbachol-contracted guinea pig taenia coli.

Figure 7:
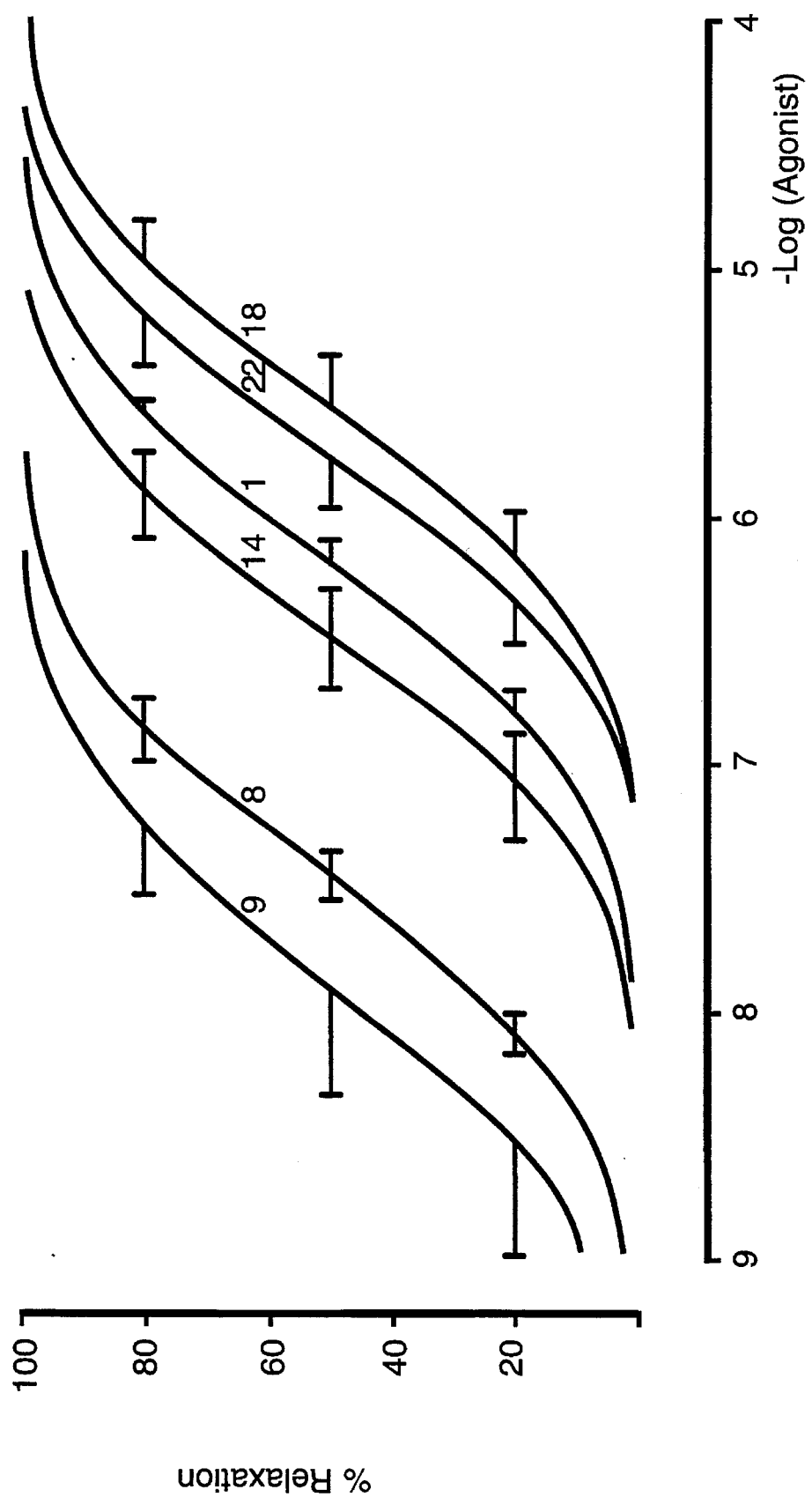
FIG. 7 is a graph that presents data directed at concentration-dependent relaxation of the carbachol-contracted guinea pig taenia coli of ATP, wherein the abscissa is labeled "-log (Agonist)" and the ordinate is labeled "% Relaxation."

Muscular relaxation assays were performed as recited in Example 3. The results are displayed graphically in FIG. 7, wherein the order of the curves are data predicated on the stimulation of 2-(5-hexenyl)thio-ATP, 2-hexylthio-ATP, 2-(2–4-nitrophenylethyl)thio-AMP, 5'-ATP, $N^6$-methyl-ATP, and 2-(6-cyanohexyl)thio-ATP, as one views the curves from left to right. All curves are the mean of two determinations except for 5'-ATP (n=38), 2-hexylthio-ATP (n=4), 2-(5-hexenyl)thio-ATP (n=3), and 2-(2–4-nitrophenylethyl)thio-AMP (n=5). The ordinate axis shows the percentage relaxation of the carbachol-induced contraction; the abscissa axis shows the negative log of the putative agonist concentration. The $pD_2$ value for 2-methylthio-ATP is 8.0±0.15, as reported by Hoyle et al., in *Receptor Data for Biological Experiments*, (H. N. Doods and J. C. A. Van Meel, eds., 1992b) at pp. 54–61.

These data relate to comparisons of the potency of various ATP derivatives to stimulate a differently located $P_{2Y}$ receptor, namely in the taenia coli as compared to the stimulation of the $P_{2Y}$ receptors of erythrocyte membranes, the studies of which were disclosed in Examples 3–7. The same results are obtained: long-chain alkyl thio-substituted ATP, such as 2-(5-hexenyl)thio-ATP and 2-hexylthio-ATP are significantly more potent than ATP itself, at least by one order of magnitude. The one monophosphate derivative was slightly less potent than ATP, but was certainly sufficiently potent to be considered an agonist.

The conclusion of these data is that the results using the phospholipase C assay are consistent, and therefore confirmed.

EXAMPLE 9

This example illustrates the positive correlation of results obtained using the phospholipase C and muscular relaxation assays.

Figure 8:
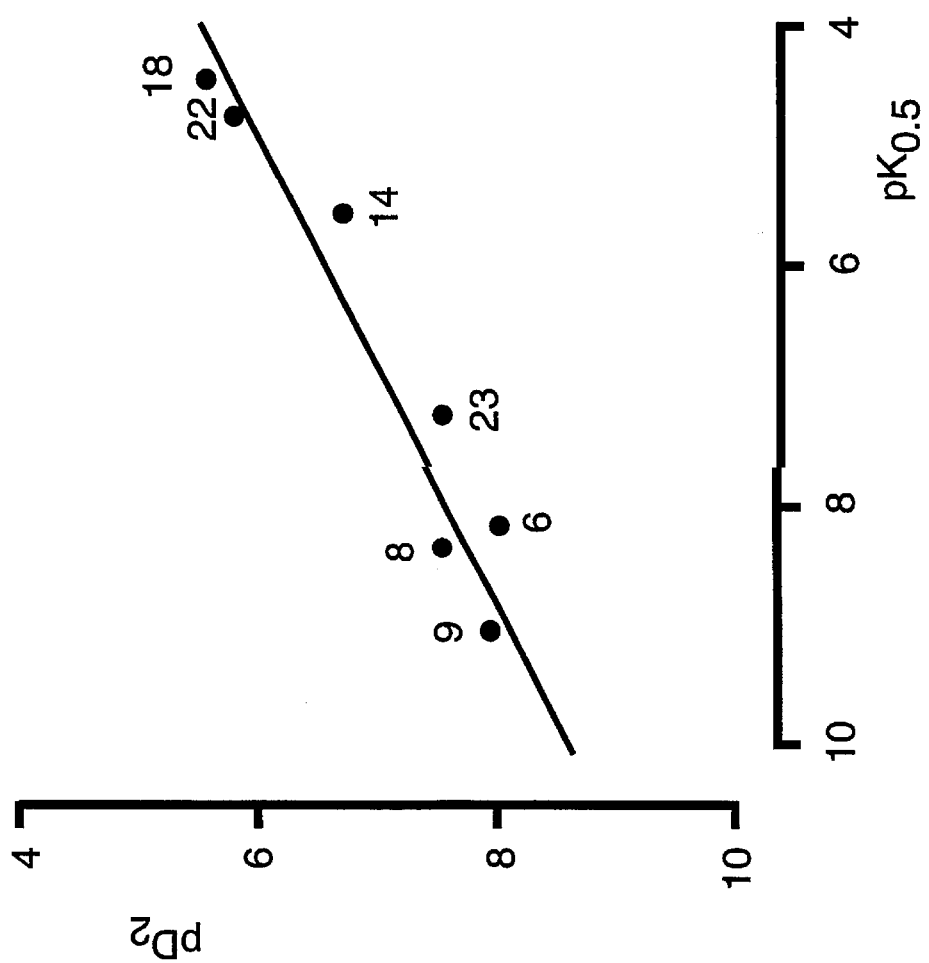
FIG. 8 is a graph of a linear regression curve that correlates data directed at erythrocyte $P_{2Y}$ receptor agonism with taenia coli $P_{2Y}$ receptor agonism, wherein the abscissa is labeled "$pK_{0.5}$" and the ordinate is labeled "$pD_2$".

A linear regression plot of the $pD_2$ values derived from the muscular relaxation assay and the $pK_{0.5}$ values derived from the phospholipase C assay is presented in FIG. 8; both assays were performed as recited in Example 3, using the same putative agonists. As can be readily discerned in FIG. 8, a straight line is obtained, which demonstrates the positive correspondence. The result is particularly significant in view of the wide range of putative agonist structures used, as follows: 2-methylthio-ATP, 2-hexylthio-ATP, 2-(5-hexenyl)thio-ATP, 2-(2–4-nitrophenylethyl)thio-AMP, 2-(6-cyanohexyl)thio-AMP, $N^6$-Me-ATP, and $N^6$-Me-2-(5-hexenyl)thio-ATP.

EXAMPLE 10

This example illustrates that certain ATP analogs are specific for $P_{2Y}$ receptors and not specific for $P_{2X}$ receptors.

Certain ATP analogs known to bind to $P_{2Y}$ receptors, as disclosed in Examples 4–9, were tested on membrane preparations of urinary bladder, which is known to include $P_{2X}$ receptors (See, e.g., Lukacsko et al., *Eur. J. Pharmacol.*, 80, 401–406 (1982)). The assay used is predicated on the specific displacement of a putative ligand by a [$^3$H] compound known to bind at the $P_{2X}$ receptor, namely α,β-methylene-ATP.

For this assay, male Wistar rats (200–250 g) were killed by asphyxiation with $CO_2$. Urinary bladders were removed immediately and placed in modified Krebs solution (adjusted to pH 7.4) of the following composition: 133 mM NaCl, 4.7mM KCl, 2.5 mM $CaCl_2$, 0.6 mM $MgSO_4$, 16.3 mM $NaHCO_2$, 1.4 mM $NaH_2PO_4$, 7.7 mM glucose. They were trimmed free from surrounding adipose and connective tissues, minced and homogenized in 10 volume of ice-cold 50 mM Tris/HCl buffer containing 1 mM EGTA, 1 mM benzamidine hydrochloride, 0.1 mM phenylmethylsulfonyl fluoride (PMSF), 0.01% (w/v) bacitracin, and 0.002% (w/v) soybean trypsin inhibitors, pH 7.4 (buffer A), with a Polystron PT-3000 (Kinematica, Switzerland) twice in 15 s bursts at 30.000 rpm. The homogenate was centrifuged at 170 xg for 5 min at 4° C. The supernatant was passed through double layers of nylon mesh and centrifuged at 105,000 xg for 50 min at 4° C. The pellets were washed and suspended in buffer A and the protein content was determined using the method of Peterson (Anal. Biochem., 83, 346–356 (1977)).

Displacement experiments were carried out by incubating the membrane preparations with about 10 nM [$^3$H]-α,β-MeATP and various concentrations of an unlabeled ligand in buffer A at 4° C. for 120 min (final volume 0.5 ml). At the end of the incubation, the assay tubes were put on ice and the reaction mixture was rapidly filtered through a Whatman GF/B filter (presoaked in 20 mM disodium pyrophosphate solution)under vacuum. The filters were washed with 2 aliquots of 5 ml ice-cold 5 mM Tris/HCl buffer, pH 7.4, dried under an infrared lamp, and then the radioactivity trapped in the filters was measured in a Beckman $SC_{6100}I$ scintillation counter with an efficiency of about 56 to 61%. Non-specific binding was determined by including 100 μM β,γ-methylene-ATP in the incubation mixture.

Figure 9:
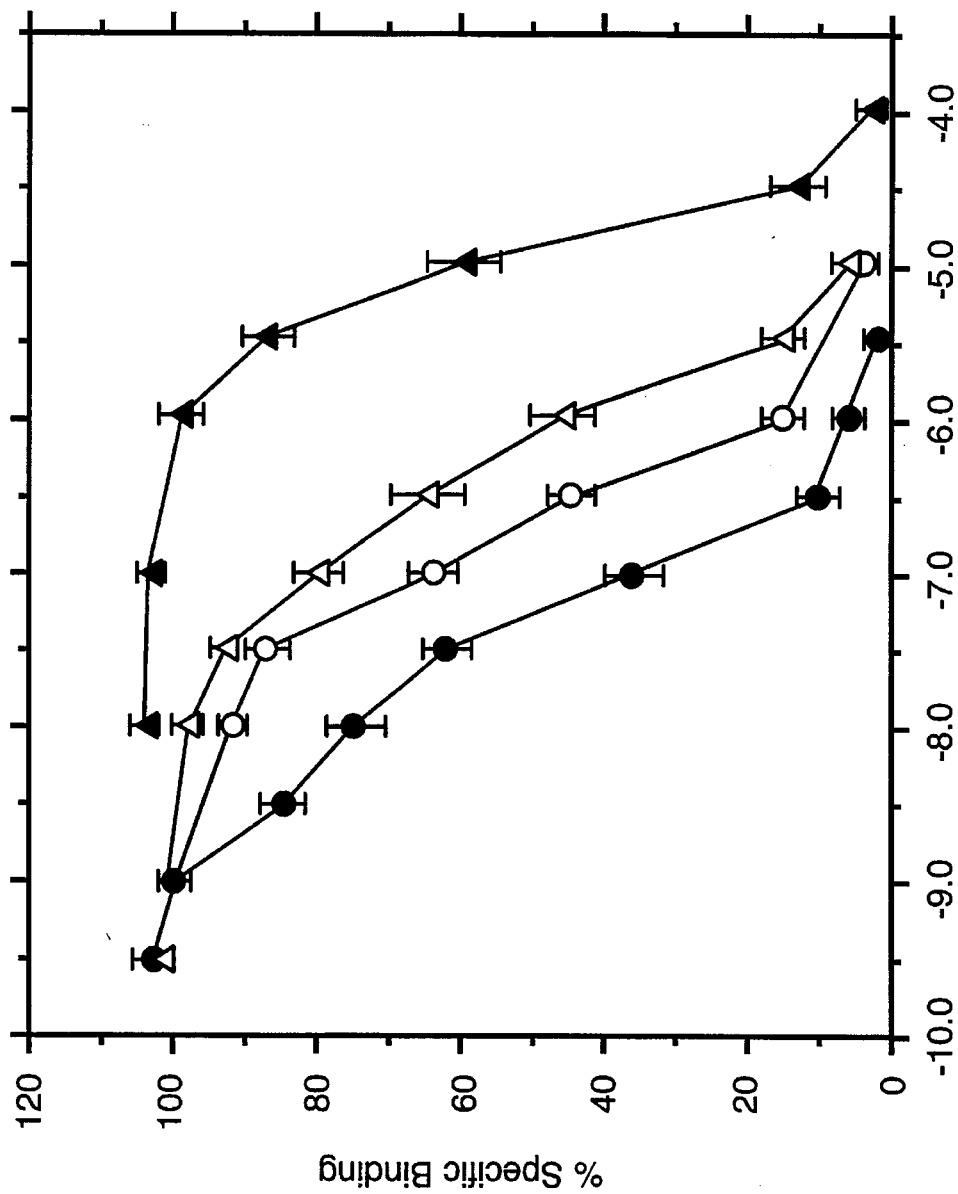
FIG. 9 is a graph that presents data directed at the displacement of certain alkylthio- and $N^6$-alkyl-substituted ATP analogs from rat urinary bladder membranes by [$^3$H]-α,β-methylene ATP analogs, wherein the abscissa is labeled "Log [Ligand][M]" and the ordinate is labeled "% Specific Binding".

FIG. 9 displays the results of the aforementioned $P_{2X}$ ligand competition assay, for the following compounds: 2-methylthio-ATP (○); 2-cyanohexylthio-ATP (●); $N^6$-methyl-2-hexenylthio-ATP (Δ); and 1,$N^6$-etheno-ATP (▲). The data is plotted % specific binding (y-axis) versus log of the molar concentration of the ligand (x-axis). There is little or no effect of the alkyl chain at the C2 position on the ability of the ligand to bind tightly to the $P_{2X}$ receptor. However, substitution at the $N^6$ position does lessen the ability of the ATP derivative to bind tightly.

Figure 6:
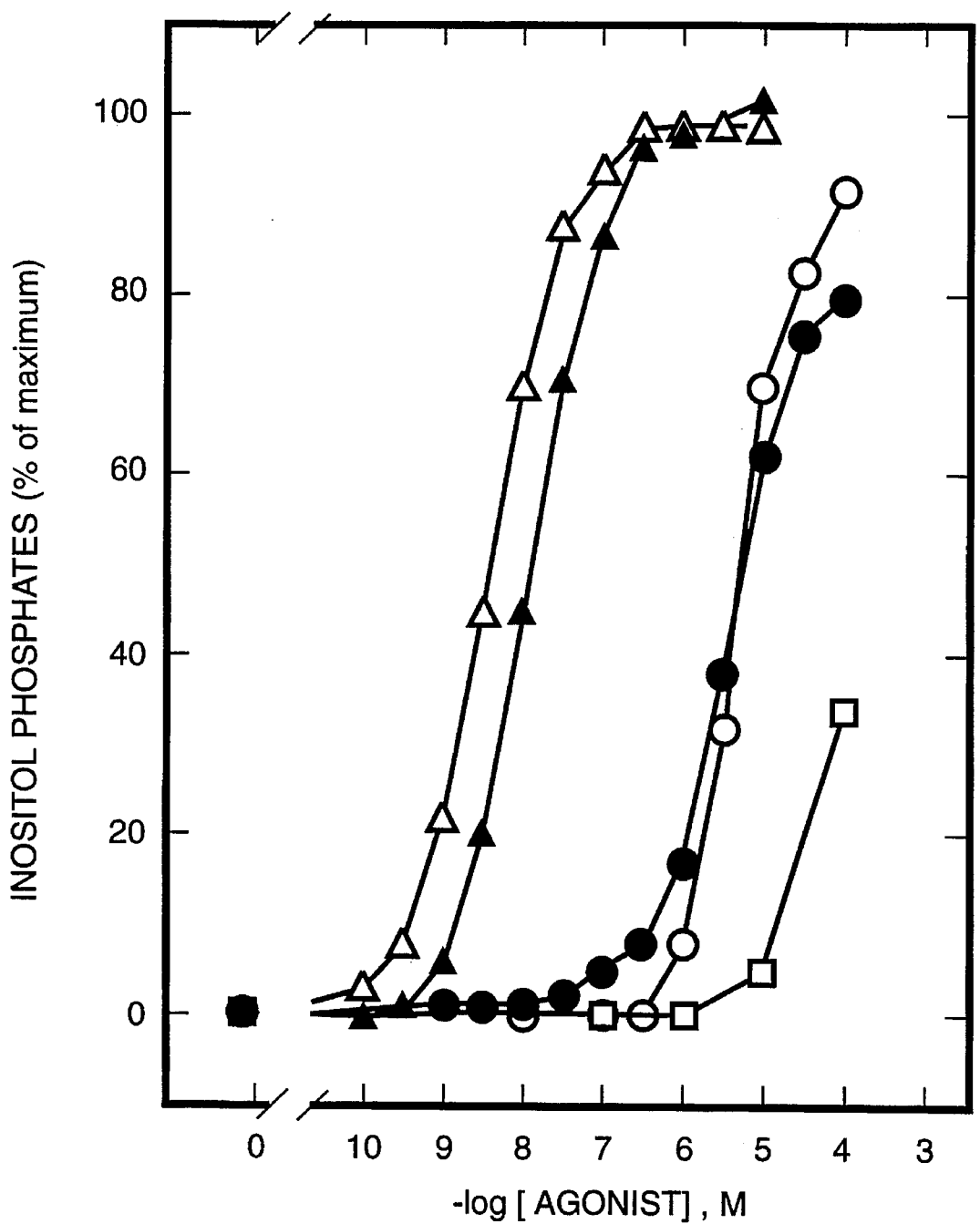
FIG. 6 is a graph that presents data directed at concentration-dependent stimulation of phospholipase C activity by $N^6$- and 2-thioether analogs of ATP, wherein the abscissa labeled "-log [Agonist], M" and the ordinate is labeled "Inositol Phosphates (% of Maximum)".

By comparison with the results disclosed in FIG. 6 and discussed in Example 7, $N^6$-Me-2-hexenylthio-ATP is 50% effective at $10^{-8}$M ($K_{0.5}$) with reference to the $P_{2Y}$ receptor; the same relative activity level of the same compound at the $P_{2X}$ receptor requires two orders of magnitude greater concentration. Accordingly, $N^6$-and C2-substituted ATP analogs provide compounds that are able to stimulate the $P_{2Y}$ but not, or to a far lesser extent, the $P_{2X}$ receptor.

EXAMPLE 11

This example illustrates the phospholipase C activity and the muscle relaxation/contraction effect stimulated by ATP analogs that are substituted at the phosphate chain, the purine base, and/or the ribose moiety, and provide a compilation of data derived from the biochemical and biological characterization of the various compounds disclosed herein.

Figure 10:
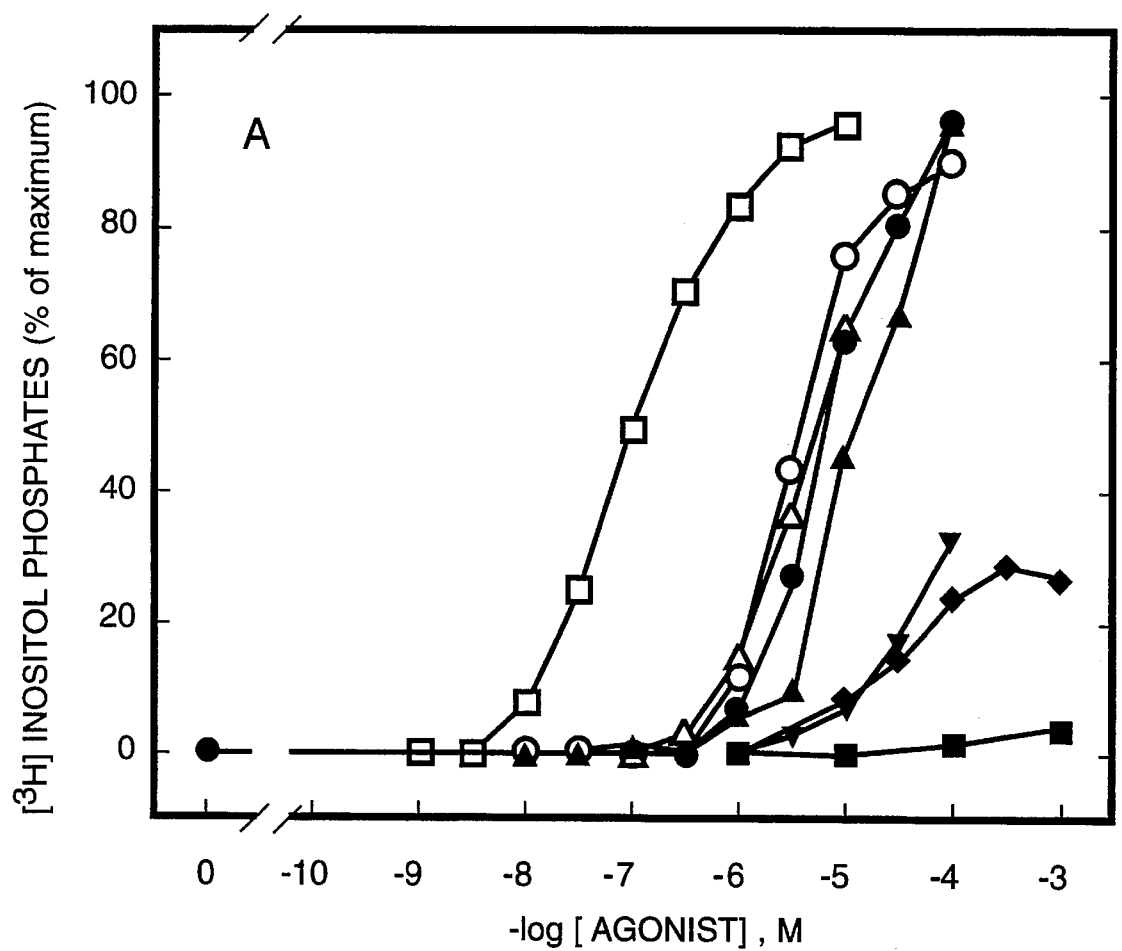
FIG. 10 is a graph that presents data directed to guanine nucleotide-dependent stimulation of turkey erythrocyte phospholipase C activity by ATP analogs substituted on the phosphate chain, wherein the abscissa is labeled "Log [Agonist], M" and the ordinate is labeled "[$^3$H] Inositol Phosphates (% of Max.)".
Figure 11:
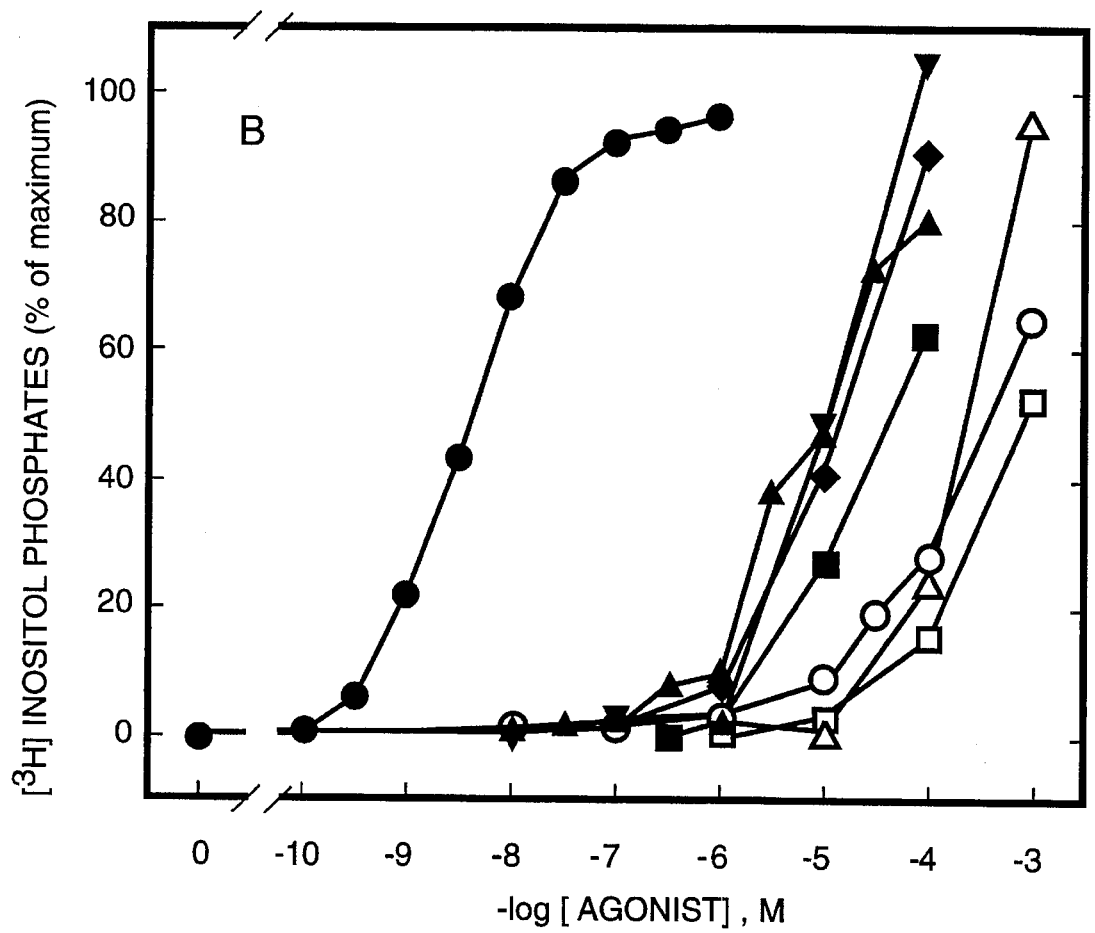
FIG. 11 is a graph that presents data directed to guanine nucleotide-dependent stimulation of turkey erythrocyte phospholipase C activity by ATP analogs substituted on the purine base, wherein the abscissa is labeled "Log [Agonist], M" and the ordinate is labeled "[$^3$H] Inositol Phosphates (% of Max.)".
Figure 12:
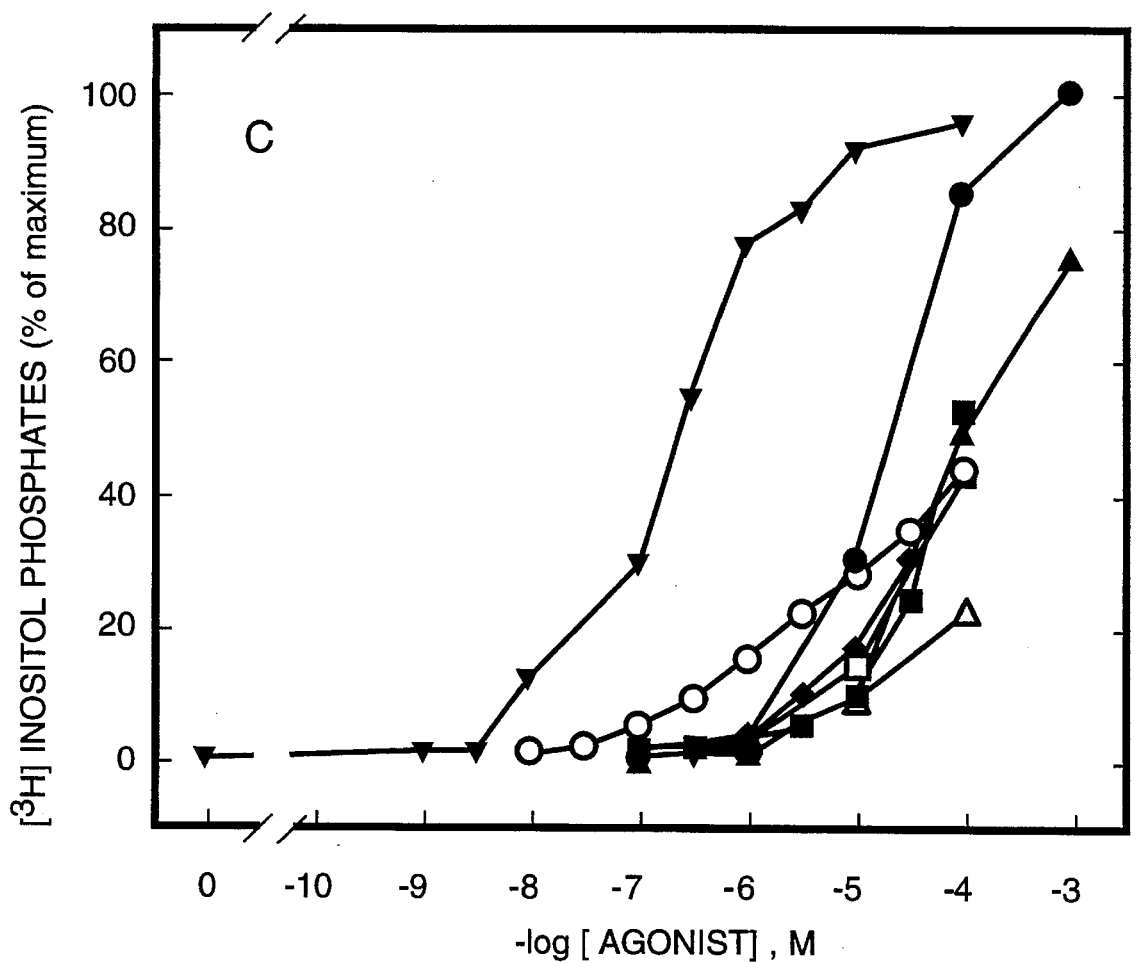
FIG. 12 is a graph that presents data directed to guanine nucleotide-dependent stimulation of turkey erythrocyte phospholipase C activity by ATP analogs substituted on the ribose moiety, wherein the abscissa is labeled "Log [Agonist], M" and the ordinate is labeled "[$^3$H] Inositol Phosphates (% of Max.)".
Figure 13:
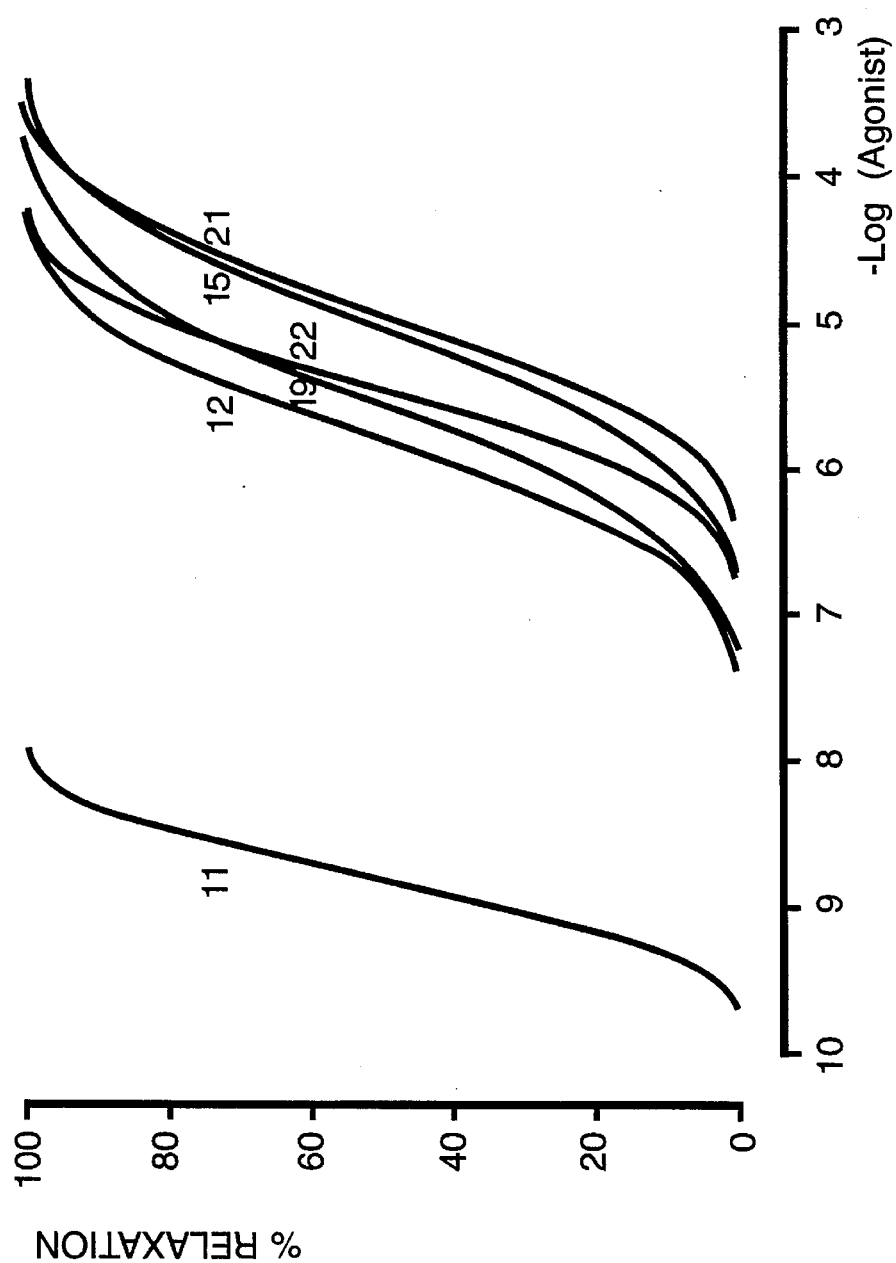
FIG. 13 is a graph that presents data directed to concentration-response relationships for ATP analogs (putative $P_{2Y}$ receptor agonists) causing relaxation of the carbachol-contracted guinea pig taenia coli, wherein the abscissa is labeled "Log [Agonist], M" and the ordinate is labeled "[$^3$H] Inositol Phosphates (% of Max.)".
Figure 14:
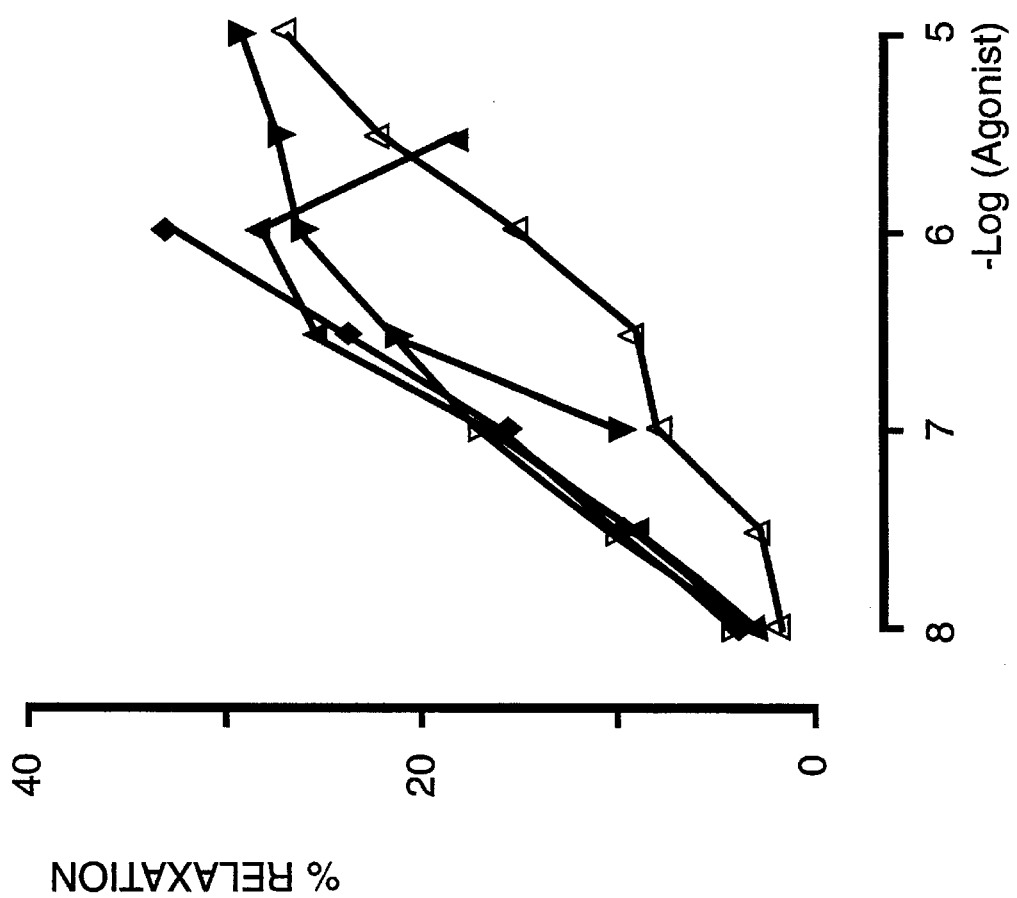
FIG. 14 is a graph that presents data directed to concentration-response relationships for ATP analogs (putative endothelial $P_{2Y}$ receptor agonists) causing relaxation of the noradrenalin-contracted rabbit aorta, wherein the abscissa is labeled "Log [Agonist], M" and the ordinate is labeled "[$^3$H] Inositol Phosphates (% of Max.)".
Figure 16:
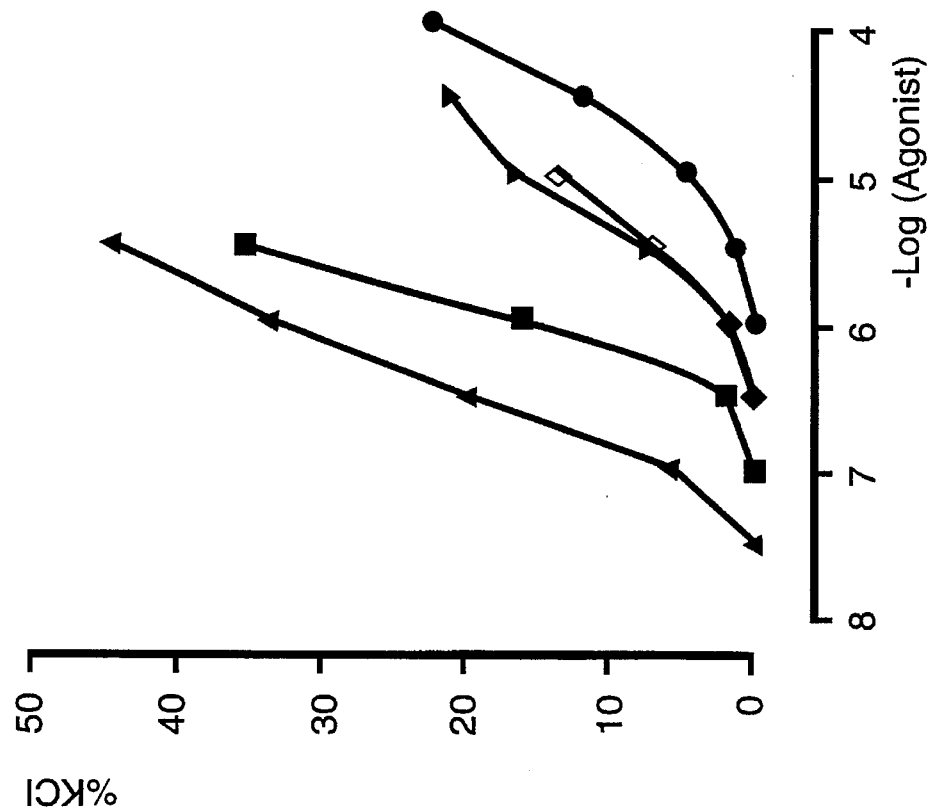
FIG. 16 is a graph that presents data directed to concentration-response relationships for ATP analogs (putative $P_{2X}$ receptor agonists) causing contraction of the guinea pig isolated vas deferens, wherein the abscissa is labeled "Log [Agonist], M" and the ordinate is labeled "[$^3$H] Inositol Phosphates (% of Max.)".
Figure 15:
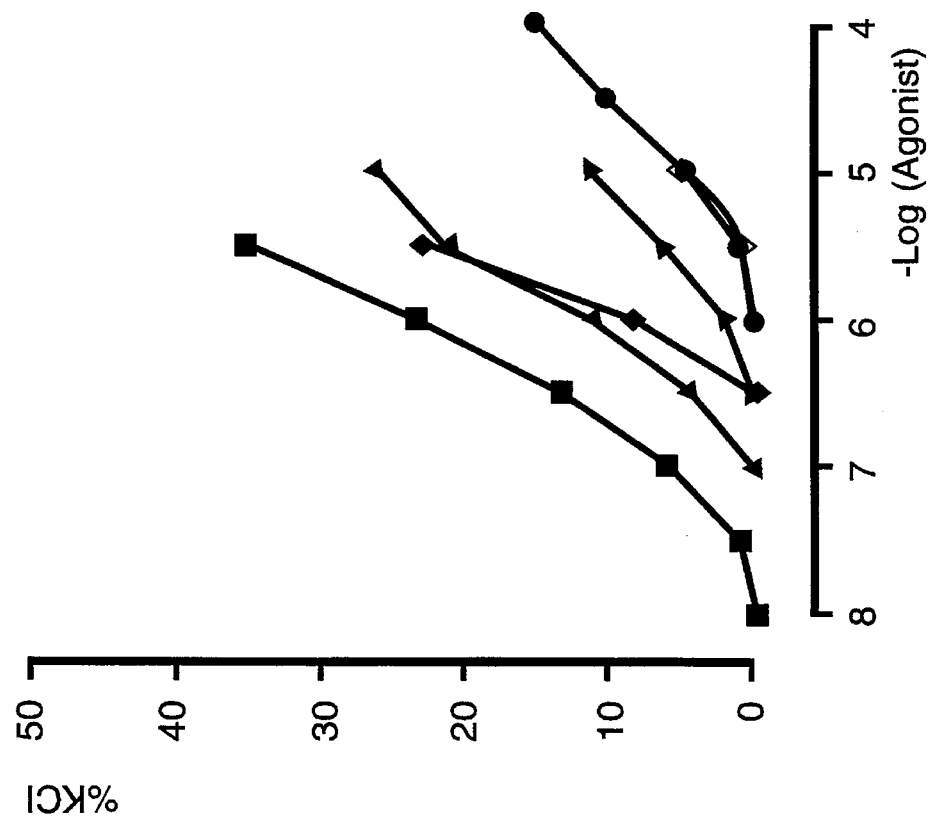
FIG. 15 is a graph that presents data directed to concentration-response relationships for ATP analogs (putative $P_{2X}$ receptor agonists) causing contraction of the guinea pig isolated urinary bladder detrussor muscle, wherein the abscissa is labeled "Log [Agonist], M" and the ordinate is labeled "[$^3$H] Inositol Phosphates (% of Max.)".

Phospholipase C activity and muscle relaxation/contraction effects were assessed using the methods recited in Example 3. The results of this set of assays are presented in FIGS. 10–16. In FIGS. 10–12, which present the result of assays of phospholipase C activity in turkey erythrocyte membranes, the x-axis is marked in units of the log of the molar concentration of the putative $P_{2Y}$ receptor agonist tested and the y-axis is marked in units of the percentage of maximum production of [$^3$H]-inositol phosphate generated. In FIG. 13, the x-axis is marked in units of the negative log of the molar concentration of applied putative $P_{2Y}$ receptor agonists and the y-axis is marked in units of the percentage relaxation of the 50 nM carbachol-induced contraction of guinea pig taenia coli. In FIG. 14, the x-axis is also marked in units of the negative log of the molar concentration of applied putative $P_{2Y}$ receptor agonists and the y-axis is marked in units of the percentage relaxation of the 1 µM noradrenalin-induced contraction of rabbit aorta endothelium. In FIGS. 15–16, the x-axis is marked in units of the negative log of the molar concentration of applied putative $P^{2X}$ receptor agonists and the y-axis is marked in units of the percentage contraction relative to a standard dose of KCl (i.e., 60 mM), as assessed in guinea pig isolated urinary bladder detrussor muscle (FIG. 15) and guinea pig isolated vas deferens (FIG. 16).

The assays were performed using the following compounds:

FIG. 10 (directed to ATP analogs substituted on the phosphate chain): ATP (●); ADP (△); AMP (■; α,β-methyl-ATP (▼); β,γ-methyl-ATP (♦); AppNHp (○); ATP-α-S (S-isomer; △); and ADP-β-S (□).

FIG. 11 (directed to ATP analogs substituted on the purine base): $N^6$-methyl-ATP (△); 8-Br-ATP (■); 8-(6-aminohexylamino)-ATP (▼); 2-(6-cyanohexylthio)-ATP (●); adenosine-N1-oxide-5'-triphosphate (◊); N1,$N^6$-etheno-ATP (o); UTP (△); and 5-F-UTP (□).

FIG. 12 (directed to ATP analogs substituted on the ribose moiety): 2'-deoxy-ATP (●); 3'-deoxy-ATP (▲); 2',3'-dideoxy-ATP (■); 3'-amino-3'-deoxy-ATP (▼); 3'-acetylamino-3'-deoxy-ATP (♦); 3'-[3-(4-hydroxyphenyl)-propionylamino]-3'-deoxy-ATP (○); 3'-benzylamino-3'-deoxy-ATP (△); and 2',3'-isopropylidene-AMP (□).

FIG. 13 (from left to right at the 50% level): 2-(6-cyanohexyl)thio-ATP (11); $N^6$-methyl-ATP (12); 2'-deoxy-ATP (19); 3'-amino-3'-deoxy-ATP (22); adenosine-N-oxide-5'-triphosphate (15); 2',3'-dideoxy-ATP (21).

FIG. 14: 2-(6-cyanohexyl)thio-ATP (▲); adenosine-N1-oxide-5'-triphosphate (△); 8-(6-aminohexylamino)-ATP (∇); 5-fluoro-UTP (♦); 3'-deoxy-amino-ATP (▼).

FIGS. 15 and 16: 3'-benzylamino-3-deoxy-ATP (■); 2-(6-cyanohexyl)thio-ATP (▲); 5-fluoro-UTP (♦); 3'-deoxy-3'-amino-ATP (▼); ATP (●).

Reduction in the number of phosphates in the ATP molecule caused a marked reduction in activity at $P_{2X}$ receptors in the vas deferens. For example, adenosine 5'-diphosphate was less potent than ATP, and adenosine 5'-monophosphate was without effect. At urinary bladder $P_{2X}$ receptors, ADP was equipotent with ATP, and AMP was inactive. At $P_{2Y}$ receptors in the turkey erythrocyte, ADP was 3-fold less potent than ATP, and AMP was inactive (see FIG. 10). In the taenia coli, ADP was equipotent to ATP, and AMP was much less potent. Thus, neither the $P_{2Y}$ nor $P_{2X}$ receptors tested in these preparations exhibited much selectivity for ATP versus ADP.

Replacement of a bridging oxygen with a methylene group, to form α,β-methylene ATP or β,γ-methylene ATP resulted in a reduced activity in the taenia coli, but markedly enhanced activity in the urinary bladder and vas deferens. In the erythrocyte preparation, α,β-methylene ATP was a very weak, yet full agonist, and β,γ-methylene ATP was nearly inactive at ≧100 µM (FIG. 10). Replacement of a bridging oxygen with an imido group to form β,γ-imido ATP had an effect similar to methylene replacement in the taenia and vas deferens, but it was equipotent with ATP in the erythrocytes.

Thiophosphate modifications also affected activity. The S-isomer of ATP-α-S was approximately 10-fold more potent than ATP in the taenia coli (see Burnstock et al., *Br. J. Pharmacol.*, 82, 369–374 (1984)), but it was 2-fold less potent than ATP at the turkey erythrocyte $P_{2Y}$ receptor. Phosphorothioate substitution on the terminal phosphates of ATP or ADP, i.e., ATP-γ-S and ADP-β-S, respectively, enhanced potency relative to the parent compound at $P_{2Y}$-receptors on turkey erythrocyte but not in the taenia coli. ADP-β-S was approximately 140 times more potent than ATP, and 400 times more potent than ADP in the turkey erythrocyte model (FIG. 10).

The phosphorothioate compounds did not have significantly greater potency than ATP at the $P_{2X}$ receptor in either the urinary bladder or vas deferens (see Burnstock et al., supra (1984); Burnstock et al., *Br. J. Pharmacol.*, 84, 431–434 (1985)).

Cyclized β,γ-methylene ATP was without effect in all seven types of preparation tested for biological activity, as presented in Example 3.

In general, modifications of the purine nucleus in ATP at the C8 or $N^6$ position were not well tolerated by $P_{2X}$ receptors, where compounds so modified were without effect at the highest concentrations tested (usually 30 µM). At the $P_{2Y}$ receptors in the mesenteric artery, taenia coli and erythrocyte preparations, most compounds formed by C8 or $N^6$ substitutions were either inactive or of much lower potency than ATP. However, $N^6$-methyl ATP, although inactive in vascular smooth muscle, was equipotent with ATP in the taenia coli and inactive in $P_{2X}$ preparations. This compound was also only slightly less potent (7-fold) than ATP for stimulation of inositol phosphate formation in erythrocyte membranes (FIG. 11). In addition, both 8-(6-aminohexylamino)ATP and adenosine-N1-oxide triphosphate were much more potent than ATP as agonists at the endothelial receptor in the aorta. However, they had no activity at the mesenteric artery $P_{2Y}$ receptor and were less potent than ATP at the turkey erythrocyte $P_{2Y}$ receptor (FIG. 11).

Substitution at C-2, as in 2-(6-cyanohexyl)thio ATP, as discussed above in Examples 6 and 8, produced an agonist more potent than ATP in all systems except the $P_{2X}$ system of the saphenous artery, and it was by far the most potent agonist in several $P_{2Y}$ receptor preparations (FIGS. 11 and 13). Although it was approximately 100 times more potent than ATP at urinary bladder $P_{2X}$ receptors (FIG. 15), it produced tonic contractions rather than the typical phasic contractions of ATP. In the presence of indomethacin (which inhibits prostaglandin synthesis), 2-(6-cyanohexyl)thio-ATP produced contractions that were less tonic, and with a lower potency than ATP under the same conditions.

5-Fluoro-UTP, was only a weak agonist in the $P_{2Y}$ systems of turkey erythrocytes (FIG. 11) and guinea-pig taenia coli and was inactive at $P_{2Y}$ receptors in the rabbit mesenteric artery. However, in the rabbit aorta $P_{2Y}$ receptors, it was more potent than ATP. In the $P_{2X}$ systems of the rabbit saphenous artery and the guinea-pig vas deferens, 5-F-UTP was inactive. At guinea-pig bladder $P_{2X}$ receptors it was more potent than ATP (FIG. 15).

Ribose modifications revealed that removal of either free hydroxyl group (at 2'-or 3'-positions) resulted in the loss of activity in most but not all of the smooth muscle assays. 2'-Deoxy-ATP, for example, was roughly equipotent with ATP in the taenia coli (FIG. 13), and was 7-fold less potent than ATP in the turkey erythrocyte (FIG. 12). The related isomer 3'-deoxy-ATP (also known as cordycepin 5'-triphosphate) was less potent than 2'-deoxy-ATP at $P_{2Y}$ receptors (FIG. 12), but was as active as ATP, or nearly so, in the vas deferens and urinary bladder $P_{2X}$ receptor systems. Curiously, 2',3'-dideoxy-ATP was as potent as ATP at taenia coli $P_{2Y}$ receptors (FIG. 13) and weakly active at turkey erythrocyte $P_{2Y}$ receptors (FIG. 12). 2',3'-Dideoxy-ATP was also active at vas deferens $P_{2X}$ receptors (≈ATP) and at urinary bladder $P_{2X}$ receptors (>ATP).

Substitutions at the 3'-position produced various results. 3'-Acetylamino-3'-deoxy-ATP was more potent than ATP at rabbit mesenteric artery $P_{2Y}$ receptors but was inactive at 10 µM at rabbit aorta $P_{2Y}$ receptors. In contrast, a related compound, 3'-[3-(4-hydroxyphenyl)-propionylamino]-3'-deoxy-ATP, was considerably more potent than ATP in the aorta, but inactive in the mesenteric artery. Both these compounds were nearly inactive at $P_{2Y}$ receptors in the taenia coli and in turkey erythrocyte membranes. The simpler derivative, 3'-amino-ATP, also provided a contrast, being approximately 15 times more potent than ATP in the erythrocyte (FIG. 12), and almost as potent as ATP in the taenia coli (FIG. 13). At $P_{2X}$ receptors 3'-amino-3'-deoxy-ATP, 3'-acetylamino-3'-deoxy-ATP, and 3'-(p-hydroxyphenylpropionylamino)-3'-deoxy-ATP were more or less as potent as ATP in the guinea-pig bladder (FIG. 15) and vas deferens (FIG. 16), but inactive in the saphenous artery.

3'-Benzylamino-3'-deoxyATP was the most potent agonist at vas deferens $P_{2X}$ receptors (FIG. 15) and also highly potent at urinary bladder $P_{2X}$ receptors (FIG. 16). This compound was inactive in another $P_{2X}$-system (saphenous artery) and either inactive or only a weak agonist in $P_{2Y}$-systems (e.g. turkey erythrocytes, FIG. 12).

The homologous compounds 2',3'-isopropylidene-ATP and 2',3'-isopropylidene-AMP had unexpectedly different profiles of activity. Neither was particularly active at either $P_{2X}$ or $P_{2Y}$ receptors, but the AMP derivative was a potent agonist at the rabbit endothelial $P_{2Y}$ receptor.

The data reported herein reveals identified ATP derivatives of high potency and in some cases selectivity as $P_{2X}$ and $P_{2Y}$ receptor agonists. Several compounds were inactive in the $P_{2X}$ receptor systems (e.g. $N^6$-methyl-ATP, 8-(6-aminohexylamino)-ATP, adenosine N1-oxide 5'-triphosphate, 2'-deoxy-ATP, and isopropylidene-AMP), and one (3'-benzylamino-3'deoxyATP) was inactive in the $P_{2Y}$ receptor systems. Further analyses of the relative affinities of these agonists in different tissue preparations provides evidence for heterogeneity within the $P_{2X}$ and $P_{2Y}$ receptor sub-classes.

Modifications of ATP that greatly reduce or abolish activity within most $P_{2X}$ and $P_{2Y}$ preparations are: N1,$N^6$-etheno modification (e.g., N1,$N^6$-etheno-ATP), removal of 3'-hydroxyl (e.g., 3'-deoxy-ATP), and cyclizing the phosphate to the 3'-position (e.g., β,γ-methylene-adenosine-3',5'-cyclic triphosphate, which also contained a β,γ-methylene modification). Substitution at the purine $N^6$ or 1-position is tolerated at $P_{2Y}$, but not $P_{2X}$ receptors. 8-Bromo-ATP, although reported previously to be somewhat active at $P_2$ receptors (Satchell and Maguire, *J. Pharmacol. Exp. Therap.*, 195, 540–548 (1982)), was relatively ineffective at the receptors tested in this study.

The results of the various pharmacological and biochemical studies of the agonists disclosed herein are tabulated, as follows:

| | Activity of compounds disclosed herein in various biochemical and pharmacological models, described at Example 3. | | | | | | |
|---|---|---|---|---|---|---|---|
| | phosphatidyl inositol metabolism $(K_{0.5}, nM)^a$ | $P_{2Y}$ Receptors relaxation, potency relative to ATP$^b$ (pD$_2$) | | | $P_{2X}$ Receptors contraction, potency relative to ATP$^b$ (pD$_2$) | | |
| Compound | erythrocyte | *taenia coli* | aorta | mes. artery | saph. artery$^c$ | vas def. | bladder |
| ATP and triphosphate modifications | | | | | | | |
| ATP | 2800 ± 700 | =(6.2)$^d$ | =(4.5) | =(6.0) | =[5%] | =(3.5)$^e$ | =$^e$ |
| ADP | 8000 ± 2000 | =$^h$ | =(5.2) | =(5.2) | na | –$^e$ | =$^e$ |
| AMP | 4 ± 2% at 10$^{-4}$M | –$^h$ | =(4.8) | =(5.0) | na | — | na$^e$ |
| Adenosine | na | –(3.9)$^l$ | +(5.7) | =(6.0) | na | na | na |
| α,β-Me-ATP | >100,000 | =(5.6)$^e$ | f | f | =[5.9%] | +(5.3)$^e$ | ++(5.7)$^e$ |
| β,γ-Me-ATP | >100,000 | –$^e$ | f | g | ++[89%] | +$^e$ | ++$^e$ |
| β,γ-Me-Adenosine-3',5'-cyclic triphosphate | na | — | na | na | na | na | na |
| AppNHp | 4450 ± 1150 | –$^e$ | +(5.5) | +(6.6) | na | +$^b$ | +$^b$ |
| ATP-α-S (S-isomer) | 8930 ± 4440 | +$^e$ | f | +(6.6) | na | =$^j$ | =$^j$ |
| ATP-γ-S | 1260 ± 380 | =$^e$ | +(5.7) | +(5.8) | na | ++$^i$ | + |
| ADP-β-S | 96 ± 27 | = | +(5.8) | +(5.8) | na· | =$^j$ | =$^j$ |
| base modifications | | | | | | | |
| 2-MeS-ATP | 8 ± 2 | ++(8.0) | ++$^e$(6.8) | ++(6.5) | na | =$^e$ | =$^e$ |
| 2-Cyclohexylthio-ATP | 24 ± 4 | ++(7.8) | +(6.3, <max) | +(5.9, <max) | na | + | = |
| 2-(6-Cyanohexyl)thio-AMP | 37,000 ± 13,000 | –(4.4) | | +(6.2, <max) | 4.5% | na | na |
| 2-(6-Cyanohexylthio)-ATP$^k$ | 10 ± 5 | ++(8.8) | ++(6.9) | ++(7.0) | =[9.2%] | ++ | h |
| $N^6$-Me-ATP$^i$ | 19,000 ± 6000 | +(5.8) | — | na | na | na | na$^e$ |
| 8-Br-ATP | 47,400 | — | na | na | na | na | — |
| 8-(6-Aminohexyl amino)-ATP | 8200 ± 1200 | — | ++(7.3, sl. <max) | na | na | na | na |

-continued

Activity of compounds disclosed herein in various biochemical and pharmacological models, described at Example 3.

| Compound | phosphatidyl inositol metabolism ($K_{0.5}$, nM)[a] erythrocyte | P_{2Y} Receptors relaxation, potency relative to ATP[b] ($pD_2$) | | | | P_{2X} Receptors contraction, potency relative to ATP[b] ($pD_2$) | | |
|---|---|---|---|---|---|---|---|---|
| | | taenia coli | aorta | mes. artery | saph. artery[c] | vas def. | bladder |
| Adenosine N1-oxide 5'-triphosphate | 16,900 ± 4900 | −(4.9) | ++(6.7, >max) | na | na | na | na | na |
| N1,N6-etheno-ATP | >100,000 | — | na | na | na | na | na | — |
| UTP | 143,000 ± 44,000 | −(3.5) | =(4.8) | +(6.7) | na | na | na | =[e] |
| 5-F-UTP | >100,000 | — | +(6.0, ≈max) | na | na | na | na | ++ |
| 2-Cl-ATP | 72 ± 19 | ++(7.2)[e] | +(5.8) | =(6.2) | na | na | = | = |
| 2-MeS-ADP | 6 ± 3 | | ++[e] | ++ | | | | |
| 2-Hexylthio-ATP | 5 ± 1 | ++(7.5) | ++(6.7, >max) | ++(6.7) | na | na | + | = |
| 2-(S-Hexenyl)thio-ATP[l] | 10 ± 4 | ++(7.9) | ++(≈max) | ++(7.0, ≈max) | na | na | = | + |
| 2-(5-Hexenyl)thio-ADP | 6.8 ± 3.0 | ++(8.44) | | | | | | |
| 2-(5-Hexenyl)thio-AMP | 328 ± 43 | =(6.0) | ++(7.0) | +(6.3) | na | na | na | na |
| 2-Phenylethylthio-ATP[l] | 30 ± 17 | ++(7.1) | ++(6.5, >max) | +(6.2, >max) | na | na | ++ | ++ |
| 2-(2-p-Nitrophenylethyl)-thio-ATP | 12 ± 4 | ++(7.5) | ++(6.2) | ++(7.0) | 2.6% | na | ++ | — |
| 2-(2-p-Nitrophenylethyl)-thio-AMP | 3000 ± 1200 | =(6.5) | +(6.1, <max) | −(5.0) | na | na | — | — |
| 2-(2-p-Aminophenylethyl)-thio-ATP | 1.53 ± 0.21 | | | | | | | |
| 2-(7-Aminoheptyl)thio-ATP | 72.8 ± 46.6 | | | | | | | |
| 2-(7-Thioheptyl)thio-ATP | 773 ± 328 | | | | | | | |
| 2-[(7-Thiocyanatoheptyl)thio]-ATP | 25.9 ± 10.0 | | | | | | | |
| N6-Me-ATP[m] | 19,000 ± 6000 | =(5.8) | — | na | na | na | na | na |
| N6-Me-2-(5-hexenyl)-thio-ATP | 26 ± 7 | +(7.2) | +(5.6) | +(6.0) | 1.5% | na | na | — |
| N6-Me-2-(5-hexenyl)-thio-AMP | >100,000 | — | na | na | 6.7% | na | na | na |
| N6-phenylethyl ATP | 7,000 ± 280 | Not available | | | | | | |
| 2(ethylthioethyl)AMP | 1,000 ± 47 | Not available | | | | | | |
| 2-pentylthio AMP | 10,000 ± 100 | Not available | | | | | | |
| 2-hexylthio AMP | 58 ± 5 | Not available | | | | | | |
| 2-heptylthio AMP | 1,000 ± 80 | Not available | | | | | | |
| 2-octylthio AMP | 295 ± 6 | Not available | | | | | | |
| 2-decylthio AMP | 214 ± 2 | Not available | | | | | | |
| 2-undecylthio AMP | 1,000 ± 20 | Not available | | | | | | |
| 2-(methyl 5-pentenyl)thio AMP | 15%–30% @ 1 mM | Not available | | | | | | |
| ribose modifications | | | | | | | | |
| 2'-Deoxy-ATP | 19,200 ± 6200 | =5.6 | na | na | na | na | na[e] | na |
| 3'-Deoxy-ATP | 75,500 ± 14,800 | — | na | na | na | na | = | — |
| 2',3'-Dideoxy-ATP | 70,800 | =(5.0) | | | | | = | + |
| 3'-Amino-3'deoxy-ATP[j] | 193 | =(5.4) | ++(6.4, ≈max) | na | na | na | + | = |
| 3'-Acetylamino-3'deoxy-ATP[j] | >100,000 | na | na | +(<max) | na | na | = | + |
| 3'-(p-Hydroxyphenylpro-pionylamino)-3'deoxy-ATP[j] | >100,000 | na | ++(<max) | na | na | na | = | + |
| 3'-Benzylamino-3'-deoxyATP | >100,000 | na | na | na | na | na | ++ | ++ |
| 2',3'-Isopropylidene-ATP | 201,000 ± 63,000 | na | na | — | =[7.7%] | na | — | — |
| 2',3'-Isopropylidene-AMP[j] | >100,000 | na | ++(<max) | na | na | na | na | na[f] |

NOTES

[a]$K_{0.5}$ (nM) for stimulation of production of inositol phosphates in turkey erythrocyte membranes, expressed as the mean ± S.E.M. for at least 2 determinations, or % stimulation at concentration indicated. na = not active at $10^{-5}$M.

[b]++ significantly more potent than ATP; + more potent than or equal to ATP; = equal to ATP; − less potent than or equal to ATP; — significantly less potent than ATP; na not active at the highest concentration tested (usually around $10^{-5}$M). Numerical value, if given, is $pD_2$ in log molar units, and for some compounds maximum relaxation relative to 2-methylthio ATP (<, ≈, or >) is indicated in parentheses. The taenia coli, vas deferens, and bladder were from guinea pig. The aorta, mesenteric artery, saphenous artery were from rabbit.

[c]For the saphenous artery, the percentages in brackets are response at 10 μM relative to the contraction produced by 1 μM α,β-MeATP (~half maximal effect). ATP in this assay is very weak ($EC_{50}$ = 1.78 mM). The highest concentrations of the analogues tested were 3–30 μM.

[d]6.2 ± 0.08 (n = 38).

[e]Data from Burnstock et al., Br. J. Pharmacol., 79, 907–913 (1983); Jacobson, in Comprehensive Medicinal Chemistry (C. Hansch et al., eds., Pergamon Press, 1990), pp. 601–642; Cooper et al., J. Biol. Chem., 264, 6202–6206 (1989); Cusack and Hourani, in Purines in Cellular Signaling (K. A. Jacobson et al., eds., Springer, 1990), pp. 254–259.

[f]Contraction, not relaxation.

[g]Relaxation observed, but $pD_2$ not calculable.

[h]This analog was approximately 100 times more potent than ATP in the bladder, but it produced tonic contractions rather than the phasic contractions of ATP. In the presence of indomethacin (1 μM), it was much less potent than ATP under the same conditions.

[i]Data from Burnstock et al., supra (1983).

[j]Data from Burnstock et al., Br. J. Pharmacol., 81, 533–541 (1984).

[k]Synthesized in accordance with Zimmet et al., supra.

[l]Caused contractions and increased the cholinergic twitch.

[m]Inhibited the cholinergic twitch.

Several of the compounds disclosed herein (including 8-(6-aminohexylamino)-ATP, adenosine N1-oxide 5'-triphosphate, 2-deoxy-ATP, 3'-acetylamino-3'-deoxy-ATP, 3-(p-hydroxyphenylpropionylamino)-3'-deoxy-ATP, 3'-benzylamino)-3-deoxy-ATP, and isopropylidene-AMP) displayed variant activity to the two subtypes of $P_2$ receptors detailed herein. 8-(6-Aminohexylamino)ATP and adenosine N1-oxide 5'-triphosphate were specific for $P_{2Y}$ receptors, and selective for the endothelial receptors of the rabbit aorta versus the mesenteric artery and taenia coli (and somewhat active in turkey erythrocytes). Isopropylidene-AMP had a similar profile, except that it appeared to be specific for the aortic endothelial $P_{2Y}$ receptor. 3-(p-Hydroxyphenyl-propionylamino-3'-deoxy-ATP also showed a high degree of selectivity for the aortic endothelial $P_{2Y}$ receptor versus other $P_{2Y}$ systems. 2'-Deoxy-ATP was specific for another $P_{2Y}$ receptor system, being equipotent with ATP in the taenia coli, and seven times less potent than ATP in the turkey erythrocyte, but being inactive in the five other preparations, thereby implying a selectivity for the taenia coli and erythrocyte $P_{2Y}$ receptors. An amino group instead of hydroxyl group at the 3'-position (e.g., 3'-amino-3'-deoxy-ATP) generally enhanced potency at $P_2$ receptors, a acylation or alkylation of the amine markedly affected potency and selectivity. Although the N-acetyl derivative (3'-acetylamino-3'-deoxy-ATP) was active in the vas deferens and urinary bladder, the only $P_{2Y}$ receptor which had any appreciable activity was that in the rabbit mesenteric artery.

3'-Benzylamino-3'-deoxy-ATP was the only compound that showed specificity for $P_{2X}$ receptors, and was active only in the vas deferens and urinary bladder. In both these preparations it was substantially more potent than ATP. It appears that there is bulk tolerance at the 3'-position of ATP at $P_{2X}$ receptors in general and in a more restricted fashion at $P_{2Y}$ receptors of the rabbit aorta.

One of the most potent known $P_{2Y}$ receptor agonists is 2-methylthio-ATP (Satchell and Maguire, supra; Burnstock et al., supra (1985)), which is much less potent than ATP at $P_{2U}$-receptors. The enhanced potency at both $P_{2X}$ and $P_{2Y}$ receptors and stability of long chain functionalized congeners of 2-MeS-ATP have been reported previously (Zimmet et al., supra). As disclosed herein, the most potent compound in all of the $P_{2Y}$ receptor assays proved to be a 2-alkylthio derivative of ATP (namely, 2-(6-cyanohexylthio)-ATP), which displayed nanomolar potency.

Unlike the result of the data of Examples 4–8, in which a close correlation between the potency of a series of eleven 2-alkylthio ATP derivatives in the turkey erythrocyte preparation and the guinea-pig taenia coli was demonstrated, in the study of a series of analogs substituted at other sites, such a correlation was not maintained. For example, ADP-β-S has a very high affinity for the turkey erythrocyte $P_{2Y}$ receptor, which led to its development as a radioligand used in receptor studies (Cooper et al., supra), but has no greater affinity for the $P_{2Y}$ receptor in the guinea-pig taenia coli than ATP or ADP.

The receptors in the vas deferens and urinary bladder appeared to be very similar with no purine derivative having a large differential effect in the two tissues. Three compounds (8-Br-ATP, N1,$N^6$-etheno-ATP, and isopropylidene-ATP) were inactive in the vas deferens while having a limited activity in the urinary bladder, however. Also, the pyrimidine compounds UTP and 5-F-UTP were as potent as or more potent than ATP in the bladder, yet were without effect in the vas deferens.

None of the agents had much of an effect on the rabbit saphenous artery. In this test, α,γ-methylene-ATP is a potent constrictor (Burnstock et al., 1987a), as it is also in the vas deferens and urinary bladder (Burnstock et al., Gen. Pharmacol., 16, 433–440, (1985)). However, compounds with modifications that made them potent agonists in the vas deferens and urinary bladder (e.g., 2-(6-cyanohexylthio)-ATP and 3'-benzylamino-3'-deoxy-ATP) were at best weak agonists in the saphenous artery.

The results disclosed herein demonstrate that the $P_2$ receptors in the seven tissues are all different from one another in their pharmacological profile. Within the $P_{2X}$ receptor and $P_{2Y}$ receptor families, there are further subtypes that can be distinguished by the selective actions of compounds of the present invention. Additionally, the following has been demonstrated; 1) high potency (particularly at $P_{2Y}$ receptors) of 2-alkylthio derivatives of ATP; 2) high selectivity of 8-(6-aminohexylamino)ATP and 2',3'-isopropylidene ATP for endothelial $P_{2Y}$ receptors; 3) selectivity of the potent agonist $N^6$-methylATP and the somewhat less potent agonist 2'-deoxy-ATP at $P_{2Y}$ receptors in the taenia coli; and 4) high potency of 3'-benzylamino-3'-deoxyATP at $P_{2X}$ receptors in the guinea-pig vas deferens and bladder, but not rabbit saphenous artery $P_{2X}$ receptors.

EXAMPLE 12

This example illustrates the inhibition of adenylyl cyclase activity in C6 rat glioma cells, as a function of the presence of certain ATP analogs in the medium in which the C6 cells were cultured.

The following results were obtained in the laboratory of Professor T. K. Harden at the University of North Carolina, using the methods as described here.

C6 rat glioma cells were grown in Dulbecco's Modified Eagle Medium supplemented with 5% fetal calf serum, in 95% air and 5% carbon dioxide. Cells were labelled by incubation for 2 hours in the presence of 1 to 2 mCi of tritiated adenine/ml in the medium. Cells were washed twice with HEPES (20 mM, pH 7.5)-buffered Eagle's medium and then preincubated for 10 minutes at 37° C. with fresh medium containing 200 µM 3-isobutyl-1-methylxanthine. Agonist incubations were initiated by the simultaneous addition of 10 µM isoproterenol and various concentrations of nucleotides. The reactions were stopped after 10 minutes of aspiration of the nucleotide-containing medium and addition of 1 ml of ice-cold 5% trichloroacetic acid. Tritiated cyclic AMP was determined by Dowex and alumina chromatography as described by Harden et al., Molecular Pharmacology, 21, 570–580 (1982).

$K_{0.5}$ values (in nM) for inhibition of adenylyl cyclase in C6 cells for the various derivatives were:

| | |
|---|---|
| 2-hexylthio-ATP | 0.03 ± 0.005 |
| 2-hexenylthio-ATP | 0.12 ± 0.06 |
| $N^6$-methyl-2-hexenylthio-ATP | 0.32 |
| 2-hexenylthio-ADP | 0.07 ± 0.02 |
| 2-hexenylthio-AMP | 2.0 ± 0.18 |
| p-nitrophenylethylthio-ATP | 1.0 ± 0.4 |

The results recited in Example 11 indicate, inter alia, that the presence of long-chain thioether at the 2-position of adenosine di- and triphosphates increased potency of the ATP analogs of the present invention. This structural feature correlated with selectivity of triphosphate analogies for the adenylyl cyclase linked receptor, as indicated in the results presented in this Example. The degree of selectivity depended very much on the structure of the thioether substituent. A small alkyl group, e.g., 2-MeSATP, provided only 7.3-fold selectivity. Larger alkyl thioethers, such as hexenyl and hexyl, resulted in selectivity for the C6 cell $P_{2Y}$ receptor of roughly 100-fold.

The presence of a cyano functional group at the distal position of the 2-(n-hexylthio) chain reduced the degree of selectivity from 170-to 3.9-fold, as noted by the change in potency in C6 cells. A 2-(2-(4-nitrophenyl)ethylthio)ether also displayed only moderate selectivity for C6 cell receptors. The enhancement of selectivity for the adenylyl cyclase linked receptor associated with the presence of a long chain 2-thioether was not observed for the 2-Cl analogue or for modification of ATP at other sites, e.g., $N^6,3'$, or on the triphosphate group. Thus, $N^6$-methyl ATP was slightly selective of the phospholipase C-linked receptor. The $N^6$-methyl substitution, however, did not preclude the appearance of selectivity for the adenylyl cyclase linked receptor, since $N^6$-methyl-2-(5-hexenylthio)-ATP was 81-fold selective. ADP itself was 120-fold selective for the adenylyl cyclase linked receptor, and approximately the same degree of selectivity was observed for a long chain (5-hexenyl) 2-thioether of ADP.

All of the references cited herein, including publications and patent applications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula

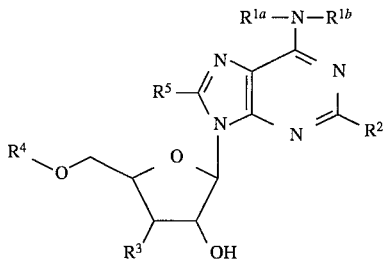

wherein one of $R^{1a}$ and $R^{1b}$ is hydrogen, and the other of $R^{1a}$ and $R^{1b}$ is $(C_1-C_7)$alkyl, $(C_1-C_7)$alkylphenyl, or $(C_5-C_{10})$ aryl $(C_1-C_7)$alkyl; $R^2$ is selected from the group consisting of S-$(C_1-C_{11})$alkyl, S-$(C_1-C_7)$alkenyl, S-$(C_1-C_7)$alkylcyano, S-$(C_3-C_7)$cycloalkyl, S-phenyl, S-$(C_1-C_3)$alkylphenyl, S-$(C_1-C_7)$alkylamino, S-$(C_1-C_7)$alkylthio$(C_1-C_7)$alkyl, S-$(C_1-C_7)$alkylthiocyanato, S-$(C_1-C_3)$alkylaminophenyl, S-$(C_1-C_3)$alkylnitrophenyl, and hydrogen; $R^3$ is selected from the group consisting of $(C_1-C_7)$alkyl, $(C_1-C_7)$alkylamino, $(C_5-C_{10})$aryl, $(C_5-C_{10})$arylamino, amino, amido, and hydroxyl; $R^4$ is monophosphate, diphosphate, or triphosphate; and $R^5$ is selected from the group consisting of bromo, fluoro, chloro, amino $(C_1-C_7)$alkyl amino, and hydrogen; or a pharmaceutically acceptable salt thereof;

provided that when $R^3$ is hydroxyl, then at least one of $R^2$ and $R^5$ is not hydrogen; and further provided that when $R^4$ is triphosphate, $R^3$ is hydroxyl and $R^5$ is hydrogen.

2. The compound of claim 1, wherein $R^{1a}$ and $R^{1b}$ are individually hydrogen or methyl; $R^2$ is selected from the group consisting of S-$(C_1-C_{11})$alkyl, S-$(C_1-C_7)$alkenyl, S-$(C_1-C_7)$alkylcyano, S-$(C_3-C_7)$cycloalkyl, S-phenyl, S-$(C_1-C_3)$alkylphenyl, S-$(C_1-C_3)$alkylaminophenyl, and S-$(C_1-C_3)$alkylnitrophenyl; $R^3$ is hydroxyl; $R^4$ is monophosphate or diphosphate; and $R^5$ is hydrogen.

3. The compound of claim 1, wherein $R^3$ is hydroxyl; $R^4$ is monophosphate; and $R^{1a}$, $R^{1b}$ and $R^5$ are each hydrogen.

4. The compound of claim 3, wherein $R^2$ is selected from the group consisting of S-5-hexenyl, S-2-(4-nitrophenyl) ethyl, S-6-cyanohexyl, S-ethylaminophenyl, S-ethylthioethyl, S-2-pentyl, S-2-hexyl, S-2-heptyl, S-2-octyl, S-2-decyl, and S-2-undecyl.

5. The compound of claim 1, wherein $R^{1a}$ is hydrogen; $R^{1b}$ is methyl; $R^3$ is hydroxyl; $R^4$ is monophosphate; and $R^5$ is hydrogen.

6. The compound of claim 5, wherein $R^2$ is S-5-hexenyl or S-ethylaminophenyl.

7. The compound of claim 1, wherein $R^3$ is hydroxyl; $R^4$ is diphosphate; and $R^{1a}$, $R^{1b}$, and $R^5$ are each hydrogen.

8. The compound of claim 7, wherein $R^2$ is S-5-hexenyl.

9. The compound of claim 1, wherein $R^{1a}$ is hydrogen, $R^{1b}$ is methyl; $R^3$ is hydroxyl; $R^4$ is diphosphate; and $R^5$ is hydrogen.

10. The compound of claim 9, wherein $R^2$ is selected from the group consisting of 2-(5-hexenyl)thio, 2-(2-(p-nitrophenyl)ethyl)thio, 2-(6-cyanohexyl)thio, and 2-aminophenylethylthio.

11. The compound of claim 1, wherein $R^{1a}$ is hydrogen, $R^{1b}$ is phenylethyl; $R^3$ is hydroxyl; $R^4$ is triphosphate; and $R^5$ is hydrogen.

12. $N^6$-phenylethyl-ATP.

13. A compound of the formula

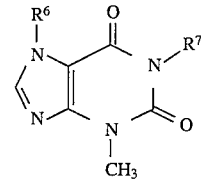

wherein one of $R^6$ and $R^7$ is a $C_1-C_3$ alkyltriphosphate and the other of $R^6$ and $R^7$ is a $(C_1-C_3)$alkyl; and a pharmaceutically acceptable salt thereof.

14. The compound of claim 13, wherein $R^6$ is ethyltriphosphate and $R^7$ is methyl.

15. The compound of claim 13, wherein $R^6$ is methyl and $R^7$ is ethyltriphosphate.

16. A pharmaceutical composition comprising a pharmaceutically acceptable carrier and at least one compound selected from the group consisting of

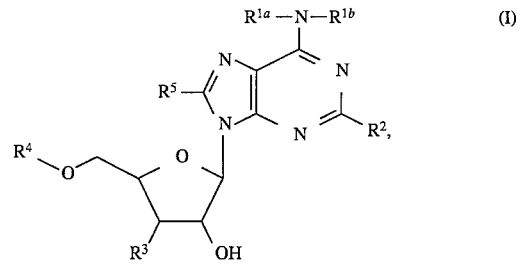

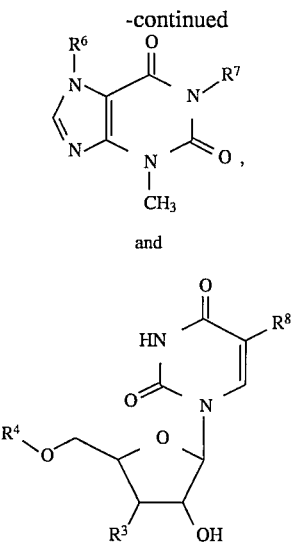

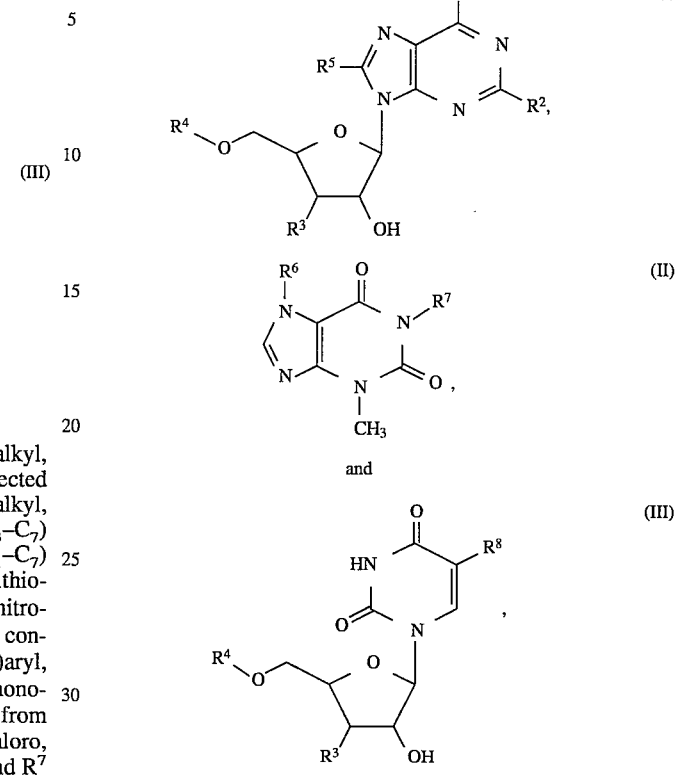

is hydrogen and the other of $R^{1a}$ and $R^{1b}$ is $(C_1-C_7)$alkyl, $(C_1-C_7)$alkylphenyl, or phenyl$(C_1-C_7)$alkyl; $R^2$ is selected from the group consisting of S-$(C_1-C_{11})$alkyl, S-$(C_1-C_7)$alkenyl, S-$(C_1-C_7)$alkylcyano, S-$(C_3-C_7)$ cycloalkyl, S-phenyl, S-$(C_1-C_3)$alkylphenyl, S-$(C_1-C_7)$ alkylamino, S-$(C_1-C_7)$alkylthioalkyl, S-$(C_1-C_7)$alkylthiocyanato, S-$(C_1-C_3)$alkylaminophenyl, S-$(C_1-C_3)$alkylnitrophenyl, and hydrogen; $R^3$ is selected from the group consisting of $(C_1-C_7)$alkyl, $(C_1-C_7)$alkyl amino, $(C_5-C_{10})$aryl, $(C_5-C_{10})$arylamino, hydrogen, and hydroxyl; $R^4$ is monophosphate, diphosphate, or triphosphate; $R^5$ is selected from the group consisting of bromo, fluoro, chloro, amino$(C_1-C_7)$alkyl amino, and hydrogen; one of $R^6$ and $R^7$ is a $(C_1-C_3)$alkyltriphosphate and the other of $R^6$ and $R^7$ is a $(C_1-C_3)$alkyl; and $R^8$ is selected from the group consisting of bromo, fluoro, chloro, and hydrogen; and a pharmaceutically acceptable salt thereof;

provided that when $R^4$ is triphosphate, $R^3$ is hydroxyl and $R^5$ is hydrogen.

17. The pharmaceutical composition of claim 16, wherein said compound is selected from the group consisting of formula (I) and formula (II); one of $R^{1a}$ and $R_{1b}$ is hydrogen and the other of $R^{1a}$ and $R^{1b}$ is methyl; $R^2$ is selected from the group consisting of S-$(C_1-C_{11})$alkyl, S-$(C_1-C_7)$alkenyl, S-$(C_1-C_7)$ alkylcyano, S-$(C_3-C_7)$cycloalkyl, S-phenyl, S-$(C_1-C_3)$alkylphenyl, S-$(C_1-C_3)$alkylaminophenyl, and S-$(C_1-C_3)$alkylnitrophenyl; $R^3$ is hydroxyl; $R^4$ is monophosphate, diphosphate, or triphosphate; and $R^5$ is hydrogen or amino$(C_1-C_7)$alkyl amine; and one of $R^6$ and $R^7$ is a $(C_1-C_3)$alkyltriphosphate and the other of $R^6$ and $R^7$ is a $(C_1-C_3)$alkyl; and a pharmaceutically acceptable salt thereof.

18. A method for the selective activation of $P_{2X}$ or $P_{2Y}$ receptors, or sub-classes thereof, comprising contacting said receptor with an effective quantity of at least one agonist, wherein said agonist is selected from the group consisting of 2-$(C_1-C_{11})$alkylthio derivatives of adenosyl monophosphates or diphosphates, 2-$(C_1-C_{11})$alkylthio derivatives of adenosyl triphosphates having $N^6$-$(C_1-C_7)$alkyl, 8-(6-aminohexylamino)ATP, 2', 3'-isopropylidene ATP, $N^6$-methylATP, 2'-deoxyATP, and 3'-benzylamino-3'-deoxyATP, and a pharmaceutically acceptable salt thereof.

19. A method for the treatment of septic shock or brain seizures in individuals in need of such treatment and for the improvement of memory and learning capabilities comprising contacting an effective quantity of a compound or combination of compounds to $P_{2X}$ or $P_{2Y}$ receptors, or sub-classes thereof, wherein said compound or combination of compounds is selected from the group consisting of wherein $R^{1a}$ and $R^{1b}$ are the same or different and are hydrogen, $(C_1-C_{11})$alkyl, or $(C_1-C_7)$alkylphenyl; $R^2$ is selected from the group consisting of S-$(C_1-C_{11})$alkyl, S-$(C_1-C_7)$alkenyl, S-$(C_1-C_7)$alkylcyano, S-$(C_3-C_7)$-cycloalkyl, S-$(C_3-C_7)$alkylphenyl, S-$(Ci-C_7)$ alkylamino, S-phenyl, S-$(C_1-C_3)$alkylphenyl, S-$(C_1-C_7)$alkylamino, S-$(C_1-C_7)$alkylthio, S-$(C_1-C_7)$alkylthiocyanato, S-$(C_1-C_3)$ alkylaminophenyl, S-$(C_1-C_3)$alkylnitrophenyl, and hydrogen; $R^3$ is selected from the group consisting of $(C_1-C_7)$alkyl, $(C_1-C_7)$alkyl amino, $(C_5-C_{10})$aryl, $(C_5-C_{10})$arylamino, hydrogen, and hydroxyl; $R^4$ is monophosphate, diphosphate, or triphosphate; $R^5$ is selected from the group consisting of bromo, fluoro, chloro, amino$(C_1-C_7)$alkyl amino, and hydrogen; $R^6$ and $R^7$ are different and selected from the group consisting of $(C_1-C_3)$alkyltriphosphate and $(C_1C_3)$alkyl; and $R^8$ is selected from the group consisting of bromo, fluoro, chloro, and hydrogen;

provided that when $R^3$ is hydroxyl, then at least one of $R^{1a}$, $R^{1b}$, $R^2$, $R^5$ is not hydrogen; and further provided that when $R^4$ is triphosphate, $R^3$ is hydroxyl and $R^5$ is hydrogen.

20. The compound of claim 1, wherein said compound is radiolabeled with $^3H$, $^{14}C$, $^{32}P$, $^{33}P$, or $^{125}I$.

21. The compound of claim 13, wherein said compound is radiolabeled with $^3H$, $^{14}C$, $^{32}P$, $^{33}P$, or $^{125}I$.

22. An assay for assessing the binding between an ATP analog and a sample, comprising contacting a compound of the formula

43

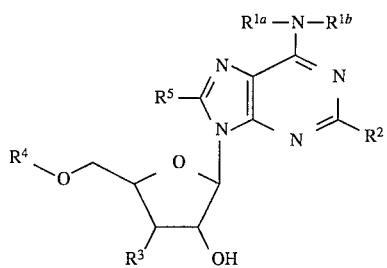

with a sample under conditions sufficient to effect binding between said compound and a component of said sample, and measuring the degree of said binding; wherein one of $R^{1a}$ and $R^{1b}$ is hydrogen, and the other of $R^{1a}$ and $R^{1b}$ is $(C_1-C_7)$alkyl, $(C_1-C_7)$alkylphenyl, or $(C_5-C_{10})$aryl $(C_1-C_7)$alkyl; $R^2$ is selected from the group consisting of S-$(C_1-C_{11})$alkyl, S-$(C_1-C_7)$alkenyl, S-$(C_1-C_7)$alkylcyano, S-$(C_3-C_7)$cycloalkyl S-phenyl, S-$(C_1-C_3)$alkylphenyl, S-$(C_1-C_7)$alkylamino, S-$(C_1-C_7)$alkylthio $(C_1-C_7)$alkyl, S-$(C_1-C_7)$alkylthiocyanato, S-$(C_1-C_3)$alkylaminophenyl, S-$(C_1-C_3)$alkylnitrophenyl, and hydrogen; $R^3$ is selected from the group consisting of $(C_1-C_7)$alkyl, $(C_1-C_7)$alkylamino, $(C_5-C_{10})$aryl, $(C_5-C_{10})$arylamino, amino, amido, and hydroxyl; $R^4$ is monophosphate, diphosphate, or triphosphate; and $R^5$ is selected from the group consisting of bromo, fluoro, chloro, amino$(C_1-C_7)$alkyl amino, and hydrogen; wherein said compound is radiolabelled with $^3H$, $^{14}C$, $^{32}P$, $^{33}P$, or $^{125}I$; or a pharmaceutically acceptable salt thereof; provided that when $R^4$ is triphosphate, $R^3$ is hydroxyl and $R^5$ is hydrogen.

23. An assay for assessing the binding between an ATP analog and a sample, comprising contacting a compound of claim 21 with a sample under conditions sufficient to effect binding between said compound and a component of said sample, and measuring the degree of said binding.

24. The pharmaceutical composition of claim 16, wherein said compound is radiolabeled with $^3H$, $^{14}C$, $^{32}P$, $^{33}P$, or $^{125}I$.

25. A compound of the formula

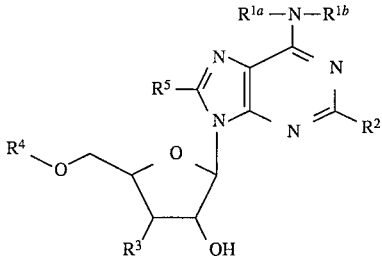

wherein $R^{1a}$ and $R^{1b}$ are the same or different and are hydrogen, $(C_1-C_7)$alkyl, $(C_1-C_7)$alkylphenyl, or $(C_5-C_{10})$aryl$(C_1-C_7)$alkyl; $R^2$ is selected from the group consisting of S-$(C_1-C_7)$alkenyl, S-$(C_1-C_7)$alkylcyano, S-$(C_3-C_7)$cycloalkyl, S-phenyl, S-$(C_1-C_3)$alkylphenyl, S-$(C_1-C_7)$alkylamino, S-$(C_1-C_7)$alkylthio $(C_1-C_7)$alkyl, S-$(C_1-C_7)$alkylthiocyanato, S-$(C_1-C_3)$alkylaminophenyl, S-$(C_1-C_3)$alkylnitrophenyl, and hydrogen; $R^3$ is selected from the group consisting of $(C_1-C_7)$alkyl, $(C_1-C_7)$alkylamino, $(C_5-C_{10})$aryl, $(C_5-C_{10})$arylamino, amino, amido, and hydroxyl; $R^4$ is monophosphate, diphosphate, or triphosphate; and $R^5$ is selected from the group consisting of bromo, fluoro, chloro, amino$(C_1-C_7)$alkyl amino, and hydrogen; or a pharmaceutically acceptable salt thereof;

provided that when $R^3$ is hydroxyl, then at least one of $R^2$ and $R^5$ is not hydrogen; and further provided that when $R^4$ is triphosphate, $R^3$ is hydroxyl and $R^5$ is hydrogen.

44

26. A compound of the formula

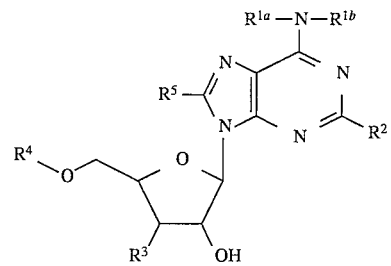

wherein $R^{1a}$ and $R^{1b}$ are same or different and are hydrogen, $(C_1-C_7)$alkyl, $(C_1-C_7)$alkylphenyl, or $(C_5-C_{10})$aryl $(C_1-C_7)$alkyl; $R^2$ is selected from the group consisting of S-$(C_1-C_7)$alkyl, S-$(C_1-C_7)$alkenyl, S-$(C_1-C_7)$alkylcyano, S-$(C_3-C_7)$cycloalkyl, S-phenyl, S-$(C_1-C_3)$alkylphenyl, S-$(C_1-C_7)$alkylamino, S-$(C_1-C_7)$alkylthio $(C_1-C_7)$alkyl, S-$(C_1-C_7)$alkylthiocyanato, S-$(C_1-C_3)$alkylaminophenyl, S-$(C_1-C_3)$alkylnitrophenyl, and hydrogen; $R^3$ is selected from the group consisting of $(C_1-C_7)$alkyl, $(C_1-C_7)$alkylamino, $(C_5-C_{10})$aryl, $(C_5-C_{10})$arylamino, amino, amido, and hydroxyl; $R^4$ is monophosphate or diphosphate; and $R^5$ is selected from the group consisting of bromo, fluoro, chloro, amino$(C_1-C_7)$alkyl amino, and hydrogen; or a pharmaceutically acceptable salt thereof; provided that when $R^3$ is hydroxyl, then $R^5$ is not hydrogen.

27. A pharmaceutical composition comprising a pharmaceutically acceptable carrier and a compound of claim 25.

28. A pharmaceutical composition comprising a pharmaceutically acceptable carrier and a compound of claim 26.

29. A compound of the formula

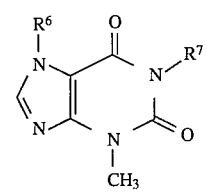

wherein $R^6$ and $R^7$ are selected from the group consisting of $(C_1-C^3)$alkyltriphosphates; and a pharmaceutically acceptable salt thereof.

30. A pharmaceutical composition comprising a pharmaceutically acceptable carrier and a compound of claim 29.

31. A pharmaceutical composition comprising a pharmaceutically acceptable carrier and at least one compound selected from the group consisting of

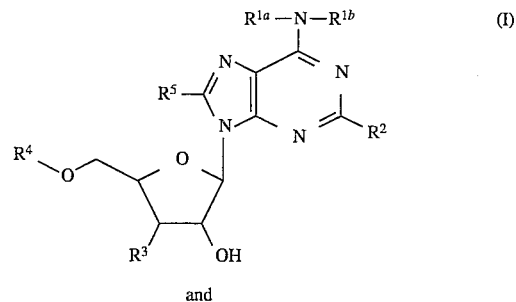

and

-continued

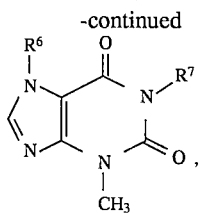
(II)

wherein $R^{1a}$ and $R^{1b}$ are same or different and are hydrogen, $(C_1-C_7)$alkyl, $(C_1-C_7)$alkylphenyl, or phenyl $(C_1-C_7)$alkyl; $R^2$ is selected from the group consisting of S-$(C_1-C_{11})$alkyl, S-$(C_1-C_7)$alkenyl, S-$(C_1-C_7)$alkylcyano, S-$(C_3-C_7)$cycloalkyl, S-phenyl, S-$(C_1-C_3)$alkylphenyl, S-$(C_1-C_7)$alkylamino, S-$(C_1-C_7)$alkylthioalkyl, S-$(C_1-C_7)$alkylthiocyanato, S-$(C_1-C_3)$alkylaminophenyl, S-$(C_1-C_3)$alkylnitrophenyl, and hydrogen; $R^3$ is selected from the group consisting of $(C_1-C_7)$alkyl, $(C_1-C_7)$alkyl amino, $(C_5-C_{10})$aryl, $(C_5-C_{10})$arylamino, hydrogen, and hydroxyl; $R^4$ is monophosphate, diphosphate; and triphosphate; $R^5$ is selected from the group consisting of bromo, fluoro, chloro, amino$(C_1-C_7)$alkyl amino, and hydrogen; one of $R^6$ and $R^7$ is a $(C_1-C_3)$alkyltriphosphate and the other of $R^6$ and $R^7$ is a $(C_1-C_3)$alkyl; or a pharmaceutically acceptable salt thereof;

provided that when $R^3$ is hydroxyl, then at least one of $R^2$ and $R^5$ is not hydrogen; and further provided that when $R^4$ is triphosphate, $R^3$ is hydroxyl and $R^5$ is hydrogen.

32. The compound of claim 25, wherein said compound is radiolabeled with $^3H$, $^{14}C$, $^{32}P$, $^{33}P$, or $^{125}I$.

33. The compound of claim 25, wherein said compound is radiolabeled with $^3H$, $^{14}C$, $^{32}P$, $^{33}P$, or $^{125}I$.

34. The compound of claim 25, wherein said compound is radiolabeled with $^3H$, $^{14}C$, $^{32}P$, $^{33}P$, or $^{125}I$.

* * * * *